United States Patent
Rajagopalan et al.

(10) Patent No.: US 12,195,606 B2
(45) Date of Patent: Jan. 14, 2025

(54) STRETCHABLE SOLID-STATE ELECTROACTIVE POLYMER ACTUATORS

(71) Applicant: BIOASTRA TECHNOLOGIES INC., Montreal (CA)

(72) Inventors: Sumitra Rajagopalan, Montreal (CA); Prajwal Kumar, Montreal (CA); Oscar Suarez, Saint-Laurent (CA); Sajjad Saeidlou, Montreal (CA); Maksym Kryuchkov, Pointe-Claire (CA); Mathieu Ramananarivo, Montreal (CA); Alexey Tokarev, Montreal (CA); Nicolas Cottenye, Montreal (CA); Julien Plathier, Montreal (CA)

(73) Assignee: BIOASTRA TECHNOLOGIES, INC., Montreal (CA)

( * ) Notice: Subject to any disclaimer, the term of this patent is extended or adjusted under 35 U.S.C. 154(b) by 793 days.

(21) Appl. No.: 16/972,069

(22) PCT Filed: Jun. 4, 2019

(86) PCT No.: PCT/CA2019/050772
§ 371 (c)(1),
(2) Date: Dec. 4, 2020

(87) PCT Pub. No.: WO2019/232621
PCT Pub. Date: Dec. 12, 2019

(65) Prior Publication Data
US 2021/0115220 A1    Apr. 22, 2021

Related U.S. Application Data

(60) Provisional application No. 62/680,618, filed on Jun. 5, 2018.

(51) Int. Cl.
*C08K 5/053* (2006.01)
*A41D 27/10* (2006.01)
(Continued)

(52) U.S. Cl.
CPC .............. *C08K 5/053* (2013.01); *A41D 27/10* (2013.01); *A61B 34/30* (2016.02); *B32B 5/02* (2013.01);
(Continued)

(58) Field of Classification Search
None
See application file for complete search history.

(56) References Cited

U.S. PATENT DOCUMENTS 6,987,663 B2 *   1/2006   Merker .................. H01G 11/56
                                                        29/25.03
2006/0086596 A1   4/2006   Lee et al.
(Continued)

FOREIGN PATENT DOCUMENTS

| CA | 877851 | * | 8/1971 |
| EP | 2892090 A1 | | 7/2015 |
| WO | 2016079696 A2 | | 5/2016 |

OTHER PUBLICATIONS

Jl of Polymer Science Part A Polymer Chemistry vol. 33-1657-1663 Jean Li (1995).*

(Continued)

*Primary Examiner* — Kenneth J Stachel
(74) *Attorney, Agent, or Firm* — BCF LLP

(57) ABSTRACT

There are provided stretchable solid-state electroactive polymer actuators (SSEPA) using electroactive polymers that convert between electrical energy and mechanical energy and having solid-state polymer electrolytes. More particularly, there are provided electroactive polymer (EAP) compositions comprising: 15-60 wt. % of a film-forming polymer; 5-40 wt. % of poly(3,4-ethylenedioxythiophene) polystyrene sulfonate (PEDOT:PSS) and 10-40 wt. % of a plasticizer, solid-state polymer electrolyte (SPE) compositions comprising: 20-60 wt. % of a plasticizer, 10-60 wt. % of a film-forming polymer and 5-25 wt. % of an ionizable (Continued)

salt. The use of these EAP and SPE compositions in electromechanical devices, such as solid-state actuators, generators, sensors, and other energy transducers in various applications are also disclosed.

19 Claims, 29 Drawing Sheets

(51) Int. Cl.
| | |
|---|---|
| A61B 34/30 | (2016.01) |
| B32B 5/02 | (2006.01) |
| B32B 15/08 | (2006.01) |
| B32B 27/12 | (2006.01) |
| B32B 27/20 | (2006.01) |
| B32B 27/22 | (2006.01) |
| B32B 27/30 | (2006.01) |
| B32B 27/32 | (2006.01) |
| B32B 27/36 | (2006.01) |
| C08K 3/18 | (2006.01) |
| C09D 129/04 | (2006.01) |
| F03G 7/00 | (2006.01) |
| G09B 23/30 | (2006.01) |

(52) U.S. Cl.
CPC .............. *B32B 15/08* (2013.01); *B32B 27/12* (2013.01); *B32B 27/20* (2013.01); *B32B 27/22* (2013.01); *B32B 27/302* (2013.01); *B32B 27/306* (2013.01); *B32B 27/308* (2013.01); *B32B 27/32* (2013.01); *B32B 27/36* (2013.01); *B32B 27/365* (2013.01); *C08K 3/18* (2013.01); *C09D 129/04* (2013.01); *F03G 7/005* (2013.01); *G09B 23/30* (2013.01); *B32B 2262/103* (2013.01); *B32B 2264/1027* (2020.08); *B32B 2270/00* (2013.01); *B32B 2307/20* (2013.01); *B32B 2307/54* (2013.01); *B32B 2307/732* (2013.01); *B32B 2437/00* (2013.01); *B32B 2457/00* (2013.01); *B32B 2535/00* (2013.01)

(56) References Cited

U.S. PATENT DOCUMENTS

| | | |
|---|---|---|
| 2007/0247033 A1 | 10/2007 | Eidenschink et al. |
| 2009/0251027 A1* | 10/2009 | Kudoh .................. F03G 7/005 29/25.35 |
| 2009/0259315 A1 | 10/2009 | Banik |
| 2011/0066091 A1 | 3/2011 | Larson et al. |
| 2013/0278991 A1 | 10/2013 | Daniel et al. |
| 2017/0346129 A1 | 11/2017 | Stolyarov |

OTHER PUBLICATIONS

Yuechen Li—Smart Mater-Struct—23_ 074010) (2014).*
Supplementary European Search Report issued in corresponding EP application No. 19815833.9 on Jan. 21, 2022.
Khandelwal et al., Fabrication of a novel biomaterial with enhanced mechanical and conducting properties, Journal of Materials Chemistry B, Aug. 5, 2014, vol. 2, pp. 7327-7333.
Chen et al., Electrical conductivity of polymer blends of Poly(3, 4-ethylenedioxythiophene): Poly(styrenesulfonate): N-Methyl-2-pyrrolidinone and Polyvinyl Alcohol, Journal of Applied Polymer Science, Feb. 1, 2012, vol. 125, pp. 3134-3141.
Li et al., Poly(ethylene oxide)/(Poly(2-vinylpyridine)/Lithium Perchlorate blends. New Materials for solid polymer electrolytes, Chem. Mater., 1992, vol. 4, pp. 1131-1134.
International Search Report and Written Opinion issued in corresponding application No. PCT/CA2019/050772 on Aug. 1, 2019.

* cited by examiner

SSEPA-23

| Extension at Break (Load/Tensile strain Rate 0 kgf/mm/mm) (mm) | Extension at Maximum Tensile stress (mm) | Load at Maximum Tensile stress (kgf) | Modulus (Automatic Young's) (kgf/cm²) |
|---|---|---|---|
| 1.80189 | 1.80153 | 0.50294 | 321.16121 |

SSEPA-24

| Extension at Break (Load/Tensile strain Rate 0 kgf/mm/mm) (mm) | Extension at Maximum Tensile stress (mm) | Load at Maximum Tensile stress (kgf) | Modulus (Automatic Young's) (kgf/cm$^2$) |
|---|---|---|---|
| 141.60047 | 141.60024 | 9.78333 | 133.82676 |

SSEPA-20

| Extension at Break (Load/Tensile strain Rate 0 kgf/mm/mm) (mm) | Extension at Maximum Tensile stress (mm) | Load at Maximum Tensile stress (kgf) | Modulus (Automatic Young's) (kgf/cm$^2$) |
|---|---|---|---|
| 133.47422 | 133.47398 | 7.34392 | 627.48146 |

SSEPA-22

| Extension at Break (Load/Tensile strain Rate 0 kgf/mm/mm) (mm) | Extension at Maximum Tensile stress (mm) | Load at Maximum Tensile stress (kgf) | Modulus (Automatic Young's) (kgf/cm$^2$) |
|---|---|---|---|
| 1.72905 | 1.72893 | 0.52025 | 59.82483 |

SSEPA-22

| Extension at Break (Load/Tensile strain Rate 0 kgf/mm/mm) (mm) | Extension at Maximum Tensile stress (mm) | Load at Maximum Tensile stress (kgf) | Modulus (Automatic Young's) (kgf/cm$^2$) |
|---|---|---|---|
| 2.41023 | 2.40999 | 0.53258 | 65.97308 |

SSEPA-25

| Extension at Break (Load/Tensile strain Rate 0 kgf/mm/mm) (mm) | Extension at Maximum Tensile stress (mm) | Load at Maximum Tensile stress (kgf) | Modulus (Automatic Young's) (kgf/cm$^2$) |
|---|---|---|---|
| 77.35654 | 77.35606 | 6.19180 | 53,876.55612 |

SSEPA-26

| Extension at Break (Load/Tensile strain Rate 0 kgf/mm/mm) (mm) | Extension at Maximum Tensile stress (mm) | Load at Maximum Tensile stress (kgf) | Modulus (Automatic Young's) (kgf/cm²) |
|---|---|---|---|
| 31.80192 | 31.80133 | 3.21673 | 44,590.59451 |

SSEPA-27

| Extension at Break (Load/Tensile strain Rate 0 kgf/mm/mm) (mm) | Extension at Maximum Tensile stress (mm) | Load at Maximum Tensile stress (kgf) | Modulus (Automatic Young's) (kgf/cm$^2$) |
|---|---|---|---|
| 38.82720 | 38.82661 | 2.46300 | 53,640.88551 |

SSEPA-28:

| Extension at Break (Load/Tensile strain Rate 0 kgf/mm/mm) (mm) | Extension at Maximum Tensile stress (mm) | Load at Maximum Tensile stress (kgf) | Modulus (Automatic Young's) (kgf/cm²) |
|---|---|---|---|
| 31.56734 | 31.56687 | 2.71008 | 64,535.99527 |

SSEPA-21

| Extension at Break (Load/Tensile strain Rate 0 kgf/mm/mm) (mm) | Extension at Maximum Tensile stress (mm) | Load at Maximum Tensile stress (kgf) | Modulus (Automatic Young's) (kgf/cm$^2$) |
|---|---|---|---|
| 1.03653 | 1.03594 | 0.59152 | 143,748.17403 |

STRETCHABLE SOLID-STATE ELECTROACTIVE POLYMER ACTUATORS

CROSS-REFERENCE TO RELATED APPLICATIONS

This application is a national phase filing under 35 U.S.C. 371 of International Application No. PCT/CA2019/050772 filed on Jun. 4, 2019, which claims the benefit of priority from U.S. Provisional Application No. 62/680,618 filed on Jun. 5, 2018, which is incorporated by reference herein in its entirety.

FIELD

The disclosure relates generally to stretchable solid-state electroactive polymer actuators having one or more layer of electroactive polymer (EAP) and one or more layer of solid-state polymer electrolyte (SPE), and methods of preparation and articles of manufacture thereof.

BACKGROUND

In many applications, it is desirable to convert between electrical energy and mechanical energy. Exemplary applications requiring translation from electrical to mechanical energy include robotics, pumps, speakers, general automation, disk drives and prosthetic devices. These applications include one or more actuators that convert electrical energy into mechanical work on a macroscopic or microscopic level. Common electric actuator technologies, such as electromagnetic motors and solenoids, are not suitable for many of these applications, e.g., when the required device size is small (e.g., micro or mesoscale machines). Other applications requiring translation from mechanical to electrical energy include mechanical property sensors and heel strike generators. These applications include one or more transducers that convert mechanical energy into electrical energy. However, common electric generator technologies, such as electromagnetic generators, are not suitable for many of these applications, e.g., when the required device size is small (e.g., in a person's shoe). These technologies are also not ideal when a large number of devices must be integrated into a single structure or under various performance conditions such as when high power density output is required at relatively low frequencies.

Polymeric devices that can directly convert electrical energy to mechanical energy (electromechanical effects) have attracted a great deal of attention in recent years. The definite advantages of such polymeric devices originate from their soft mechanical properties (inherently polymeric behavior) that have a significant potential to mimic various biological situations necessary to enhance human activities and/or serve as special industrial actuators. Electroactive polymers are advantageous because they have larger variation and smaller density, as well as faster response properties, compared to those of other small actuator materials. Electroactive polymers are known to have properties similar to those of natural muscles and therefore have potential application in various small robot actuators. Known materials in this category include conducting polymers, ferroelectric polymers, ionic polymer metal composites, and ionic polymeric gels. Limited success in converting between electrical and mechanical energy has also been achieved with smart materials including piezoelectric ceramics, shape memory alloys and magnetostrictive materials.

However, each of these materials has limitations that prevent its broad usage. For example, ferroelectric materials such as poly(vinyliedene fluoride-trifluoroethylene, PVDF-TrFE) copolymer require very high electric field (>10 kV/mm) for an appropriate range of actuation capabilities to attract engineering applications. Ionic polymer metal composites in a form of a strip show a large bending capability under a small electric field (<10 V/mm) along with considerable forces and fast responses, however the operation of these devices is effective only in wet climates, therefore, the engineering applications are limited to wet environments. Ionic polymer gels, such as PVA fibers and polyacrylamide, have also been shown to have electromechanical behavior, however such ionic polymer gels suffer from their weak mechanical strength and consequent microfractures upon large deformations and result in short life span materials. For some materials such as piezoelectric ceramics and irradiated PVDF, in addition to performance limitations, their fabrication often presents a barrier to acceptability, requiring processes that are expensive and complex.

In addition, conventional electroactive actuators which use a liquid electrolyte have drawbacks, such as limited variation and low current application range. Electroactive solid-state actuators using a solid electrolyte substituted for the liquid electrolyte have therefore been developed in recent years. Such electroactive solid-state actuators typically comprise a three-layer structure including a solid-state electrolyte such as silicon rubber or an acrylic material and a pair of compliant electrodes formed on opposite surfaces of the sheet.

U.S. Pat. No. 7,224,106 describes electroactive polymers and devices including electroactive polymers to convert between electrical and mechanical energy, as well as compliant electrodes that conform to the shape of a polymer included in a transducer, and methods for fabricating electromechanical devices including one or more electroactive polymers. Polymers may be pre-strained to improve their mechanical response.

U.S. Pat. No. 7,442,760 describes electroactive polymeric arylenes and intermediates useful for making such polymers, as well as organic electronic devices which comprise these polymers and compositions and methods of fabricating these devices.

U.S. Pat. No. 7,671,514 describes an electroactive solid-state actuator, including a solid polymer electrolyte film having first and second main surfaces facing each other, and first and second conductive polymer layers infiltrated into the first and second main surfaces of the solid polymer electrolyte film. A method of manufacturing the electroactive solid-state actuator is also provided, the method including preparing a solid polymer film having first and second main surfaces facing each other, infiltrating a monomer of a conductive polymer into the first and second main surfaces of the solid polymer film, followed by polymerization, to form first and second conductive polymer layers, and immersing the solid polymer film into an ionic liquid or liquid electrolyte to be converted to an electrically conductive polymer.

U.S. Pat. No. 8,100,819 describes electroactive polymer actuators, control units for electrically controlling one or more electroactive polymer actuator to expand or contract the devices, and artificial muscle patches and sphincter cuffs comprising these devices.

In view of the foregoing, alternative devices that convert between electrical and mechanical energy without the need for any liquid electrolytic medium would be desirable.

SUMMARY

The present disclosure relates generally to solid-state electroactive polymer actuators using electroactive polymers that convert between electrical energy and mechanical energy and solid-state polymer electrolytes. More particularly, the present disclosure relates to electroactive polymer compositions, solid-state polymer electrolyte compositions, and their use as actuators, generators, sensors, and other energy transducers in various applications, as well as methods of preparation therefor. In some embodiments the solid-state electroactive polymer actuators (SSEPAs) provided herein have improved properties, such as improved strength and/or stretchability, compared to previous actuators of this type.

In a first broad aspect, there is provided an electroactive polymer (EAP) composition that converts between electrical and mechanical energy. When a voltage is applied to electrodes contacting an EAP, the EAP deflects, and this deflection may be used to do mechanical work. Similarly, when the EAP deflects, an electric field is produced in the EAP, and this electric field may be used to produce electrical energy.

EAP compositions provided herein comprise about 15-60 wt % of a film-forming polymer; about 5-40 wt % of an electroactive polymer; and about 10-40 wt % of a plasticizer.

Examples of film-forming polymers for use in EAP compositions include, without limitation, poly(vinyl alcohol) (PVA), polyethylene glycol (PEG), styrene-butadiene rubber (SBR), poly(ethylene-vinyl acetate) (PEVAc), and polyvinyl acetate (PVAc), polyvinylpyrrolidone (PVP), polyvinylidene fluoride (PVDF), poly(vinylidene fluoride-co-hexafluoropropylene) (PVDF-HFP), polyethylene oxide (PEO), polyethylene glycol and polyethylene oxide acrylate and/or diacrylate, polyethylene glycol and polyethylene oxide methacrylate and/or dimethacrylate, amylopectin, amylose, starch, and combinations thereof.

Examples of electroactive polymers for use in EAP compositions include, without limitation, poly(3,4-ethylenedioxythiophene) polystyrene sulfonate (PEDOT:PSS), polyaniline, polypyrrole, and combinations thereof.

Examples of plasticizers for use in EAP compositions include, without limitation, glycerol, polyethylene glycol (PEG), ethylene glycol, N-ethyl toluene sulfonamide, zonyl fluorosurfactant (zonyl), and 4-Dodecylbenzenesulfonic acid (DBSA).

In one embodiment, there is provided an EAP composition comprising about 15-60 wt % PVA, about 5-40 wt % PEDOT:PSS, and about 10-40 wt % glycerol. In a particular embodiment, there is provided an EAP composition comprising about 47 wt % PVA, about 28 wt % PEDOT:PSS, and about 26 wt % glycerol.

In some embodiments, the EAP is pre-strained to improve the mechanical response of the EAP relative to a non-strained EAP. The pre-strain may vary in different directions of an EAP to vary response of the EAP to the applied voltage.

In some embodiments, the EAP film layer is pre-stretched during manufacturing to increase pressure generation of the SSEPA.

In some embodiments, the EAP includes laminate layers that improve conversion between electrical and mechanical energy.

EAP compositions may be made using standard techniques known in the art, such as without limitation casting, solution casting, dipping, spin coating, spraying, compression molding or other known processes for fabrication of thin polymer layers. In a particular embodiment, EAP compositions are preparable or are prepared using extrusion techniques known in the art, e.g. using a single or twin screw extruder, e.g., by blown film extrusion, sheet/film extrusion, coextrusion, and the like. In an embodiment, EAP films are made using extrusion (e.g., a twin-screw extruder) to prepare the EAP composition and then compression molded into a film. In another embodiment, EAP films are made using twin-screw extrusion followed by a sheet/film extrusion (slit die) to make EAP film in a continuous process.

In some embodiments, the EAP composition is provided in the form of a film having a thickness of from about 50 µm to about 500 µm, e.g., about 170 µm, about 200 µm, about 230 µm, or about 250 µm, or about 200+/−30 µm.

In some embodiments, an EAP composition may optionally further comprise 0-50 wt % of a reinforcing filler such as, without limitation, nanocrystalline cellulose (NCC) or clay. In alternative embodiments, a reinforcing filler is not included, the film-forming polymer being selected so as to provide sufficient reinforcement in the absence of a separate filler such as NCC or clay. For example, in some embodiments the film-forming polymer is PVAc or PEVAc which provides sufficient reinforcement in combination with the plasticizer N-ethyl toluene sulfonamide to obviate the need for a separate filler such as NCC or clay. Clay may be pristine or organically modified. Examples of clay include, without limitation, montmorillonite, silicon dioxide ($SiO_2$), and kaolin clay. Non-limiting examples of fillers that may be used include graphene, graphite, carbon black, graphene oxide, carbon nanotubes, and the like.

In a second broad aspect, there is provided a solid-state polymer electrolyte (SPE) composition. SPE compositions provided herein comprise about 20-60 wt % of a plasticizer; about 15-60 wt % of one or more film-forming polymer; and about 5-25 wt % of an ionizable salt. Examples of plasticizers for use in SPE compositions include plasticizers that can dissolve the salt used in the SPE, such as, without limitation, glycerol, polyethylene glycol (PEG), and ethylene glycol. Examples of film-forming polymers for use in SPE compositions include, without limitation, poly(vinyl alcohol) (PVA), polyethylene glycol (PEG), styrene-butadiene rubber (SBR), poly(ethylene-vinyl acetate) (PEVA), polyvinyl acetate (PVAc), polyvinylpyrrolidone (PVP), polyvinylidene fluoride (PVDF), poly(vinylidene fluoride-co-hexafluoropropylene) (PVDF-HFP), polyethylene oxide (PEO), starch, glycerol, EG or PEG esters of (meth)acrylic acid derivatives (e.g., PEG acrylate (PEGA), PEG diacrylate (PEGDA), PEG methacrylate (PEGMA), PEG dimethacrylate (PEGDMA), glycerol acrylate, glycerol diacrylate, glycerol methacrylate, glycerol dimethacrylate, glycidyl acrylate, glycidyl methacrylate, or propylene carbonate methacrylate), styrene-co-ethylene-co-ethylenepropylene-co-styrene (SEEPS), styrene-co-ethylene-co-butylene-co-styrene (SEBS), amylose, amylopectin, and combinations thereof. In an embodiment, a composite of two film-forming polymers is used. In an embodiment, a composite of amylose, amylopectin, and another film-forming polymer is used. In an embodiment, a composite of starch and another film-forming polymer is used. In an embodiment, a composite of starch, amylose, amylopectin, and another film-forming polymer is used. Examples of ionizable salts for use in SPE compositions include, without limitation, lithium perchlorate ($LiClO_4$), lithium bis(trifluoromethanesulfonyl) imide (LiTFSI), lithium polyacrylate (LiPAA), lithium chloride (LiCl), sodium chloride (NaCl), sodium sulfate ($NaSO_4$), sodium carbonate, sodium nitrate, sodium carbonate, a potassium halide (e.g., potassium chloride, potassium bromide), potassium perchlorate, potassium nitrate, potassium nitrite, potassium ferrocyanide [$K_3Fe(CN)_6$] and potassium ferricyanide [$K_4Fe(CN)_6$]. In some embodiments, a SPE composition includes about 10-60 wt % of one or more film-forming polymer. In some embodiments, a SPE composition includes about 20-60 wt % of one or more film-forming polymer.

In one embodiment, there is provided a SPE composition comprising about 40 wt % glycerol, about 15 wt % starch, about 15 wt % PVA, about 14 wt % $LiClO_4$, about 8.8 wt % NCC and about 7.4 wt % Kaolin clay. In some embodiments, the starch is corn starch. It should be understood however that any kind of starch can be used in compositions provided herein.

In some embodiments, a SPE composition may optionally further comprise 0-50 wt % of a reinforcing filler such as, without limitation, nanocrystalline cellulose (NCC) or clay (e.g., montmorillonite, silicon dioxide ($SiO_2$), or kaolin clay). In alternative embodiments, a reinforcing filler is not included, the film-forming polymer being selected so as to provide sufficient reinforcement in the absence of a separate filler such as NCC or clay. Non-limiting examples of fillers that may be used include graphene, graphite, carbon black, graphene oxide, carbon nanotubes, and the like.

SPE compositions may be made using standard techniques known in the art, such as without limitation casting, solution casting, dipping, spin coating, spraying, compression molding or other known processes for fabrication of thin polymer layers. In a particular embodiment, SPE compositions are made using extrusion techniques known in the art, e.g. using a single or twin screw extruder, e.g., by blown film extrusion, sheet/film extrusion, coextrusion, and the like. In one embodiment, the SPE composition is prepared by casting. In another embodiment, the SPE composition is preparable or is prepared by extrusion to form a film. In an embodiment, SPE films are made using extrusion (e.g., a twin-screw extruder) to prepare the SPE composition and then compression molded into a film. In another embodiment, SPE films are made using twin-screw extrusion followed by a sheet/film extrusion (slit die) to make SPE film in a continuous process.

In some embodiments, the SPE composition is provided in the form of a film having a thickness of from about 100 μm to about 2000 μm, from about 150 μm to about 2000 μm, or about 400 μm, about 450 μm, about 500 μm, or about 450+/−50 μm.

In a third broad aspect, there is provided a solid-state electroactive polymer actuator (SSEPA) comprising one or more layer of the EAP composition and one or more layer of the SPE composition provided herein. In some embodiments, the SSEPA is generally laminated and comprises at least one layer of the SPE composition sandwiched between two layers of the EAP composition, as shown in the schematic diagrams in FIGS. 1 and 2, which are provided by way of example and are not meant to be limiting. In such embodiments electromechanical devices provided herein generally comprise at least two EAP composition (electrode) layers and at least one SPE composition (electrolyte) layer, arranged in a manner which causes a change in electric field in response to deflection of at least a portion of the EAP and/or which causes at least a portion of the EAP to deflect in response to a change in electric field. However, the number and organization of layers may vary and the structure and composition of the SSEPA are not meant to be particularly limited. In other embodiments, electromechanical devices provide herein comprise only one EAP composition (electrode) layer arranged on one side of the SPE composition (electrode) layer, the SPE layer being arranged next to a carbon electrode layer on its other side; such embodiments are referred to herein as "asymmetric" SSEPAs. Asymmetric SSEPAs are advantageous in certain applications where linear movement, without bending, is desired. For example, asymmetric SSEPAs may have application for bracing and/or for tightening for prosthetic, orthotic, bracing and gripping applications.

Without wishing to be limited by theory, it is believed that SSEPAs provided herein can, in some embodiments, provide improved mechanical properties such as increased strength, increased stretchability, and/or increased mechanical stability, compared to previous solid-state actuators. In some embodiments, SSEPAs provided herein have improved strength and stretchability compared to previous solid-state actuators. In some embodiments, SSEPAs described herein can provide one or more of the following performance measurements: Blocking force of from 1 mN-1 N per gram of SSEPA assembly; Pressure of 0.5 mmHg-50 mmHg; Displacement of 1-60 degrees; Extension ratio of about 6-560% or greater; and Young's modulus in the range of 6 MPa-6330 MPa.

In a fourth broad aspect, there are provided methods for fabricating EAP compositions, SPE compositions, and SSEPAs comprising the EAP and SPE compositions. In an embodiment, the method comprises mixing a film-forming polymer, an electroactive polymer, and a plasticizer to prepare an EAP composition, and forming a film therefrom; mixing a plasticizer, a film-forming polymer; and an ionizable salt to prepare an SPE composition, and forming a film therefrom; and assembling an SSEPA therefrom. EAP and SPE composition film layers may be prepared using any standard technique such as, without limitation, casting, solution casting, dipping, spin coating, spraying, compression molding, extrusion, and the like. SSEPAs are then assembled by adhering EAP and SPE composition film layers together using any standard technique for adhering or laminating the layers together. It should be understood than an SSEPA may be fabricated using any standard technique known in the art. In some embodiments, individual layers of the SSEPA are first prepared by casting, followed by gluing of the layers together. In alternative embodiments, one or more of the layers is prepared by extrusion. In one embodiment, the SPE layer is prepared by extrusion. In still further embodiments, all the layers in the SSEPA (EAP composition layers and SPE composition layers) are prepared by extrusion, and the layers are then adhered together, e.g., using hot pressing methods. In other embodiments, layers in the SSEPA (EAP composition layers and SPE composition layers) are co-extruded.

In a fifth broad aspect, there are provided electromechanical devices and articles of manufacture comprising one or more SSEPA described herein.

It should be understood that polymer compositions and SSEPAs of the present technology may be used as conventional actuators to convert from electrical to mechanical energy or as generators to convert from mechanical to electrical energy. Many devices used today rely on actuators of one sort or another to convert electrical energy to mechanical energy. Actuators "give life" to these products, putting them in motion. Conversely, many power generation applications operate by converting mechanical action into electrical energy. Employed to harvest mechanical energy in this fashion, the same type of actuator may be referred to as a "generator". Likewise, when the SSEPA is employed to convert physical stimulus such as vibration or pressure into an electrical signal for measurement purposes, it may be referred to as a "transducer" or as a "sensor" (a sensor may also convert an electrical signal into a mechanical signal, for measurement purposes). SSEPAs provided herein may be used for any of these applications.

In some embodiments, a SSEPA is used as an actuator, i.e., to convert electrical energy to mechanical energy. In some embodiments, a SSEPA is used as a generator, i.e., to convert mechanical energy to electrical energy. In some embodiments, a SSEPA is used as a sensor, i.e., to measure force or pressure. Other types of energy transducers may also be made using EAP compositions, SPE compositions, and/or SSEPAs provided herein. Such actuators, generators, sensors, and other transducers of the present technology may be used to fabricate a wide variety of electromechanical devices and articles for converting mechanical energy to electrical energy and/or for converting electrical energy to mechanical energy. Examples of such devices and articles include, without limitation, pumps, valves, optical electrodes, artificial muscles, artificial sphincters, organic electronic devices, robotics, speakers, general automation, disk drives, prosthetic devices, spacesuits, and anti-gravity suits.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the invention and to show more clearly how it may be carried into effect, reference will now be made by way of example to the accompanying drawings, which illustrate aspects and features according to embodiments of the present invention, and in which:

FIG. 10A is a schematic diagram showing a side view of certain embodiments of the asymmetric SSEPA 500 of the present technology. FIG. 10B is a schematic diagram showing a top view of certain embodiments of the asymmetric SSEPA 500 of the present technology. FIG. 10C is a schematic presentation of a stacked actuator assembly in the relaxed state, in accordance with certain embodiments.

FIG. 14A shows the pressure variation under the actuator measured with different pressure sensors for a single actuator. FIG. 14B shows the pressure variation under the actuator measured with different pressure sensors for two stacked actuators.

FIG. 15A is a graph showing pressure change for an actuator with EAP pre-stretching in the width-wise direction during manufacture. FIG. 15B is a graph showing pressure change for an actuator without EAP pre-stretching during manufacture. FIG. 15C is a graph showing pressure change for an actuator with EAP pre-stretching in the lengthwise direction during manufacture.

FIG. 16A is a graph showing pressure change for an actuator without a rigid backing. FIG. 16B is a graph showing pressure change for an actuator with a rigid backing.

DETAILED DESCRIPTION

Figure 1:
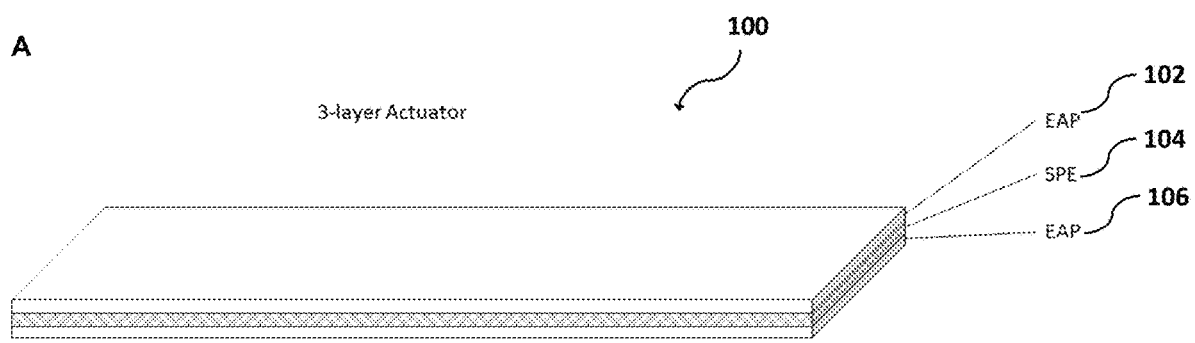
FIG. 1 is a schematic diagram of certain embodiments of a SSEPA of the present technology, wherein: (A) shows a 3-layer SSEPA 100 having an SPE composition layer 104 sandwiched between two EAP composition layers 102, 106 (EAP-SPE-EAP); and (B) shows a 5-layer SSEPA 200 having three EAP composition layers 202, 206, 210 and two SPE composition layers 204, 208 (EAP-SPE-EAP-SPE-EAP).
Figure 1:
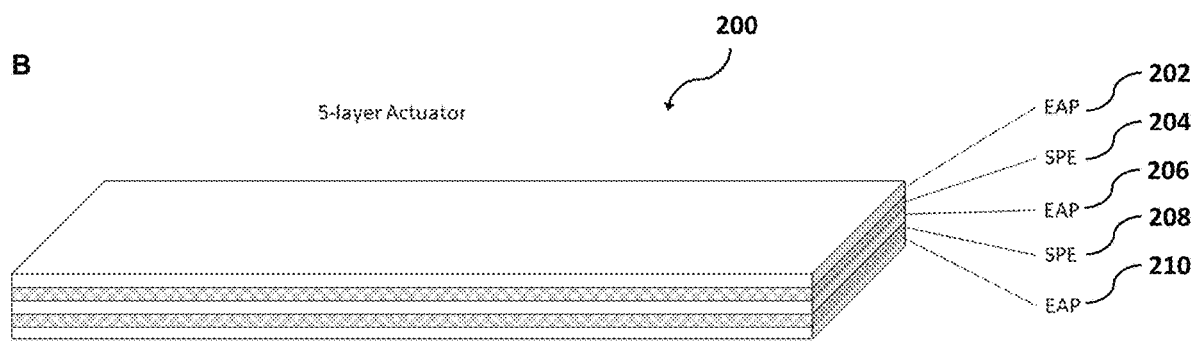

The terminology used in the description of the various described embodiments herein is for the purpose of describing particular embodiments only and is not intended to be limiting.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

Definitions

As used herein, the use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used herein, the words "comprising" (and any form of comprising, such as "comprise" and "comprises"), "having" (and any form of having, such as "have" and "has"), "including" (and any form of including, such as "include" and "includes") and "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "actuator" is used herein to refer to a machine or part of a machine which moves or controls another part in response to an input, i.e., a device for moving or controlling something.

The term "electroactive" is used generally to refer to a substance that exhibits electrical activity or is responsive to electrical stimuli.

The term "electroactive polymer" or "EAP" (also referred to as "conductive polymers" or "conducting polymers") is used herein to refer to polymers that exhibit a change in size or shape in response to electrical stimulation. Without wishing to be limited by theory, EAPs typically structurally feature a conjugated backbone and have the ability to increase electrical conductivity under oxidation or reduction. These materials are typically semi-conductors in their pure form. However, upon oxidation or reduction of the polymer, conductivity is increased. The oxidation or reduction leads to a charge imbalance that, in turn, results in a flow of ions into or out of the material in order to balance charge. These ions, or dopants, enter the polymer from an ionically conductive electrolyte medium that is coupled to the polymer surface. If ions are already present in the polymer when it is oxidized or reduced, they may exit the polymer. The mass transfer of ions both into and out of the polymer matrix leads to expansion or contraction of the polymer.

The term "solid-state polymer electrolyte" or "SPE" is used herein to refer to an ionically conducting solid-state solution of a salt in a polymeric matrix, the ionic conductivity of such material being due to the mobility of the salt ions and their counterions in an electric field.

The term "solid-state" is used herein to refer to devices having the properties, structure, or reactivity of solid material, including without limitation electronic devices, such as transistors and crystals.

The term "solid-state electroactive polymer actuator" or "SSEPA" is used broadly herein to refer to composites comprising the EAP compositions and SPE compositions of the present technology that convert electrical energy to mechanical energy or mechanical energy to electrical energy (or both, depending on the application). Solid-state electroactive polymer actuators (SSEPAs) may function as conventional actuators (e.g., moving or controlling something in response to an electrical stimulus), as generators (e.g., converting mechanical energy to electrical energy), as sensors (e.g., converting mechanical energy to electrical energy or vice-versa, for purposes of measurement), or as any other type of electroactive energy transducer.

The term "asymmetric SSEPA" is used herein to refer to SSEPAs of the present technology having only one EAP composition layer, the one EAP layer being arranged on one side of the SPE, the other side of the SPE being adjacent to a carbon electrode. The terms "asymmetric SSEPA", "non-symmetric SSEPA" and "linear SSEPA" are used interchangeably herein. Asymmetric SSEPAs can be advantageous for certain applications since they contract linearly only, without bending, due to the presence of only one EAP composition layer on one side of the SPE. This characteristic is beneficial for certain applications where bending is not desired and movement in one direction only, i.e., linear movement, is desired. In some embodiments, an asymmetric SSEPA has a strain ratio of at least about 1%, at least about 2%, or at least about 5%. In contrast, the term "symmetric SSEPA" is used herein to refer to SSEPAs of the present technology that have an SPE composition layer sandwiched between two EAP composition layers. Symmetric SSEPAs are generally bendable, for example in some embodiments they can have a bending angle of about 18 degrees.

In some embodiments, an asymmetric SSEPA moves only in one direction linearly, leading to a change in length after electrical activation. In some embodiments, an asymmetric SSEPA is not bendable. In some embodiments, in an asymmetric SSEPA, the conductive polymer chains in the EAP composition layer are oriented through treatment with a polar solvent (such as, without limitation, methanol, dimethyl formamide or ethanol). Such orientation through solvent processing can increase the electrical conductivity and/or force generation of the SSEPA.

As used herein, when content is indicated as being present on a "weight basis" or at a "weight percent (wt %)" or "by weight," the content is measured as the percentage of the weight of component(s) indicated by dry basis (by taking moisture percentage in each component into account), relative to the total weight of all components present in a composition.

The term "derivative" as used herein, is understood as being a substance similar in structure to another compound but differing in some slight structural detail.

As used herein, the term "polymer" refers to a material that includes a set of macromolecules. Macromolecules included in a polymer can be the same or can differ from one another in some fashion. A macromolecule can have any of a variety of skeletal structures, and can include one or more types of monomeric units. In particular, a macromolecule can have a skeletal structure that is linear or non-linear.

Examples of non-linear skeletal structures include branched skeletal structures, such those that are star branched, comb branched, or dendritic branched, and network skeletal structures. A macromolecule included in a homopolymer typically includes one type of monomeric unit, while a macromolecule included in a copolymer typically includes two or more types of monomeric units. Examples of copolymers include statistical copolymers, random copolymers, alternating copolymers, periodic copolymers, block copolymers, radial copolymers, and graft copolymers.

In some instances, a reactivity and a functionality of a polymer can be altered by addition of a set of functional groups, such as acid anhydride groups, amino groups and their salts, N-substituted amino groups, amide groups, carbonyl groups, carboxy groups and their salts, cyclohexyl epoxy groups, epoxy groups, glycidyl groups, hydroxy groups, isocyanate groups, urea or urethane or carbonate or allophanate groups, aldehyde groups, ester groups, ether groups, alkenyl groups, alkynyl groups, thiol or thioether or $S^+$-alkylthioether groups, disulfide groups, sulfanyl, sulfinyl, sulfoxide, sulfone, dialkylsilyl or dialkylsilyloxy or dialkylsilane groups, groups based on glyoxals or thioglyoxals, groups based on aziridines, groups based on active methylene compounds or other b-dicarbonyl compounds (e.g., 2,4-pentandione, malonic acid, acetylacetone, ethylacetone acetate, malonamide, acetoacetamide and its methyl analogues, ethyl acetoacetate, and isopropyl acetoacetate), halo groups, hydrides, or other polar or H bonding groups and combinations thereof. Such functional groups can be added at various places along the polymer, such as randomly or regularly dispersed along the polymer, at ends of the polymer, on the side, end or any position on the crystallizable side chains, attached as separate dangling side groups of the polymer, or attached directly to a backbone of the polymer. Also, a polymer can be capable of cross-linking, entanglement, or hydrogen bonding in order to increase its mechanical strength or its resistance to degradation under ambient or processing conditions.

"Polymerization" is a process of reacting monomer molecules together in a chemical reaction to form three-dimensional networks or polymer chains. Many forms of polymerization are known, and different systems exist to categorize them, as are known in the art.

As can be appreciated, a polymer can be provided in a variety of forms having different molecular weights, since a molecular weight (MW) of the polymer can be dependent upon processing conditions used for forming the polymer. Accordingly, a polymer can be referred to as having a specific molecular weight or a range of molecular weights. As used herein with reference to a polymer, the term "molecular weight (MW)" can refer to a number average molecular weight or a weight average molecular weight. Polymers are often referred to in terms of their average MW, for example PEG1000 refers to PEG of average MW of 1000. Polymers may also be referred to in terms of their degree of polymerization ("n"), which can range, generally, from as low as 40 to as high as 5000. In some cases, polymers of different molecular weights may be mixed to give a composition having desired properties. It should be understood that polymers of any molecular weight, or mixtures of polymers of different molecular weights, may be used, as long as the resulting composition has the desired properties or is generally suitable for the uses described herein, as will be determined by the skilled artisan using known techniques. In some embodiments of SSEPAs of the present technology, PEG having a molecular weight in a range of from about 400 Da to about 200,000 Da is used, for example PEG of about 400 Da, 500 Da, 1000 Da, 10000 Da, 50000 Da, 100,000 Da, 150,000 Da or about 200,000 Da, or mixtures thereof.

As used herein, the term "copolymer" refers to polymers having two or more different divalent monomer units.

As used herein, the term "chemical bond" refers to a coupling of two or more atoms based on an attractive interaction, such that those atoms can form a stable structure. Examples of chemical bonds include covalent bonds and ionic bonds. Other examples of chemical bonds include hydrogen bonds and attractive interactions between carboxy groups and amine groups. As used herein, the term "covalent bond" means a form of chemical bonding that is characterized by the sharing of pairs of electrons between atoms, or between atoms and other covalent bonds. Attraction-to-repulsion stability that forms between atoms when they share electrons is known as covalent bonding. Covalent bonding includes many kinds of interactions, including sigma-bonding, pi-bonding, metal-metal bonding, agostic interactions, and three-center two-electron bonds.

As used herein, the term "reactive function" means a chemical group (or a moiety) capable of reacting with another chemical group to form a covalent or an electrovalent bond, examples of which are given above. Preferably, such reaction is doable at relatively low temperatures, e.g. below 200° C., more preferably below 100° C., and/or at conditions suitable to handle delicate substrates, e.g. textiles. A reactive function could have various chemical natures. For example, a reactive function could be capable of reacting and forming electrovalent bonds or covalent bonds with reactive functions of various substrates, e.g., cotton, wool, fur, leather, polyester, or textiles made from such materials, as well as other base materials.

As used herein, the term "nanocrystalline filler" refers to a nanocrystalline material, e.g., a nanocrystalline particle or polymer, capable of providing mechanical reinforcement to a polymer by forming a nanocomposite material. In an embodiment, a nanocrystalline filler reinforces a polymer through non-covalent physical interactions such as, without limitation, hydrogen bonds or electrostatic attractions, and without attenuating or substantially adversely affecting other desired properties of the polymer (such as electroactivity). Non-limiting examples of fillers that may be used include graphene, graphite, carbon black, graphene oxide, carbon nanotubes, and the like.

Polymer Compositions

There are provided EAP compositions, SPE compositions and SSEPAs thereof that provide desirable performance characteristics such as strength (e.g., actuation pressure, blocking force), elasticity (e.g., extension ratio, Young's modulus), and electroactivity. In some embodiments, EAP compositions, SPE compositions and/or SSEPAs provided herein can provide one or more of the following performance measurements: Blocking force of from 1 mN-1 N per gram of SSEPA assembly; Pressure of 0.5 mmHg-50 mmHg; Displacement of 1-60 degrees; Extension ratio of about 6-560% or greater; and Young's modulus in the range of 6 MPa-6330 MPa. In an embodiment, a SSEPA has a Young's modulus of at least 5 MPa and/or an extension ratio of at least 50%. In another embodiment, a SSEPA has an extension ratio of from about 20% to about 200%. In another embodiment, SSEPAs provided herein have a blocking force of at least 200 mN, or a blocking force of from about 200 mN to about 1 N, and/or total actuation pressure of about 50 mmHg. In one embodiment, a SSEPA has a blocking force of from about 200 mN to about 1 N, a total actuation pressure of about 50 mmHg, an extension ratio of from about 20% to about 200%, and/or a Young's modulus of at least about 5 MPa.

EAP compositions that convert between electrical and mechanical energy (and vice-versa) generally comprise about 15-60 wt % of a film-forming polymer; about 5-40 wt % of an electroactive polymer; and about 10-40 wt % of a plasticizer. Examples of film-forming polymers for use in EAP compositions include, without limitation, poly(vinyl alcohol) (PVA), polyethylene glycol (PEG), styrene-butadiene rubber (SBR), poly(ethylene-vinyl acetate) (PEVAc), and polyvinyl acetate (PVAc), polyvinylpyrrolidone (PVP), polyvinylidene fluoride (PVDF), poly(vinylidene fluoride-co-hexafluoropropylene) (PVDF-HFP), polyethylene oxide (PEO), polyethylene glycol and polyethylene oxide acrylate and/or diacrylate, polyethylene glycol and polyethylene oxide methacrylate and/or dimethacrylate, amylopectin, amylose, starch, and combinations thereof. Examples of electroactive polymers for use in EAP compositions include, without limitation, poly(3,4-ethylenedioxythiophene) polystyrene sulfonate (PEDOT:PSS), polyaniline, polypyrrole, and combinations thereof, including composites of PEDOT: PSS with polypyrrole and composites of PEDOT:PSS with polyaniline (PANI). Examples of plasticizers for use in EAP compositions include, without limitation, glycerol, polyethylene glycol (PEG), ethylene glycol, N-ethyl toluene sulfonamide, zonyl fluorosurfactant (zonyl), and 4-Dodecylbenzenesulfonic acid (DBSA). In one embodiment, an EAP composition comprises about 15-60 wt % PVA, about 5-40 wt % PEDOT:PSS, and about 10-40 wt % glycerol. In an embodiment, an EAP composition comprises about 47 wt % PVA, about 28 wt % PEDOT:PSS, and about 26 wt % glycerol.

Additional non-limiting examples of film-forming polymers that may be used in certain embodiments include glycerol, EG and PEG esters of (meth)acrylic acid derivatives (e.g., PEG acrylate (PEGA); PEG diacrylate (PEGDA); PEG methacrylate (PEGMA), PEG dimethacrylate (PEGDMA), glycerol acrylate, glycerol diacrylate, glycerol methacrylate, glycerol dimethacrylate, glycidyl acrylate, glycidyl methacrylate, propylene carbonate methacrylate, etc.) and/or their block or random copolymers with polymers listed in the previous paragraph; cellophane, carboxymethyl cellulose (CMC), and methylcellulose (MC).

In some embodiments, EAP compositions comprise PEG, e.g., PEG having a molecular weight in a range of from about 400 Da to about 200,000 Da, for example PEG of about 400 Da, 500 Da, 1000 Da, 10000 Da, 50000 Da, 100,000 Da, 150,000 Da or about 200,000 Da, or mixtures thereof. In some embodiments the inclusion of PEG in the EAP compositions provides increased robustness to the SSEPA. For example, the SSEPA having PEG in the EAP may last for more cycles than SSEPAs without PEG, e.g., for about 100 actuation cycles, or for about 200 actuation cycles, and/or may undergo an increased frequency of cycles (more cycles/minute).

In some embodiments, EAP compositions comprise between about 5 wt % to about 30 wt % PEG, for example about 5 wt %, about 7 wt %, about 8 wt %, about 9 wt %, about 10 wt %, about 15 wt %, about 20 wt %, about 25 wt %, about 28 wt %, or about 30 wt %.

In some embodiments, EAP compositions may be prepared as an emulsion. In some such embodiments, the film-forming polymer is an amphiphilic polymer, such as polyvinylpyrrolidone (PVP). In other embodiments, the hydrophobic polymer that is stabilized in water with surfactants and/or colloidal stabilizers is used in emulsion form (e.g., SBR, PEVAc, PVAc).

SPE compositions that provide solid-state polymer electrolytes generally comprise about 20-60 wt % of a plasticizer; about 15-60 wt % of a film-forming polymer; and about 5-25 wt % of an ionizable salt. Examples of plasticizers for use in SPE compositions include plasticizers that can dissolve the salt used in the SPE, such as, without limitation, glycerol, polyethylene glycol (PEG), and ethylene glycol. Examples of film-forming polymers for use in SPE compositions include, without limitation, poly(vinyl alcohol) (PVA), polyethylene glycol (PEG), styrene-butadiene rubber (SBR), poly(ethylene-vinyl acetate) (PEVA), polyvinyl acetate (PVAc), polyvinylpyrrolidone (PVP), polyvinylidene fluoride (PVDF), poly(vinylidene fluoride-co-hexafluoropropylene) (PVDF-HFP), polyethylene oxide (PEO), glycerol, EG and PEG esters of (meth)acrylic acid derivatives (e.g., PEG acrylate (PEGA); PEG diacrylate (PEGDA); PEG methacrylate (PEGMA), PEG dimethacrylate (PEGDMA), glycerol acrylate, glycerol diacrylate, glycerol methacrylate, glycerol dimethacrylate, glycidyl acrylate, glycidyl methacrylate, propylene carbonate methacrylate, etc.) and/or their block or random copolymers, amylopectin, amylose, starch, and combinations thereof. In an embodiment, a composite of two film-forming polymers is used. In an embodiment, a composite of amylose, amylopectin, and another film-forming polymer is used. In an embodiment, a composite of starch and another film-forming polymer is used. In an embodiment, a composite of starch, amylose, amylopectin, and another film-forming polymer is used. Examples of ionizable salts for use in SPE compositions include, without limitation, lithium perchlorate ($LiClO_4$), lithium bis(trifluoromethanesulfonyl)imide (LiTFSI), lithium polyacrylate (LiPAA), lithium chloride (LiCl), sodium chloride (NaCl), sodium sulfate ($NaSO_4$), sodium carbonate, sodium nitrate, sodium carbonate, a potassium halide (e.g., potassium chloride, potassium bromide), potassium perchlorate, potassium nitrate, potassium nitrite, potassium ferrocyanide [$K_3Fe(CN)_6$] and potassium ferricyanide [$K_4Fe(CN)_6$]. In one embodiment, an SPE composition comprises about 40 wt % glycerol, about 15 wt % starch, about 15 wt % PVA, about 14 wt % $LiClO_4$, about 8.8 wt % NCC and about 7.4 wt % Kaolin clay. In some embodiments, SPE compositions comprise about 10-60 wt % of a film-forming polymer. In some embodiments, SPE compositions comprise about 20-60 wt % of a film-forming polymer.

In some embodiments of EAP and SPE compositions provided herein, where the compositions comprise PVA, PVA molecular weight may range from about 5000 to about 300,000. In some embodiments, the degree of hydrolysis of PVA may range from about 80% to about 100%. In an embodiment, PVA with molecular weight of about 9000 is used. In another embodiment, PVA with molecular weight of about 146,000 is used. In another embodiment, percentage hydrolysis of PVA used is about 89% or about 99%.

In some embodiments, EAP compositions and/or SPE compositions may comprise 0-50 wt % of a reinforcing filler such as, without limitation, nanocrystalline cellulose (NCC) or clay (e.g., montmorillonite, silicon dioxide ($SiO_2$), or kaolin clay). In alternative embodiments, a reinforcing filler is not included, the film-forming polymer being selected so as to provide sufficient reinforcement in the absence of a separate filler such as NCC or clay. For example, in some embodiments the film-forming polymer is PVAc or PEVAc which provides sufficient reinforcement in combination with the plasticizer N-ethyl toluene sulfonamide to obviate the need for a separate filler such as NCC or clay. Non-limiting examples of fillers that may be used include graphene, graphite, carbon black, graphene oxide, carbon nanotubes, and the like.

In some embodiments, a nanocrystalline filler is a nanocrystalline polymer. Many nanocrystalline and semi-crystalline polymers are known and may be used as nanocrystalline fillers in EAP and/or SPE compositions described here. In an embodiment, a cellulose-based polymer is used as a nanocrystalline filler. Examples of cellulose-based polymers include hydroxypropyl cellulose (HPC), microcrystalline cellulose (MCC) and nanocrystalline cellulose (NCC). In an embodiment, a nanocrystalline filler comprises nanocrystalline cellulose (NCC). In another embodiment, a nanocrystalline filler is a nanocrystalline starch, a nanoclay, a carbon nanotube, an organic nanoclay, an organoclay, a clay, or any electrospun polymer nanofiber. Non-limiting examples of nanocrystalline fillers for use in EAP and/or SPE compositions described herein include montmorillonite, bentonite, kaolinite, hectorite, halloysite, and liquid crystalline polymers such as Poly(γ-benzyl glutamate). In an embodiment, a nanocrystalline filler comprises clay. Many different types of clay may be used, including without limitation montmorillonite, silicon dioxide ($SiO_2$), and/or kaolin clay.

In some embodiments, EAP compositions and/or SPE compositions comprise one or more additive to improve various properties of the compositions. Examples of suitable classes of additives include without limitation plasticizers, antioxidants, and high dielectric constant particulates. Examples of suitable plasticizers include high molecular weight hydrocarbon oils, high molecular-weight hydrocarbon greases, Pentalyne H, Piccovar® AP Hydrocarbon Resins, Admex 760, Plastolein 9720, silicone oils, silicone greases, Floral 105, Benzoflex™, silicone elastomers, non-ionic surfactants, and the like, and combinations thereof.

In an embodiment, additives improve the ability of an EAP to convert between mechanical energy and electrical energy (and vice-versa). Generally, an additive may improve any polymer property or parameter related to the ability of the parameter to convert between mechanical energy and electrical energy. Polymer material properties and parameters related to the ability of the polymer to convert between mechanical energy and electrical energy include, for example, the dielectric breakdown strength, maximum strain, dielectric constant, elastic modulus, properties associated with visco-elastic performance, properties associated with creep, response time and actuation voltage. The addition of a plasticizer may, for example, improve the functioning of a SSEPA provided herein by reducing the elastic modulus of the polymer and/or increasing the dielectric breakdown strength of the polymer. In one embodiment, an additive is included in a polymer to improve the dielectric breakdown strength of the polymer.

Alternatively, an additive may be used to reduce the elastic modulus of a polymer. Reducing the elastic modulus enables larger strains for the polymer. For example, mineral oil, acrylic acids, and acrylic adhesives may be added to reduce the elastic modulus of the polymer.

In alternative embodiments, additives are used to reduce stiffness or to increase the elastic modulus of a polymer.

Additives may be used to improve performance of one or more material properties, for example to stabilize a formulation, to provide additional functional properties, to facilitate crosslinking to a substrate or article, to provide adhesive properties, to facilitate conversion between electrical and mechanical energy, etc. In certain embodiments, one or more than one additive is used. Non-limiting examples of crosslinking agents to be used with EAPs and/or SPEs described herein include divinylbenzene, phenol/formaldehyde, polyethylenimine, carbodiimides, diisocyanates, ethylene glycol, glyoxal, methylenbisacrylamide, PEG-diacrylate, and PEG-dimethacrylate. Non-limiting examples of other additives to be used with EAPs and/or SPEs provided herein include fixatives, rheology modifiers, UV stabilizers, plasticizers, surfactants, fluorosurfactants, emulsifiers, antistatic additives, flame retardants, friction reduction agents, anti-blocking agents, freezing point depressants, IR reflecting agents, and lubricants. Crosslinking agents such as (3-Glycidyloxypropyl)trimethoxysilane (GOPS), divinylsulfone (DVS), borax, and glutaraldehyde may also be used. Additional non-limiting examples of additives that may be used include dimethacrylate ethyleneglycol (DMEG), diethyleneglycol diacrylate (DMDEG), and PEG dimethyl ether (DM-PEG). Additional non-limiting examples of additives that may be used include cellophane, carboxymethyl cellulose (CMC), and methylcellulose (MC). Additives are chosen by the skilled artisan based on EAPs and/or SPEs used, desired properties, substrates or articles to be coated, and so on.

In some embodiments, an EAP is pre-strained to improve the mechanical response of the EAP relative to a non-strained EAP. Pre-strain can improve the dielectric strength of the polymer, thereby offering improvement for conversion between electrical and mechanical energy by allowing higher field potentials. The pre-strain may vary in different directions of an EAP to vary response of the EAP to an applied voltage. In some embodiments, an SPE is pre-strained to enhance ion mobility. In some embodiments, a SSEPA is pre-strained to improve stretchability and other mechanical properties of the SSEPA and/or to improve ion mobility and general response of the SSEPA to an electric field. In general, pre-strain of an actuator facilitates the alignment of conductive polymer chains, which can ease transport of charge carriers (electrons, holes) along the EAP chain under an electric field. Further, pre-strain can shorten the path length for charge carrier mobility. These effects improve ion mobility in the EAP layer and ultimately improve conductivity of the EAP, thereby improving performance of the SSEPA.

In some embodiments, EAP and/or SPE compositions include laminate layers that improve conversion between electrical and mechanical energy. For example, there may be provided a multilayer laminate that includes one or more layers in addition to the at least two EAP composition layers and the at least one SPE composition layer in the SSEPA, the additional layers being laminated to at least one of an EAP composition layer and/or an SPE composition layer. There may be provided external multilayer laminates, in which the one or more additional layers are not between SPE composition layers, or internal multilayer laminates, in which the one or more additional layers are between SPE composition layers. Such one or more additional layers may be adhered using an adhesive or glue layer, for example.

Internal multilayer laminates may be used for a wide variety of purposes. For example, a layer may be included in an internal multilayer laminate to improve any mechanical or electrical property of an EAP composition layer or a SSEPA thereof, e.g., stiffness, electrical resistance, tear resistance, etc. Internal multilayer laminates may include a layer having a greater dielectric breakdown strength. Internal multilayer laminates may include multiple layers of compatible materials separated by conducting or semiconducting layers (e.g., metallic or polymer layers) to increase breakdown strength of a SSEPA. Internal laminates of compatible materials relative to an EAP may be used to compensate for manufacturing defects in an EAP and to provide greater SSEPA uniformity and/or stability.

External multilayer laminates may be used for a wide variety of purposes. In one embodiment, an external multi-layer composite includes a layer to control stiffness, creep, to distribute load more uniformly during deflection, to increase tear resistance, or to prevent runaway pull effect. External laminates of compatible polymers may be used for example to distribute load across each of the polymer layers or increase polymer uniformity during deflection. A layer may also be included in an external laminate having a higher stiffness than the polymer, e.g., a material having a higher stiffness or a different amount of pre-strain for a compatible material, to bias a diaphragm, pump or bending beam. In a generator mode, a stretched SSEPA may contract and generate electrical energy as long as the electrical field stresses are lower than the elastic restoring stresses. In this case, adding a stiffening layer may allow the SSEPA to contract against greater field stresses, thereby increasing its energy output per stroke. An external layer may also be used to afford a layer of protection (electrical or mechanical) to another layer in a SSEPA. An external layer having a low stiffness may also be used for electric shielding without introducing excessive mechanical energy loss.

EAP and/or SPE compositions may be made using standard techniques known in the art, such as without limitation casting, solution casting, dipping, compression molding, spin coating, spraying or other known processes for fabrication of thin polymer layers. In a particular embodiment, EAP and/or SPE compositions are made using extrusion techniques known in the art, e.g. using a single or twin screw extruder, e.g., by blown film extrusion, sheet/film extrusion, coextrusion, and the like. Fabrication techniques are described further below. In an embodiment, EAP and/or SPE compositions are extrudable and can be prepared in the form of a uniform or homogeneous film. Films may then be adhered together, e.g., using hot pressing methods, such as without limitation in a temperature range of from 50-120° C. for 5-30 minutes. Alternatively, films may be co-extruded.

In some embodiments, EAP and/or SPE compositions are provided in the form of a film having a thickness of from about 50 µm to about 500 µm, from about 100 µm to about 2000 µm, or of about 250 µm, of about 200 µm, or of about 450 µm.

In some embodiments, polymers used herein in EAP compositions and/or SPE compositions are composites, e.g., combinations of more than one polymer. In some embodiments, polymers used herein in EAP compositions and/or SPE compositions are copolymers.

In some embodiments, components of EAP compositions and/or SPE compositions may be chemically modified. For example, starch may be chemically modified. As another example, a film-forming polymer such as PVA may be chemically modified, e.g., to increase hydrophobicity, thereby decreasing crystallinity of the polymer matrix.

General Structure of SSEPAs and Other Electromechanical Devices

Solid-state electroactive actuators and other electromechanical devices have been described (see, e.g., U.S. Pat. Nos. 6,249,076; 7,224,106; 7,468,575; 7,671,514; 7,442,760; 7,276,090; 7,595,580; and 8,100,819, each of which is incorporated by reference herein in its entirety). It should be understood that SSEPAs and other electromechanical devices comprising the EAP composition and SPE composition polymer layers provided herein may be structured and constructed accordingly as known in the art. Several SSEPAs are described here by way of example only, and these examples should not be taken as limiting in any way the structures or methods of fabrication of SSEPAs, devices, or articles of manufacture thereof.

Referring to FIG. 1A, in accordance with one embodiment of the present technology, the SSEPA 100 includes three layers: a first EAP composition layer 102; an SPE composition layer 104; and a second EAP composition layer 106, the SPE composition layer 104 being sandwiched in-between the first EAP composition layer 102 and the second EAP composition layer 106. When voltage is applied across the SSEPA 100, a deflection or movement occurs. Such deflection or movement can be variously controlled in accordance with the polarity and magnitude of the applied voltage.

Referring to FIG. 1B, in accordance with one embodiment, the SSEPA 200 includes five layers: a first EAP composition layer 202; a first SPE composition layer 204; a second EAP composition layer 206; a second SPE composition layer 208; and a third EAP composition layer 210.

Figure 2:
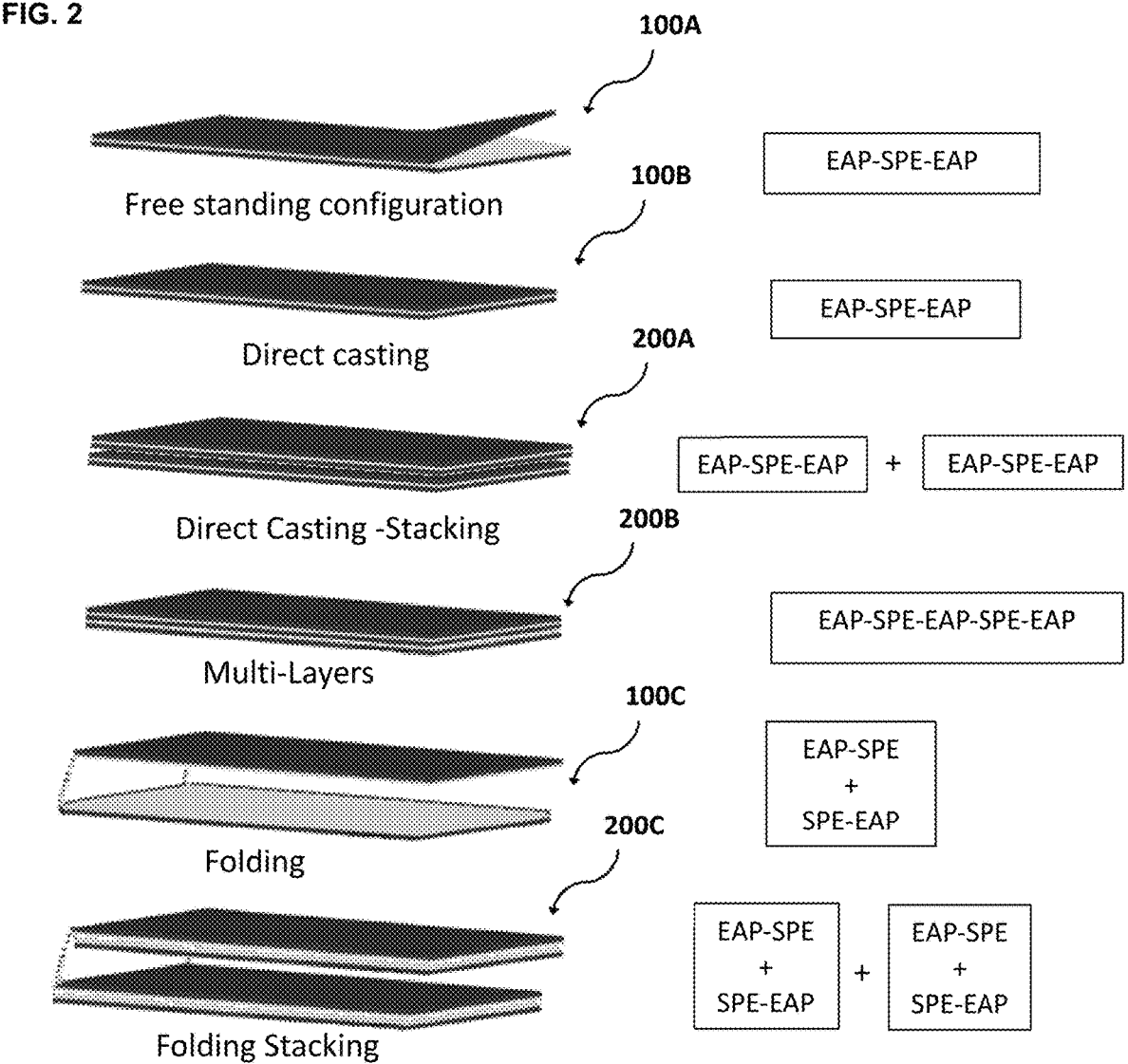
FIG. 2 is a schematic diagram showing certain embodiments of SSEPAs of the present technology.

SSEPAs may be fabricated using a wide variety of methods as known in the art. Referring to FIG. 2, the three-layer SSEPA 100A may be prepared as a free standing configuration (i.e., capable of standing on its own without being supported by a rigid substrate). Alternatively, three-layer SSEPA 100B may be prepared by direct casting. Alternatively, three-layer SSEPA 100C may be prepared by folding a SPE-EAP bilayer on top of itself. Two three-layer SSEPAs 100 may be stacked together to form six layer SSEPA 200A. Alternatively five layers may be directly cast to form five-layer SSEPA 200B. Alternatively, two three-layer SSEPAs 100C may be stacked together to form six-layer SSEPA 200C. In an alternative embodiment (not depicted), five-layer SSEPA 200 is prepared by folding three-layer SSEPA 100 over on top of itself. In another embodiment (not depicted), five layers are directly cast to form five-layer SSEPA 200.

Figure 10A:
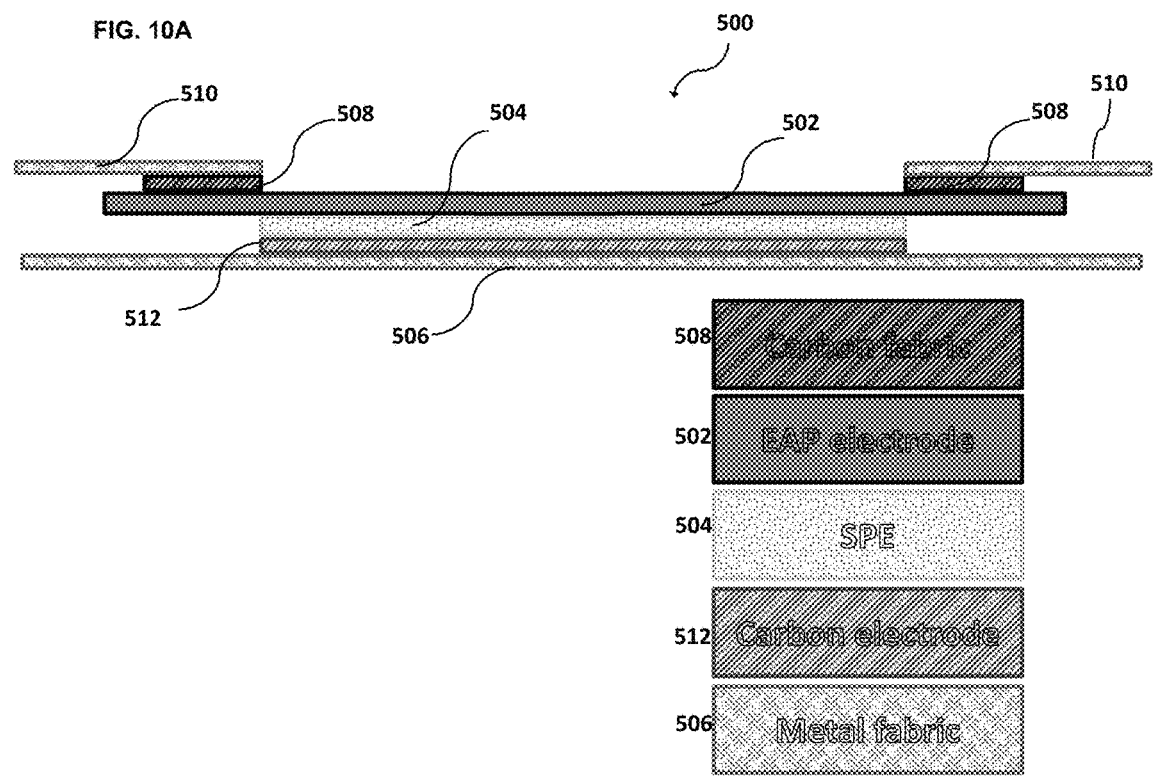
FIGS. 10A-10C show assembly of an asymmetric actuator in accordance with certain embodiments of the present technology.
Figure 10B:
Figure 10:
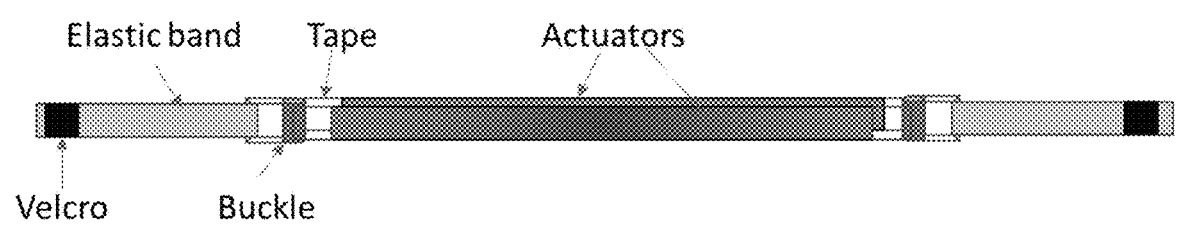

Referring to FIGS. 10A-10B, in accordance with one embodiment, the SSEPA 500 is asymmetric, i.e., it contains only one EAP composition layer 502 on one side of the SPE composition layer 504, the other side of the SPE composition layer 504 being adjacent to a carbon electrode layer 512, which is next to a metal fabric 506. The EAP composition layer 502 is also next to carbon fabric 508, which is next to a second layer of metal fabric 510.

Although the embodiments shown in FIGS. 1 and 2 and 10A-B are shown as conventional actuators, it should be understood that the SSEPAs 100 and 200 and 500 could be configured as generators, sensors, or other energy transducers, etc. Furthermore, the structure of the SSEPAs of the present technology is not particularly limited and the number, size and configuration of EAP and SPE composition layers may vary, depending on many factors such as the particular application.

Figure 12A:
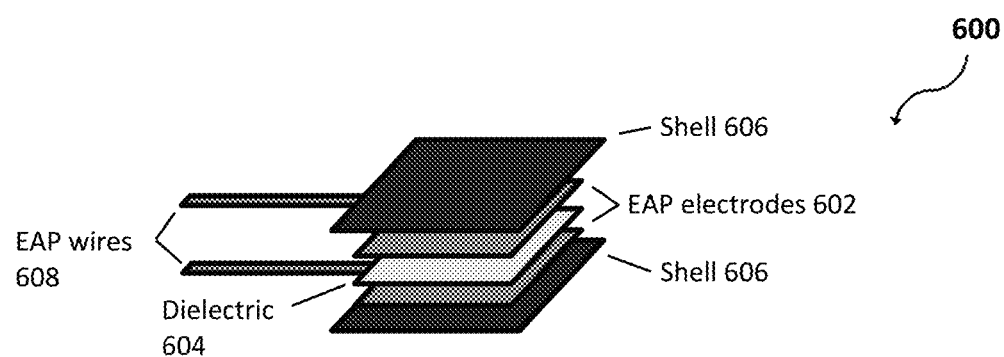
FIG. 12A is a schematic diagram showing a scheme of an electroactive polymer capacitive sensor with capacitive sensor layers and an array of 4 sensors, in accordance with certain embodiments of the present technology.

Referring to FIG. 12A, in accordance with one embodiment, the SSEPA 600 is configured for use as an electroactive polymer capacitive sensor. In the SSEPA 600, a dielectric film layer 604 is sandwiched between two EAP electrodes 602. These three layers are sandwiched between two polymeric Shell 606 layers, effectively sealing the dielectric film layer 604 and the EAP electrodes 602 in a protective polymer shell. When the distance between the two EAP electrodes 602, or their area, changes, an electrical signal is transmitted through the two EAP wires 608 (one EAP wire 608 being attached to each EAP electrode 602). In this way the SSEPA 600 can sense a mechanical stimulus such as pressure or bending. Both qualitative change of pressure (e.g., contact sensor) and quantitative pressure or mass can be sensed by the SSEPA 600. As the SSEPA 600 is made entirely of polymers, it is highly flexible. Moreover, it can be easily assembled as an array to form a multipoint sensing surface.

The dielectric film layer 604 is not particularly limited. Any suitable stretchable, flexible dielectric polymer can be used. Non-limiting examples include styrene-co-ethylene-co-ethylenepropylene-co-styrene (SEEPS), styrene-co-ethylene-co-butylene-co-styrene (SEBS), Poly (dimethyl siloxane), cellulose-based polymers, polyurethane, and combinations thereof.

Fabrication

There are provided methods for fabricating solid-state electroactive polymer actuators (SSEPAs) including one or more (or two or more) EAP composition layer(s) and one or more SPE composition layer. As the EAP composition and SPE composition layers may be implemented in a wide variety of SSEPA designs, with a range of materials, and in a broad range of applications, it should be understood that fabrication processes used with the present technology may vary greatly.

Figure 3:
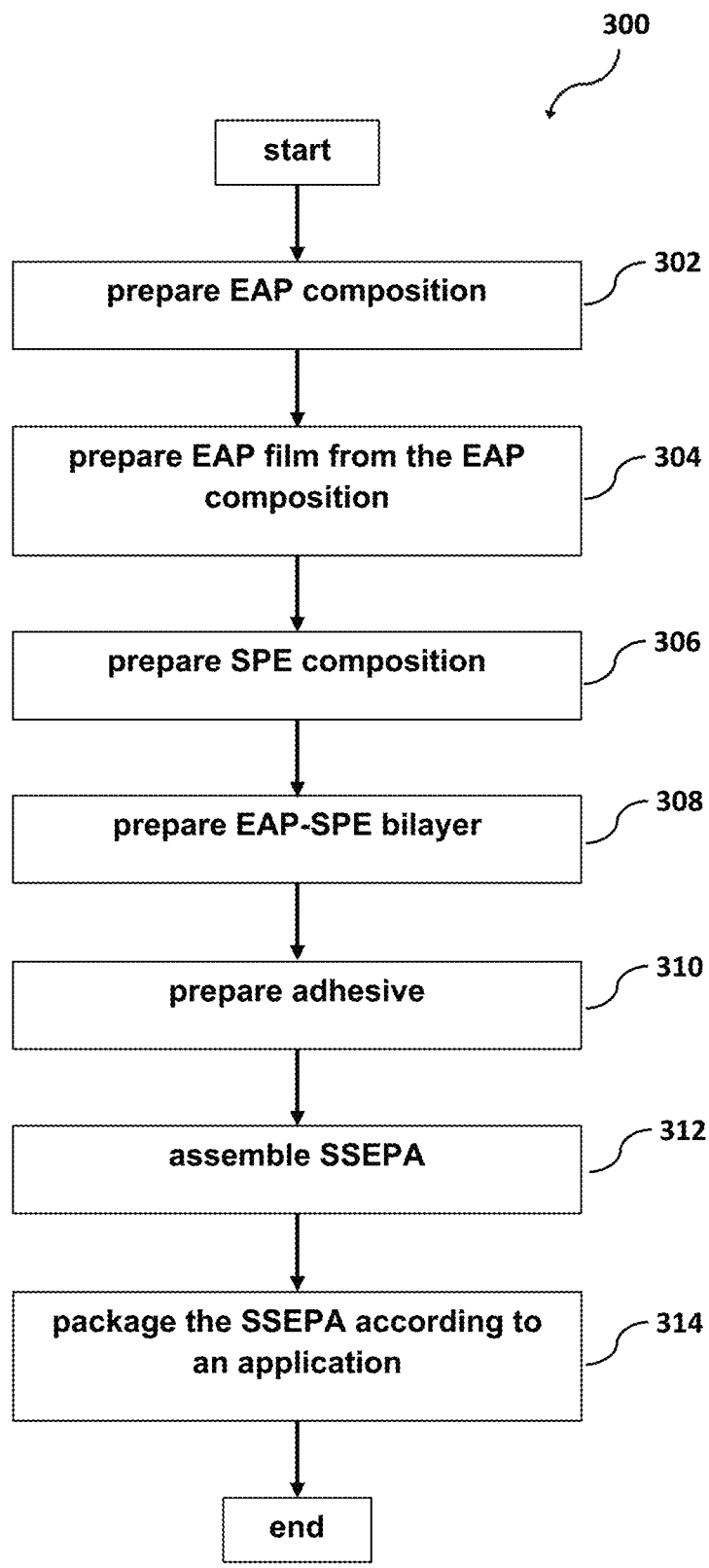
FIG. 3 shows a process flow 300 for fabricating a SSEPA having at least two EAP composition layers and at least one SPE composition layer in accordance with one embodiment of the present technology.

FIG. 3 illustrates a process flow 300 for fabricating a SSEPA in accordance with one embodiment of the present technology. Processes in accordance with the present technology may include up to several additional steps not described or illustrated here in order not to obscure the present technology. In some cases, fabrication processes may include conventional materials and techniques such as commercially available polymers and techniques used in fabrication of polymers, films, devices, etc. It will also be understood by the skilled artisan that in some embodiments the order of steps may be changed from that illustrated here without adversely affecting performance.

The process flow 300 begins with step 302 of preparation of an EAP composition. The EAP composition is generally mixed together using conventional techniques. One example of mixing an EAP composition is given in Example 1 below, however EAP compositions may be prepared using any conventional method known in the art.

In one embodiment, the EAP composition is a mixture of a film-forming polymer (typically about 15-60 wt % of the composition), an electroactive polymer (typically about 5-40 wt % composition), and a plasticizer (typically about 10-40 wt % of the composition). Examples of film-forming polymers include, without limitation, poly(vinyl alcohol) (PVA), polyethylene glycol (PEG), styrene-butadiene rubber (SBR), poly(ethylene-vinyl acetate) (PEVAc), polyvinyl acetate (PVAc), and polyvinylpyrrolidone (PVP). An example of an electroactive polymer includes, without limitation, poly(3,4-ethylenedioxythiophene) polystyrene sulfonate (PEDOT:PSS). Examples of plasticizers include, without limitation, glycerol, polyethylene glycol (PEG), ethylene glycol, N-ethyl toluene sulfonamide, zonyl fluorosurfactant (zonyl), and 4-Dodecylbenzenesulfonic acid (DBSA). In one embodiment, the EAP composition comprises about 25-60 wt % PVA, about 5-40 wt % PEDOT:PSS, and about 10-40 wt % glycerol. In one embodiment, the EAP composition comprises about 15-60 wt % PVA, about 5-40 wt % PEDOT:PSS, and about 10-40 wt % glycerol. In one embodiment, the EAP composition comprises about 25-60 wt % PVA, about 10-40 wt % PEDOT:PSS, and about 10-40 wt % glycerol. In a particular embodiment, the EAP composition comprises about 47 wt % PVA, about 28 wt % PEDOT:PSS, and about 26 wt % glycerol.

In some embodiments, an EAP composition may optionally further comprise 0-50 wt % of a reinforcing filler such as, without limitation, nanocrystalline cellulose (NCC) or clay (e.g., montmorillonite, silicon dioxide ($SiO_2$), or kaolin clay). In alternative embodiments, a reinforcing filler is not included, the film-forming polymer being selected so as to provide sufficient reinforcement in the absence of a separate filler such as NCC or clay. For example, in some embodiments the film-forming polymer is PVAc or PEVAc which provides sufficient reinforcement in combination with the plasticizer N-ethyl toluene sulfonamide to obviate the need for a separate filler such as NCC or clay.

In some embodiments, an EAP composition may optionally further comprise one or more additives selected to provide desirable properties or characteristics, such as without limitation fixatives, rheology modifiers, UV stabilizers, plasticizers, surfactants, emulsifiers, antistatic additives, flame retardants, friction reduction agents, anti-blocking agents, freezing point depressants, IR reflecting agents, lubricants, curing agents, dispersants, solvents, and other additives as are known in the art.

The process flow 300 continues with step 304 of preparation of an EAP film from the EAP composition. In the embodiment shown in FIG. 3 (and described in Example 1 below), the EAP composition is cast on a silicon tray and dried at room temperature for 40 hours to obtain a film thickness of about 250 μm. However, EAP films may be prepared using any conventional method known in the art, such as without limitation casting, solution casting, dipping, spin coating, spraying, compression molding, extrusion and other known processes for fabrication of thin polymer layers. In one embodiment, the EAP film is produced while minimizing variations in thickness or any other defects that may compromise performance. In some embodiments, the EAP film has a thickness of from about 50 μm to about 500 μm, e.g., about 150 μm, 200 μm, 250 μm, 300 μm, or 350 μm. A variety of substrates may be used for preparing the EAP films. For example, EAP films may be cast, spin-coated, or spun etc. on a substrate such as silicone, a smooth non-sticking plastic (e.g., polymethyl methacrylate, teflon), and the like.

The process flow 300 continues with step 306 of preparing a SPE composition. The SPE composition is generally mixed together using conventional techniques. One example of mixing a SPE composition is given in Example 2 below, however SPE compositions may be prepared using any conventional method known in the art.

In one embodiment, the SPE composition is a mixture of a plasticizer (typically about about 20-60 wt % of the composition), a film-forming polymer (typically about 10-60 wt % or about 20-60 wt % or about 15-60 wt % of the composition), and an ionizable salt (typically about 5-25 wt % of the composition). Examples of plasticizers for use in SPE compositions include plasticizers that can dissolve the salt used in the SPE, such as, without limitation, glycerol, polyethylene glycol (PEG), and ethylene glycol. Examples of film-forming polymers for use in SPE compositions include, without limitation, poly(vinyl alcohol) (PVA), polyethylene glycol (PEG), styrene-butadiene rubber (SBR), poly(ethylene-vinyl acetate) (PEVA), polyvinyl acetate (PVAc), polyvinylpyrrolidone (PVP), polyvinylidene fluoride (PVDF), poly(vinylidene fluoride-co-hexafluoropropylene) (PVDF-HFP), polyethylene oxide (PEO), amylopectin, amylose, starch, and combinations thereof. Examples of ionizable salts for use in SPE compositions include, without limitation, lithium perchlorate ($LiClO_4$), lithium bis(trifluoromethanesulfonyl)imide (LiTFSI), lithium polyacrylate (LiPAA), lithium chloride (LiCl), sodium chloride (NaCl), sodium sulfate ($NaSO_4$), sodium nitrate, sodium carbonate, a potassium halide (e.g., potassium chloride, potassium bromide), potassium perchlorate, potassium nitrate, potassium nitrite, potassium ferrocyanide [$K_3Fe(CN)_6$] and potassium ferricyanide [$K_4Fe(CN)_6$].

In some embodiments, a SPE composition may optionally further comprise 0-50 wt % of a reinforcing filler such as, without limitation, nanocrystalline cellulose (NCC) or clay (e.g., montmorillonite, silicon dioxide ($SiO_2$), or kaolin clay). In alternative embodiments, a reinforcing filler is not included, the film-forming polymer being selected so as to provide sufficient reinforcement in the absence of a separate filler such as NCC or clay.

In one embodiment, the SPE composition comprises about 40 wt % glycerol, about 15 wt % starch, about 15 wt % PVA, about 14 wt % $LiClO_4$, about 8.8 wt % NCC and about 7.4 wt % Kaolin clay. In some embodiments, the starch is corn starch.

In some embodiments, a SPE composition may optionally further comprise one or more additives selected to provide desirable properties or characteristics, such as without limitation fixatives, rheology modifiers, UV stabilizers, plasticizers, surfactants, emulsifiers, antistatic additives, flame retardants, friction reduction agents, anti-blocking agents, freezing point depressants, IR reflecting agents, lubricants, curing agents, dispersants, and other additives as are known in the art.

In some embodiments, the SPE compositions are provided in the form of a film. Such films may be made using standard techniques known in the art, such as without limitation casting, solution casting, dipping, spin coating, spraying, compression molding, extrusion, or other known processes for fabrication of thin polymer layers. In one embodiment, the SPE composition is prepared by casting. In a particular embodiment (discussed further elsewhere herein), the SPE composition is preparable or is prepared by extrusion to form a film, e.g., SPE compositions are made using extrusion techniques known in the art such as by using a single or twin screw extruder, e.g., by blown film extrusion, sheet/film extrusion, coextrusion, and the like.

In some embodiments, the SPE composition is provided in the form of a film having a thickness of from about 50 µm to about 500 µm, e.g., about 150 µm, 200 µm, 250 µm, 300 µm, or 350 µm. In some embodiments, the SPE composition is provided in the form of a film having a thickness of from about 100 µm to about 2000 µm.

The process flow 300 continues with step 308 of preparing an EAP-SPE bilayer. In the embodiment shown in FIG. 3 and described in Example 2 below, the SPE composition (prepared in step 306) is cast on top of a pre-dried EAP film (prepared in step 304) for 3 days, to form the EAP-SPE bilayer. However, EAP films may be prepared using any conventional method known in the art, such as without limitation casting, solution casting, dipping, spin coating, spraying, compression molding, extrusion and other known processes for fabrication of thin polymer layers. In one embodiment, the polymer film is produced while minimizing variations in thickness or any other defects that may compromise performance.

Further, EAP-SPE bilayers may be prepared using any conventional method known in the art. For example, an SPE film may first be prepared from the SPE composition using conventional methods (casting, spin-coating, spraying, dipping etc.) on a wide range of substrates (silicone, plastic, teflon etc.), followed by laminating the EAP and SPE films together using conventional techniques (by e.g., adhesive lamination, hot pressing). In such embodiments, one or more of the EAP film and the SPE film may be released from the substrate before lamination with the other film using conventional techniques and reagents. In other embodiments (discussed further below), one or more film may be prepared by extrusion or the EAP and SPE films may be co-extruded together.

The process flow 300 continues with step 310 of preparing an adhesive. In the embodiment shown in FIG. 3 and described in Example 3 below, the adhesive comprises PVA, glycerol, and $LiClO_4$. However, many laminating adhesives are known in the art, and any appropriate adhesive may be used. The choice of adhesive will be determined by the skilled artisan based on the composition of the EAP and SPE films, desired properties and performance characteristics, and other such considerations.

The process flow 300 continues with step 312 of assembling an SSEPA. In the embodiment shown in FIG. 3 and described in Example 3 below, a sufficient amount of adhesive (prepared in step 310) is added to cover the SPE side of the EAP-SPE bilayer (prepared in step 308). The bilayer is then folded (with the adhesive-covered SPE layer on the inside), the assembly is flattened (e.g., with a rolling pin, or the like), and the SSEPA assembly is dried in an oven set at 50-60° C. for 20-30 minutes. In this embodiment, step 312 produces a 3-layer SSEPA 100 having an SPE composition layer sandwiched between two EAP composition layers. In another embodiment, the 3-layer SSEPA 100 produced in step 312 is folded again to produce a 5-layer SSEPA 200; specifically, a sufficient amount of adhesive (prepared in step 310) is added to cover one of the outer EAP layers of the 3-layer SSEPA 100; the 3-layer SSEPA 100 is then folded (with the adhesive-covered EAP layer on the inside), the assembly is flattened, and the SSEPA assembly is dried, producing the 5-layer SSEPA 200. This process can be repeated as many times as desired to make SSEPAs with 7-layers, 9-layers, etc.

It should be understood that the structure of the SSEPA is not meant to be limited, and the number of layers, the configuration of the layers, etc. may all be varied depending on the desired application and properties. Thus many different SSEPA structures may be produced, and SSEPAs may be assembled using a wide range of methods. For example, the 5-layer SSEPA 200 could be produced by adhering two 3-layer SSEPAs 100 together using the adhesive prepared in step 310 (or any other laminating adhesive) (see FIG. 2).

In some embodiments (not depicted), the SSEPA is pre-strained to improve mechanical properties and/or ion mobility. A SSEPA may be pre-strained in one or more directions. In an embodiment, a SSEPA is pre-strained uniaxially. In an embodiment, a SSEPA is pre-strained by mechanically stretching it in one or more directions and fixing it to one or more solid members or substrates while strained. Another technique for maintaining pre-strain includes the use of one or more stiffeners. Stiffeners are generally long rigid structures placed on a polymer while it is in a pre-strained state, e.g., while it is stretched, such that the stiffeners maintain the pre-strain along their axis. Stiffeners may be arranged in parallel or in other configurations to achieve directional compliance of the SSEPA. It should be noted that increased stiffness along the stiffener axis comprises increased stiffness provided by the stiffener material as well as increased stiffness of the polymer in the pre-strain direction. In some embodiments, EAP composition layers and/or SPE composition layers are pre-strained prior to assembly into the SSEPA. For example, a first polymer composition layer may be stretched to the desired pre-strain and then attached to a rigid frame; a second polymer composition layer is then adhered to the first polymer composition layer. Additional polymer composition layers may be attached to additional frames, with the multiple frames stacked together to provide multiple layers. Other permutations are possible. In some embodiments, pre-strain is carried out in two stages: i) during the fabrication of an SSEPA, SPE is pre-stretched using clamps at both ends, and EAP is cast on the pre-stretched SPE; and ii) during electrical analysis, 25 mmHg of pressure is generated by pre-straining the SSEPA. In some embodiments, during the fabrication of an SSEPA, the EAP is pre-stretched using clamps at both ends. Such pre-stretching of the EAP during manufacturing can increase pressure generation of the SSEPA.

In some embodiments, the process flow 300 continues with optional step 314 of packaging the SSEPA assembled in step 312 according to an application. "Packaging" refers to incorporating the SSEPA assembled in step 312 into an electromechanical device or an article of manufacture. Many devices and articles may be made incorporating the SSEPA assembled in step 312, for a wide variety of applications, as discussed further elsewhere herein. Packaging may include assembly of multiple SSEPAs mechanically linked or stacked as multiple layers. In addition, mechanical and electrical connections to the SSEPAs may be formed according to an application.

Figure 4:
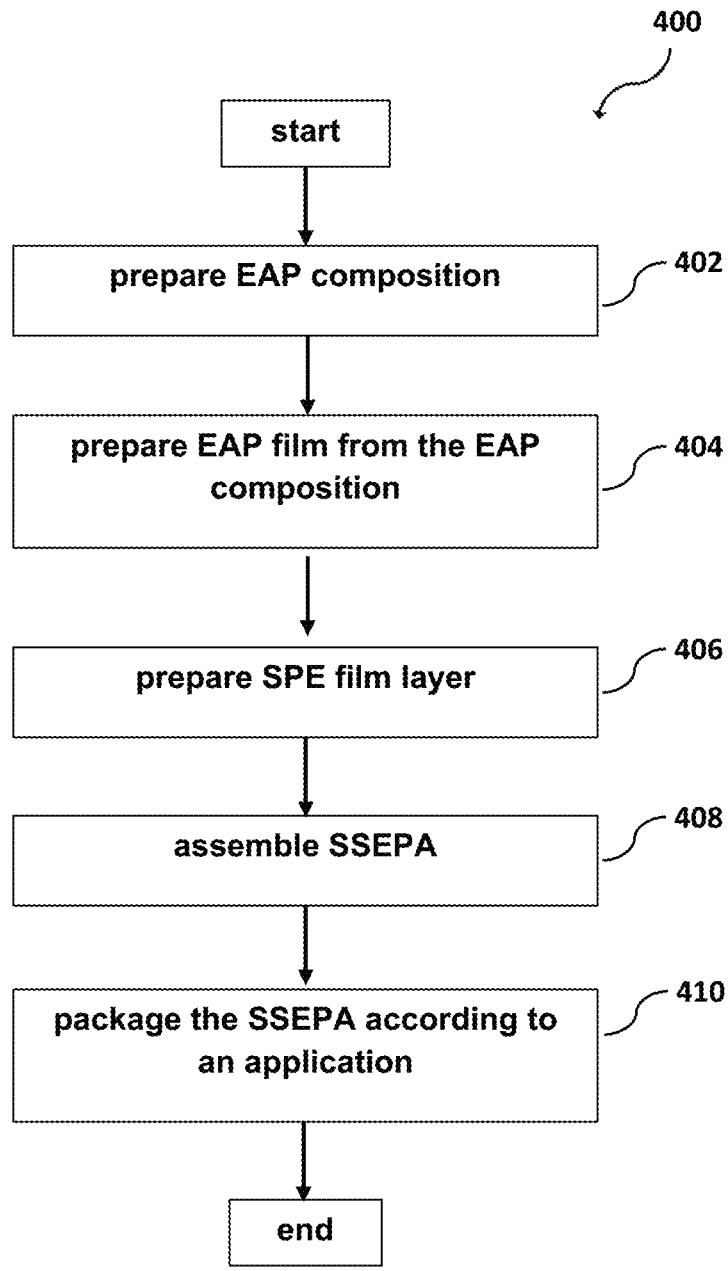
FIG. 4 shows a process flow 400 for fabricating a SSEPA having at least two EAP composition layers and at least one SPE composition layer in accordance with one embodiment of the present technology.

FIG. 4 illustrates a process flow 400 for fabricating a SSEPA in accordance with another embodiment of the present technology. Processes in accordance with the present technology may include up to several additional steps not described or illustrated here in order not to obscure the present technology. In some cases, fabrication processes may include conventional materials and techniques such as commercially available polymers and techniques used in fabrication of polymers, films, devices, etc. It will also be understood by the skilled artisan that in some embodiments the order of steps may be changed from that illustrated here without adversely affecting performance.

The process flow 400 begins with step 402 of preparation of an EAP composition. As detailed above, EAP compositions may be prepared using conventional techniques. In the embodiment described here, the EAP composition is prepared as described for step 302 above although many alternative embodiments are possible.

The process flow 400 continues with step 404 of preparing an EAP film from the EAP composition. As detailed above, EAP films may be prepared using conventional techniques. In the embodiment described here, the EAP film is prepared as described for step 304 above although many alternative embodiments are possible.

In one particular embodiment (not depicted), the EAP composition is prepared using conventional techniques, as described above for steps 302 and 402. The water is then evaporated from the EAP composition (especially if the EAP composition is prepared as a solution with a lot of water) to provide a dry EAP composition. The dry EAP composition is then extruded to make EAP film using a standard extrusion process, such as blown film or film/sheet extrusion.

In another embodiment (not depicted), the EAP composition is provided as a film in one step, i.e., steps 402 and 404 are combined into one step, using extrusion. Using extrusion, the mixture of the EAP composition and preparation of a film thereof are effected in one continuous process, which can be faster and more efficient than a two-step process and/or produce more homogenous films. Conventional extrusion processes known in the art may be used, such as without limitation blown film, film/sheet extrusion, etc.

The process flow 400 continues with step 406 of preparing a SPE film layer. In the embodiment shown here, the SPE composition is provided as a film in one step using extrusion, e.g., blown-film extrusion, sheet/film extrusion, etc. Conventional extrusion processes known in the art may be used. In some embodiments, a SPE film having thickness of about 100-2000 µM is obtained.

The process flow 400 continues with step 408 of assembling a SSEPA 100. In the embodiment shown here, the SPE film prepared in step 406 is sprayed with water to make it sticky, and two EAP films prepared in step 404 are then applied on both sides of the SPE film. The assembly is compressed under a weight and then dried to prepare the SSEPA 100.

In another embodiment (not depicted), the SPE film is placed between two EAP films; the temperature is increased in a hot press (in a temperature range of 50-120° C. for 5-30 minutes); and the three layers are compressed and then cooled down to prepare the SSEPA 100.

In another embodiment of the process flow 400 (not depicted), an assembled SSEPA 100 is produced in one step by co-extruding the three layers.

In some embodiments, the process flow 400 continues with optional step 410 of packaging the SSEPA 100 assembled in step 408 according to an application. The description of step 314 above applies to step 410 here.

Additional information regarding the construction of SSEPAs, their design considerations, and the materials and components that may be employed therein is known in the art and can be found, for example, in U.S. Pat. Nos. 6,249,076; 7,224,106; 7,468,575; 7,671,514; 7,442,760; 7,276,090; 7,595,580; and 8,100,819, each of which is hereby incorporated by reference in its entirety.

Applications and Articles of Manufacture

Solid-state electroactive polymer actuators (SSEPAs) find use in a wide range of applications. Accordingly a wide variety of articles may be produced incorporating SSEPAs described herein.

It should be understood that EAP compositions, SPE compositions, and SSEPAs described herein may be used to convert from electrical to mechanical energy (conventional actuator) or to convert from mechanical to electrical energy (generator). For a device having a substantially constant thickness, one mechanism for differentiating the performance of the device as being an actuator or a generator is in the change in net area orthogonal to the thickness during use. For these devices, when the net area of the device decreases, the device is acting as a generator. Conversely, when the net area of the device increases, the device is acting as an actuator. It should be understood that SSEPAs may be described and shown by focusing on a single direction of energy conversion. More specifically, the present disclosure focuses on converting electrical energy into mechanical energy. However, it is important to note that polymer compositions and SSEPAs may convert between electrical energy and mechanical energy bi-directionally. Thus, any of the polymer compositions and materials, SSEPAs, devices and articles of manufacture described herein are also transducers for converting mechanical energy to electrical energy (a generator) in the reverse direction. Typically, a generator includes a polymer arranged in a manner which causes a change in electric field in response to deflection of a portion of the polymer.

In some embodiments, a SSEPA described herein may be used in a medical device. One example of such a medical device is an artificial sphincter, such as a urethral, an anal, or an esophageal sphincter, based on electroactive polymers under electronic control. For example, an artificial sphincter may comprise a cuff for placement around a body lumen, the cuff comprising one or more SSEPA, and a control unit for electrically controlling the one or more SSEPA to expand or contract the cuff. The SSEPA(s) can be disposed upon one or more substrate layers, and may be provided in numerous configurations on the substrate layers.

Another example of a medical device is an implantable artificial muscle. For example, an artificial muscle patch for implantation adjacent to a patient's heart may be provided, the artificial muscle patch comprising one or more SSEPA, and a control unit for electrically controlling the one or more SSEPAs to expand or contract the artificial muscle patch. The SSEPAs may be provided in numerous configurations on one or more substrate layers. In some embodiments, an artificial muscle may be considered to be an article comprising multiple SSEPAs that are either individually or mechanically linked together and have a single output force and/or displacement. An artificial muscle may be implemented on a micro or macro level and may comprise any one or more of the SSEPAs described herein.

In another embodiment, there are provided organic electroluminescent (OEL) devices and organic light emitting diodes (OLEDs) comprising SSEPAs described herein, useful in electronic media for applications such as backlighting of graphics, pixelated displays, and large emissive graphics.

Non-limiting examples of other devices or articles which may be made incorporating SSEPAs described herein include a wide variety of industrial, medical, consumer, and electronics applications, such as pumps, valves, generators, transducers, sensors, motors, cameras, vibrators, audio speakers, sound generators, printers, optical modulation device, optical switch, extenders, bending beam devices, stacks, diaphragms, and the like.

In some embodiments, a SSEPA described herein may be used in a spacesuit or an anti-gravity suit, for example to provide an electromechanically-assisted space suit glove to assist with finger motion and gripping.

A collection of SSEPAs may be mechanically linked in a device or article of manufacture to form a larger SSEPA with a common output, e.g. force and/or displacement. By using a SSEPA as a base unit in a collection of SSEPAs, conversion of electric energy to mechanical energy may be scaled according to an application. By way of example, multiple linear motion devices may be combined in series in one direction to form a SSEPA having a cumulative deflection of all the linear motion devices in the series. In some embodiments, when transducing electric energy into mechanical energy, multiple SSEPAs may be either individually or mechanically linked in a collection.

In some embodiments, a collection of SSEPAs can be integrated into a medical device to act as an artificial sphincter, an artificial heart, an artificial skeletal muscle or a simulation of a human (e.g., a mannequin-simulator) to replicate muscle and nerve functions for medical training.

In some embodiments, a SSEPA described herein may be used in a garment. For example, a SSEPA described herein may be used in a compression garment, such as without limitation those described in U.S. Patent Application Publication No. 20160120733, the entire contents of which are hereby incorporated by reference. Briefly, a flexible compression garment configured to be worn on at least one body part of a subject may include one or more sensor configured to sense at least one characteristic associated with movement of the subject and/or at least one physiological characteristic of the subject, and one or more SSEPA described herein configured to selectively constrict or selectively dilate the at least one flexible compression garment, in response to a signal from the one or more sensor. The compression garment may further comprise a control system operably coupled to the one or more actuator and the one or more sensor and configured to direct the one or more actuator to selectively constrict or selectively dilate the garment responsive to one or more sensing signal from the one or more sensor. In some embodiments, such selective constriction or dilation can improve muscle functioning or joint functioning during an activity such as a sport, exercise, or other activity. In some embodiments, such compression garments can help relieve pain from muscle stiffness and soreness, and reduce time taken for muscles to repair themselves. Also, when an appropriate amount of compression is used, such compression garments can improve venous return and oxygenation to working muscles.

In some embodiments, the one or more sensor in a compression garment may include one or more of an accelerometer, a pedometer, a counter, a tension sensor, a pressure sensor, a time-keeper, a pulse sensor, a chemical sensor, an oximeter, and/or a temperature sensor.

In some embodiments, a SSEPA described herein may be used in a wearable. As used herein, "wearable" refers to an item which can be worn or placed on a body or body part. For example, a wearable may be an article of apparel, such as without limitation a garment. A wearable may also be an electronically controlled or operated device such as a sensing device, a fitness monitor, and the like. As used herein, the term "garment" refers to an article of apparel configured to be worn or placed on at least one body part of a subject, such as without limitation a flexible compression garment, a compression sleeve, a compression sock, a compression band, etc.

In some embodiments, an article of apparel may be protective gear or sports apparel, such as prosthetic liners, padding for helmets, shoe insoles, and the like, such as without limitation those described in International PCT Patent Application Publication No. WO2017223424, the entire contents of which are hereby incorporated by reference. For example, one or more SSEPA described herein may be used in a prosthetic liner, and potentially as the entire prosthetic liner, in a prosthetic hard socket, in shoe wear, sports gear, protective gear, and military gear, and in compression equipment, to contract and expand in strategic areas as needed, to e.g. maintain a perfect fit, to sense pressure and provide feedback to automatically maintain perfect fit, and/or to attenuate force for an extremely comfortable fit. In some embodiments, there is provided protective gear and sports padding, such as for helmets, including one or more SSEPA described herein. In some embodiments, there is provided protective gear and sports apparel, such as for shoe insoles, including one or more SSEPA described herein. In some embodiments, there are provided prosthetic liners, pads in prosthetic hard sockets, or diagnostics for prosthetic fit, including one or more SSEPA described herein. In some embodiments, there is provided compression equipment, such as compression boots for diabetic patients, military anti-shock trousers (MAST, also called pneumatic antishock garments or PASG) for trauma patients, compression bandages or tapes, and compressive therapies, including one or more SSEPA described herein.

In some embodiments, a SSEPA described herein may be used in a robotic device or system for robot-assisted surgery. For example, one or more SSEPA may be included in a robotic surgical system such as the da Vinci™ Surgical System (Intuitive Surgical, Sunnyvale, CA). In some embodiments, there is provided a robotic device or surgical system comprising one or more SSEPA described herein. An SSEPA may be used, for example, in the end portion of a gripper, a manipulator, or other surgical tool, where it may function as an actuator with built-in sensing properties to provide tactile feedback. In general, a surgical tool for robot-assisted surgery will require at least an actuator for actuating movement of the tool, and an actuator sensor for detecting a movement or position of the actuator. The flexibility, stretchability, and in-built sensing properties of SSEPAs can be advantageous in such tools, e.g., in providing tactile feedback to the user during robot-assisted surgery.

In some embodiments, a SSEPA described herein may be used in an anatomical model for medical or surgical training. For example, a SSEPA may be used to provide an implantable artificial muscle, to mimic muscle movements, to provide artificial skin with sensing capabilities, to produce a color change during certain medical events, and the like in an anatomical model of a human. In some embodiments, there is provided an anatomical model for medical or surgical training comprising one or more SSEPA described herein. In some embodiments, the SSEPA may have electrochromic properties, e.g., it may change color responsive to certain manipulations of the model, providing feedback to the user. For example, when an electrochromic layer is desired, a very thin EAP layer of about 10-50 microns may be applied through spin-coating, with the SSEPA being assembled as described herein.

Performance

SSEPA performance may be characterized in terms of the SSEPA itself, the performance of the SSEPA in a device or article, or the performance of the SSEPA in a specific application. For example, performance of a SSEPA may be described by a performance parameter specific to the SSEPA. By way of example, performance of a SSEPA of a certain size and weight may be quantified by parameters such as stroke or displacement, force, actuator response time, pressure, extension ratio, specific energy density (for a generator), and the like. Alternatively, performance of a SSEPA used for a particular application or incorporated in a particular device or article may be described by a performance parameter specific to the application. Application specific parameters include without limitation stroke or displacement, force, SSEPA response time, frequency response, efficiency, and the like. Such parameters may depend on the size, mass or design of the SSEPA and the particular application, device or article. It should be noted that desirable material properties for a SSEPA may vary depending on the device, article, or application.

Actuation pressure is defined as the change in force per unit cross-sectional area between actuated and unactuated states. In some cases, SSEPAs of the present technology may have an actuation pressure in the range of about 0 to about 100 MPa, or in the range of about 0.1 to about 10 MPa.

Blocking Force is defined as the force applied to an actuator's free end to prevent it from movement upon activation from its fixed end during blocking force measurement (measured as described below in Example 5).

Strength is generally determined based on actuation pressure and blocking force. In some embodiments, SSEPAs provided herein have a blocking force of at least 200 mN, or a blocking force of from about 200 mN to about 1 N, and/or total actuation pressure of about 50 mmHg.

Extension ratio is defined as maximum length to which a polymer or SSEPA can be stretched divided by its original length, and provides a measure of stretchability. In some embodiments, SSEPAs described herein have an extension ratio of 50% or more. In some embodiments, SSEPAs described herein have an extension ratio of 40% or more, 45% or more, 50% or more, 55% or more, 60% or more, 65% or more, or 70% or more.

Stretchability is generally determined based on extension ratio. In some embodiments, SSEPAs provided herein have an extension ratio of from about 20% to about 200%, or of at least about 50%.

Performance of a pre-strained polymer may also be described, independent of polymer size, by efficiency. Electromechanical efficiency is defined as the ratio of mechanical output energy to electrical input energy for an actuator mode of operation or, alternatively, of the ratio of electrical output energy to mechanical input energy for a generator mode of operation.

In some embodiments, SSEPAs described herein have one or more of the following performance characteristics: total force generation of at least 1 N or 30 mmHg; angular displacement of about 60 degrees; extension ratio of 50% or more; and/or actuation pressure in the range of about 0 to about 100 MPa.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1

Preparation of an EAP Composition

An EAP composition comprising 47 wt % PVA, 28 wt % PEDOT:PSS and 26 wt % Glycerol was prepared as follows: 4 grams of poly(vinyl alcohol) (PVA) (MW=146 kg/mol, 99% hydrolysis) were dissolved in 200 mL of water, in a flask kept in an oil bath (oil temperature of 120° C.) for 1 hour. The temperature of the oil bath was then reduced to 85° C. and then 2.2 g of glycerol were added; the mixture was agitated for 15 minutes. Glycerol was used as a plasticizer in this example. The mixture was then cooled to room temperature, to which was then added 200 g of a PEDOT:PSS dispersion (2.4 grams of solids) and stirred for 30 minutes. Finally, the solution was cast on a silicon tray having an area of 475 cm$^2$ and dried at room temperature for 40 hours. The obtained EAP film thickness was about 200±30 μm.

Example 2

Preparation of an SPE Composition by Casting

An SPE composition comprising 40 wt % glycerol, 15 wt % starch, 15 wt % PVA, 14 wt % LiClO$_4$, 8.8 wt % NCC and 7.4 wt % Kaolin clay was prepared by casting as follows: 4.6 grams of starch (4 grams of solids) were mixed in 400 mL of water, in a flask kept in an oil bath (oil temperature of 120° C.) for 1 hour. 2.6 grams of nanocrystalline cellulose (NCC) (2.4 grams of solids) was added to the mixture and stirred for 30 minutes. NCC is used as a reinforcing agent to provide mechanical stability to the SPE film in this example.

4 grams of poly(vinyl alcohol) (PVA) (Mw=146,000, 99% hydrolysis) were then added, followed by mixing for 2 hours until all solid particles were dissolved. Water was periodically added to compensate for evaporation to maintain a volume of about 400 mL. The temperature of the oil bath was reduced to 85° C. and 11 grams of glycerol mixed in 15 mL of water was added. The mixture was stirred for 15 minutes. Glycerol was used as a plasticizer in this example. 3.8 grams of lithium perchlorate ($LiClO_4$) was then added and the mixture was stirred for 15 mins. About 50 mL of water was then added to decrease viscosity of the mixture. 2 grams of Kaolin clay (suspended in 10 mL of water) was then added. The Kaolin clay is a Lewis acid used to enhance the ion mobility of the resultant SPE composition. When the volume of the mixture was about 500 mL or less, the mixture was cast on top of a pre-dried EAP layer (e.g., made as described in Example 1) for 3 days, to form an EAP-SPE bilayer. The obtained SPE thickness was 450±50 µm.

Example 3

SSEPA Assembly Using Glue 10 grams of PVA (MW=146 kg/mol, 99% hydrolysis) was dissolved in 300 mL of water, in a flask kept in an oil bath (oil temperature of 120° C.) for 1 hour. The temperature of the oil bath was reduced to 85° C. and 5.5 grams of glycerol mixed in 15 mL of water was added to the flask. The mixture was stirred for 15 minutes. 2.8 grams of $LiClO_4$ was added, and the mixture was stirred for 15 mins to obtain a glue. A sufficient amount of this glue was added to cover the SPE side of an EAP-SPE bilayer (e.g., formed as described in Example 2). The bilayer was then folded and a rolling pin was used to flatten the assembly. This SSEPA assembly was then dried in an oven set at 60° C. for 30 minutes. The obtained SSEPA thickness was about 1100±100 µm.

Example 4

Preparation of SPE Film by Extrusion and SSEPA Assembly 3.8 grams of $LiClO_4$ were dissolved in 11 grams of glycerol by stirring for 15 minutes at 85° C. 4.6 grams of starch (4 grams of solids), 2.6 grams of NCC (2.4 grams of solids), 4 grams of PVA (MW=146 kg/mol, 99% hydrolysis), and 2 grams of Kaolin clay were added to the mixture. The mixture was poured into a twin-screw extruder with a temperature set at 155° C. and a mixing set at 60 RPM (residence time of 5 minutes). The resulting rubbery mass was compressed under a pressure of 5 MPa and at a temperature of 100 to 150° C. for 10 minutes to obtain an SPE film.

The SPE film was then sprayed with water to make it sticky, and 2 EAP films (e.g., prepared as described in Example 1) were applied on both sides of the extruded SPE film. The assembly was compressed under a heavy flat mass for about an hour. This SSEPA assembly was then dried in an oven set at 60° C. for 30 minutes. The obtained SPE film thickness was about 150-2000 µm. In another method, the SSEPA assembly was made by applying two EAP films on both sides of the extruded SPE film, then compressing the assembly at high temperature to stick the layers together, and then cooling it down.

Example 5

Performance Measurements for SSEPA Assemblies

Figure 5:
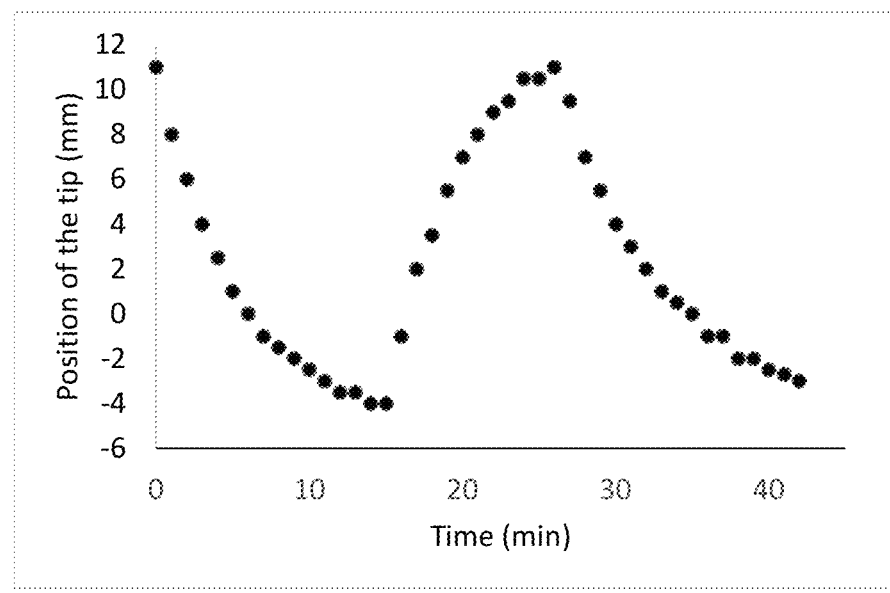
FIG. 5 is a graph showing kinetics of the displacement of the free end of a SSEPA 100 (160×15×1 mm) upon actuation (3 V).

A. SSEPA displacement. An actuator band (an EAP-SPE-EAP trilayer, 160×15×1 mm (length (l)×width (w)×thickness (t)); SSEPA 100) was held, vertically hanging, by a fixed crocodile clip through which DC current was applied (voltage set at 3 V). The position of the free tip of the SSEPA 100 was recorded periodically over a period of up to 15 minutes, until complete displacement was observed. The polarity of the current was then reversed and the measuring process was repeated. Results are shown in FIG. 5, which shows kinetics of the displacement of the free end of SSEPA 100 (160×15×1 mm) upon actuation (3 V).

Figure 6:
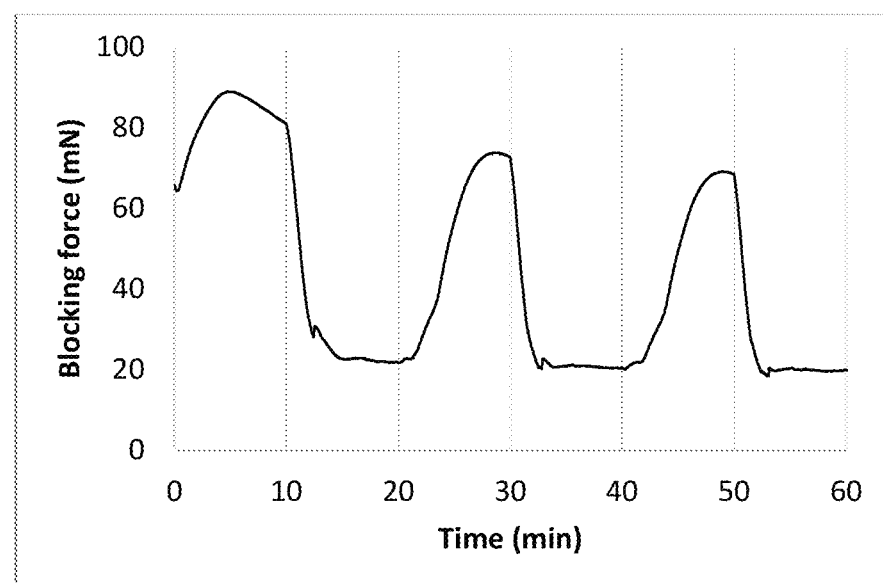
FIG. 6 is a graph showing kinetics of the blocking force generated by a SSEPA 100 (160×15×1 mm) in its center upon application of a 3 V electrical potential (half-cycle time=10 minutes).
Figure 7:
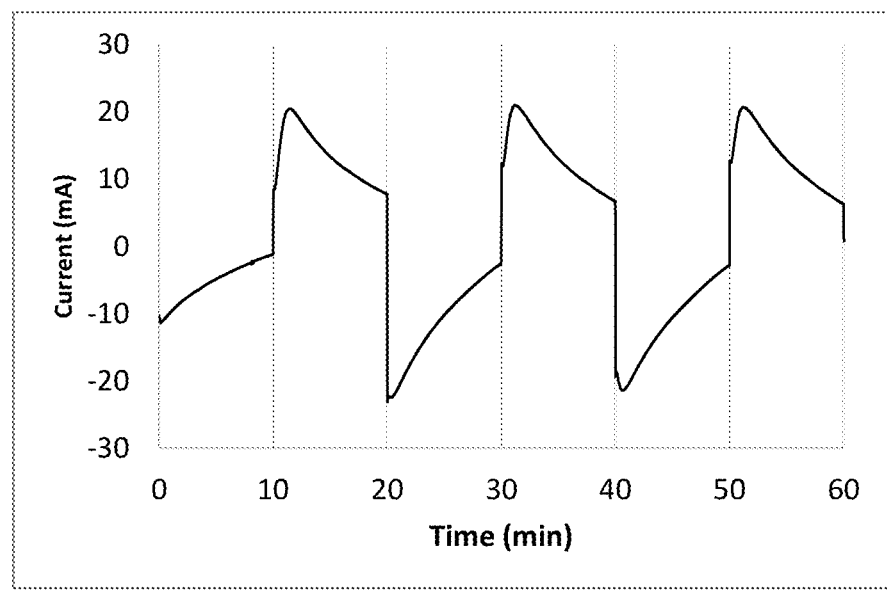
FIG. 7 is a graph showing current flowing through the SSEPA 100 during the blocking force experiment depicted in FIG. 6. Negative current corresponds to current measured during the return half-cycle.

B. Blocking force measurement. An actuator band (an EAP-SPE-EAP trilayer, 160×15×1 mm; SSEPA 100) was placed horizontally on a flat surface and covered with a thin glass interface of about the same length and width. A blocking force sensor was placed directly on the center of the glass interface. The actuator band (SSEPA 100) was held at one end by a crocodile clip through which a 3 volts electrical potential was applied. Upon actuation, the band curved and transferred force to the glass interface and the blocking force sensor, and blocking force was recorded over time. The polarity of the applied electrical potential was periodically reversed and cycles were thus obtained (10 minutes per half-cycle). Results are shown in FIGS. 6 and 7, which show kinetics of the blocking force generated by a SSEPA 100 (160×15×1 mm) in its center upon application of a 3 V electrical potential (half-cycle time of 10 minutes) (FIG. 6) and current flowing through the SSEPA during the blocking force experiment depicted in FIG. 6 (negative current corresponds to current measured during the return half-cycle; FIG. 7).

Figure 8:
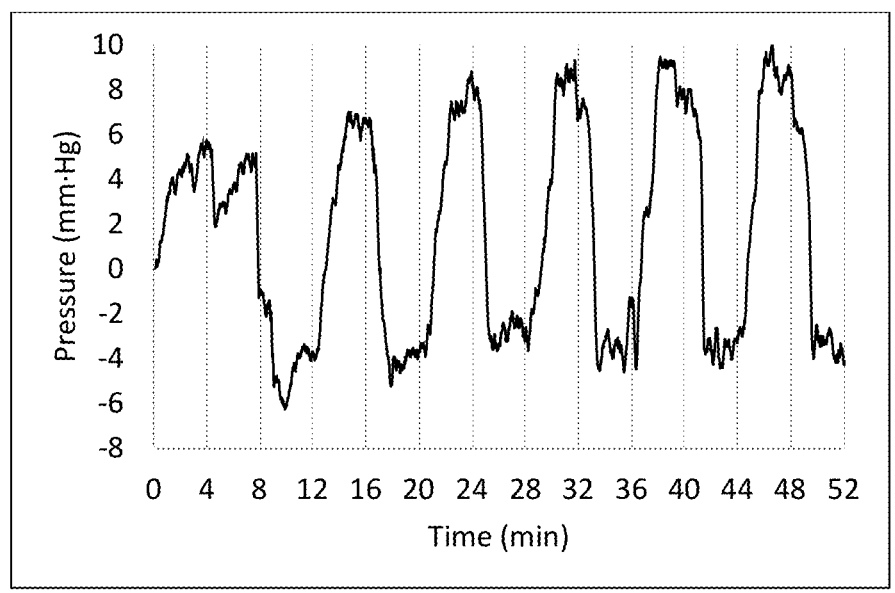
FIG. 8 is a graph showing kinetics of the pressure generated by a SSEPA 100 (160×15×1 mm) in its center (sensor area=2 cm²). Half-cycle time was 4 minutes. Initial pressure or pre-tension corresponded to about 24 mmHg.

C. Pressure measurement. A pressure-imaging mat (Tactilus®, Sensor Products Inc., Madison, New Jersey, www.sensorprod.com) was rolled around a cardboard tube to obtain a pressure-sensitive cylinder. The pressure mat was then covered with stainless-steel coated fabric to shield its electronics from interference from the actuation current. An actuator band (an EAP-SPE-EAP trilayer, 160×15×1 mm; SSEPA 100) was then placed on the pressure mat, perpendicular to the longitudinal axis of the cylinder. The SSEPA 100 was held in place by a Velcro band firmly covering the SSEPA 100 around the cylinder. A slit was cut in the Velcro band through which about 1 cm of the actuator band was stuck out. The protruding section of the SSEPA 100 was clamped by a crocodile clip through which a 3 volts electrical potential was applied. The polarity of the applied electrical potential was periodically reversed and cycles were thus obtained (4 minutes per half-cycle). Results are shown in FIG. 8, which shows kinetics of the pressure generated by a SSEPA 100 (160×15×1 mm) in its center (sensor area=2 $cm^2$) (half-cycle time of 4 minutes; initial pressure or pretension corresponding to about 24 mm·Hg).

D. Extension ratio measurement. A SSEPA 100 sample was placed between the clamps of a universal testing machine (Instron® 5565, Universal Testing Systems 5500 series). The sample was stretched at a rate of 10 mm per minute until sample failure. The reported % extension ratio of the sample corresponds to its maximum length divided by its original length×100.

E. Performance measurements for exemplary SSEPA assemblies. Various SSEPA 100 (3-layer) assemblies were prepared as described in Examples 1-4 and tested. The SSEPA 100 assemblies were as follows:

(1) EAP composition: 47 wt % PVA, 28 wt % PEDOT:PSS, 26 wt % glycerol; SPE composition: 40 wt % glycerol, 15 wt % starch, 15 wt % PVA, 14 wt % LiClO$_4$, 8.8 wt % NCC, 7.4 wt % Kaolin clay. EAP and SPE compositions both prepared as described in Examples 1-3 (casting).
(2) Same as SSEPA #1, but with decreased salt (in SPE) (7 wt % LiClO$_4$ instead of 14 wt % LiClO$_4$). EAP and SPE compositions were both prepared as described in Examples 1-3 (casting).
(3) Same as SSEPA #1, but with increased salt (in SPE) (21 wt % LiClO$_4$ instead of 14 wt % LiClO$_4$). EAP and SPE compositions were both prepared as described in Examples 1-3 (casting).
(4) Same as SSEPA #1, but with a different salt (in SPE) (14 wt % LiPAA instead of 14 wt % LiClO$_4$). EAP and SPE compositions were both prepared as described in Examples 1-3 (casting).
(5) Same as SSEPA #1, but with a different salt (in SPE) (14 wt % LiTFSI instead of 14 wt % LiClO$_4$). EAP and SPE compositions were both prepared as described in Examples 1-3 (casting).
(6) Same as SSEPA #1, but with less plasticizer (in SPE) (20 wt % glycerol instead of 40 wt % glycerol). EAP and SPE compositions were both prepared as described in Examples 1-3 (casting).
(7) Same as SSEPA #6, but with less plasticizer (in EAP) (10 wt % glycerol instead of 26 wt % glycerol). EAP and SPE compositions were both prepared as described in Examples 1-3 (casting).
(8) Same as SSEPA #6, but with more plasticizer (in EAP) (40 wt % glycerol instead of 26 wt % glycerol). EAP and SPE compositions were both prepared as described in Examples 1-3 (casting).
(9) Same as SSEPA #1, but prepared differently. EAP composition was prepared by casting as described in Examples 1-2. SPE composition was prepared by extrusion and the SSEPA 100 was assembled as described in Example 4.
(10) Same as SSEPA #1, but with different SSEPA structure. EAP and SPE compositions were both prepared as described in Examples 1-3 (casting), and two SSEPA 100 were then assembled into a double-stack (SSEPA 200A).
(11) Same as SSEPA #1, but with different preparation and SSEPA structure. EAP composition was prepared by casting as described in Examples 1-2. SPE composition was prepared by extrusion and the SSEPA 100 was assembled as described in Example 4. Two SSEPA 100 were then assembled into a double stack (SSEPA 200A).

Performance measurements for SSEPA assemblies (1)-(11) are given in Table 1.

In addition to measurements given in Table 1, the extension ratio (final length/initial length) was determined for SSEPA (6). The extension ratio for SSEPA (6) was measured to be >400%.

TABLE 1

Performance measurements for exemplary SSEPA assemblies.

| | EAP | | | SPE | | | | | | Blocking | | |
| --- | --- | --- | --- | --- | --- | --- | --- | --- | --- | --- | --- | --- |
| SSEPA Assembly | PVA (wt %) | PEDOT:PSS (wt %) | Glycerol (wt %) | Glycerol (wt %) | Starch (wt %) | PVA (wt %) | LiClO$_4$ (wt %) | NCC (wt %) | Kaolin clay (wt %) | Force (mN) | Displacement (mm) | Pressure (mm · Hg) |
| 1 | 47 | 28 | 26 | 40 | 15 | 15 | 14 | 8.8 | 7.4 | 9-44 (n = 4) | 5-24 (n = 12) | |
| 2 | 47 | 28 | 26 | 43 | 16 | 16 | 7 | 10 | 8 | 9-11 (n = 2) | 10-15 (n = 2) | |
| 3 | 47 | 28 | 26 | 37 | 14 | 14 | 21 | 8 | 7 | 3-39 (n = 3) | 13-22 (n = 4) | |
| 4 | 47 | 28 | 26 | 40 | 15 | 15 | 14[1] | 8.8 | 7.4 | 1-1.2 (n = 2) | 0-3 (n = 2) | |
| 5 | 47 | 28 | 26 | 40 | 15 | 15 | 14[2] | 8.8 | 7.4 | 0-35 (n = 3) | 8-13 (n = 3) | |
| 6 | 47 | 28 | 26 | 19.9 | 19.9 | 19.9 | 18.9 | 11.4 | 10.0 | 78-106 (n = 5) | 10-25 (n = 4) | 0-11 (n = 21) |
| 7 | 57 | 34 | 10 | 40 | 15 | 15 | 14 | 8.8 | 7.4 | 17-37 (n = 4) | 10-15 (n = 2) | |
| 8 | 38 | 23 | 40 | 40 | 15 | 15 | 14 | 8.8 | 7.4 | 4-24 (n = 4) | 10-13 (n = 2) | |
| 9[3] | 47 | 28 | 26 | 40 | 15 | 15 | 14 | 8.8 | 7.4 | 30-50 (n = 4) | 10-23 (n = 4) | 0-11 (n = 10) |
| 10[4] | 47 | 28 | 26 | 40 | 15 | 15 | 14 | 8.8 | 7.4 | 20-28 (n = 2) | | 3-10 (n = 12) |
| 11[5] | 47 | 28 | 26 | 40 | 15 | 15 | 14 | 8.8 | 7.4 | 42-52 (n = 4) | | 5-11 (n = 4) |

[1] LiPAA instead of LiClO$_4$.
[2] LiTFSI instead of LiClO$_4$.
[3] SPE composition layer prepared by extrusion.
[4] SSEPA assembled in a double-stack.
[5] SPE composition layer prepared by extrusion, and SSEPA assembled in a double-stack.

Example 6

Mechanical Extension of SSEPAs

SSEPAs were secured in a universal testing machine (UTM) between two clamps placed 25 mm apart. The distance between the two clamps was increased at a rate of 10 mm per minute until the SSEPA broke. The load placed on the SSEPA to extend it was measured by the instrument.

Figure 9A:
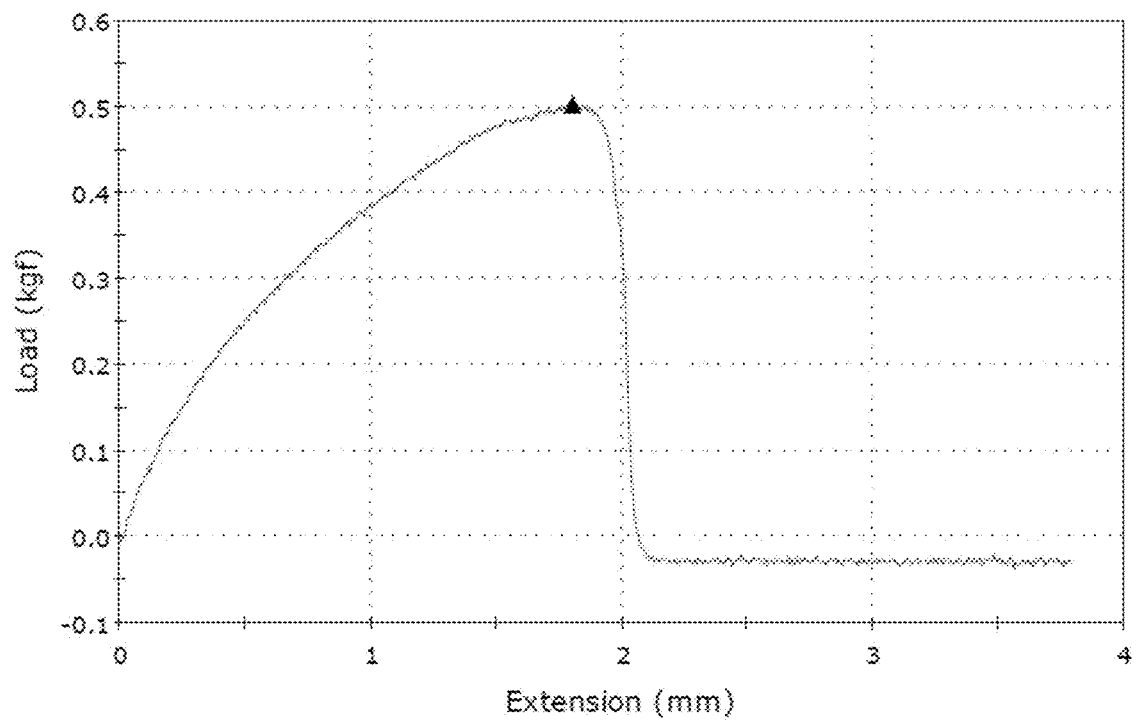
FIGS. 9A-9J are graphs showing load (in kilograms-force) placed on the indicated SSEPA as a function of the extension of the SSEPA (in millimeters). Maximum tensile stress is marked by a triangle. Values for the following measurements are given: a) extension at break (in millimeters), which is the distance by which the SSEPA was stretched at the moment that it broke; b) extension at maximum tensile stress (in millimeters), which is the distance by which the SSEPA was stretched when it reached the greatest tensile stress that it could withstand before deforming. This typically happens just before the actuator breaks; c) load at maximum tensile stress (in kilograms-force), which is the load that was placed on the SSEPA when it reached the greatest tensile stress that it could withstand before deforming; and d) Young's modulus (in kilograms-force per square centimeter), which is a measure of the stiffness of an elastic solid material.

Results are given in FIGS. 9A-9J for the following SSEPAs, as indicated:

FIG. 9A: SSEPA-23: Prepared by coating SPE onto EAP film. EAP: 60.9% PEDOT:PSS+19.5% PVA-Mw-146k+19.5% glycerol; SPE: 66.6% PVA-Mw-146k+14.7% glycerol+18.7% $LiClO_4$.

Figure 9B:
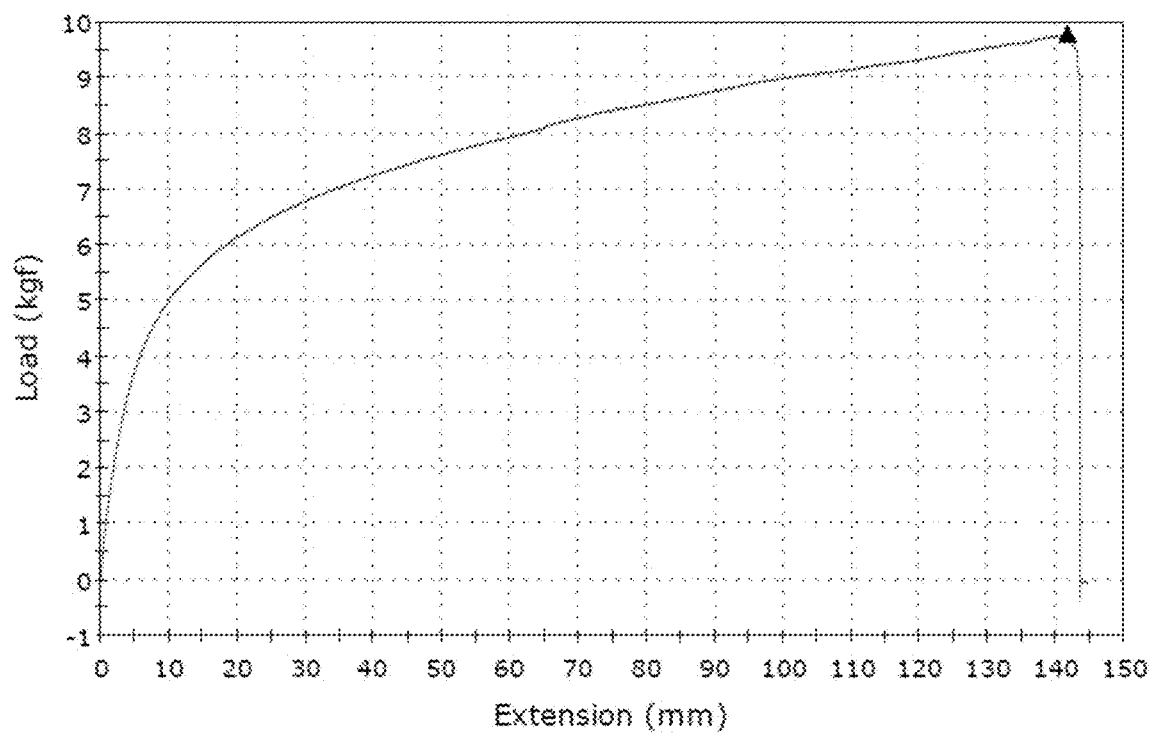

FIG. 9B: SSEPA-24: Prepared by coating SPE onto EAP film. EAP: 14.1% PEDOT:PSS+47.1% PVA-Mw-146k+25.9% glycerol+12.9% $LiClO_4$; SPE: 17.7% corn starch+17.7% PVA+10.6% NCC+28.3% glycerol+16.8% $LiClO_4$+8.8% Kaolin.

Figure 9C:
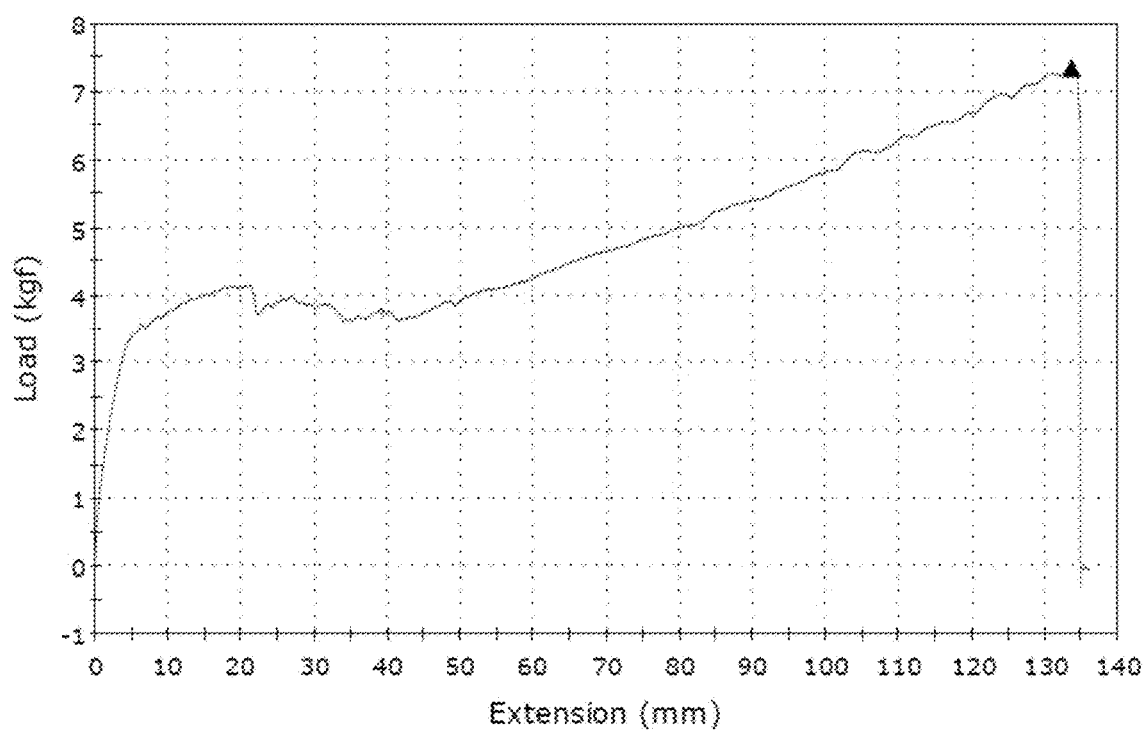

FIG. 9C: SSEPA-20: Prepared by coating EAP onto SPE film. EAP: 75% PEDOT:PSS+25% glycerol; SPE: 21.9% corn starch+12.6% NCC+35% glycerol+20.8% $LiClO_4$+9.8% Kaolin.

Figure 9D:
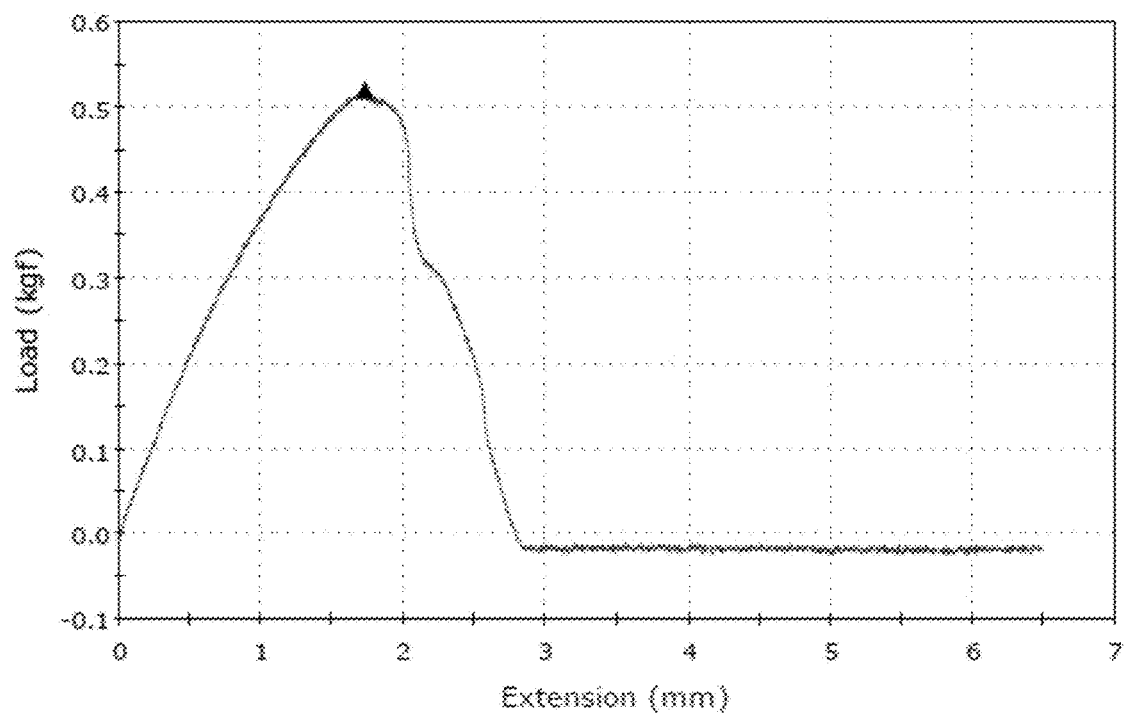

FIG. 9D: SSEPA-22: Prepared by coating EAP onto SPE film. EAP: 50% PEDOT:PSS+16.7% glycerol+16.7% polyvinylpyrrolidone (PVP)-Mw-13000K+16.7% graphene (heXo-G-V20); SPE: 21.9% corn starch+12.6% NCC+35% glycerol+20.8% $LiClO_4$+9.8% Kaolin.

Figure 9E:
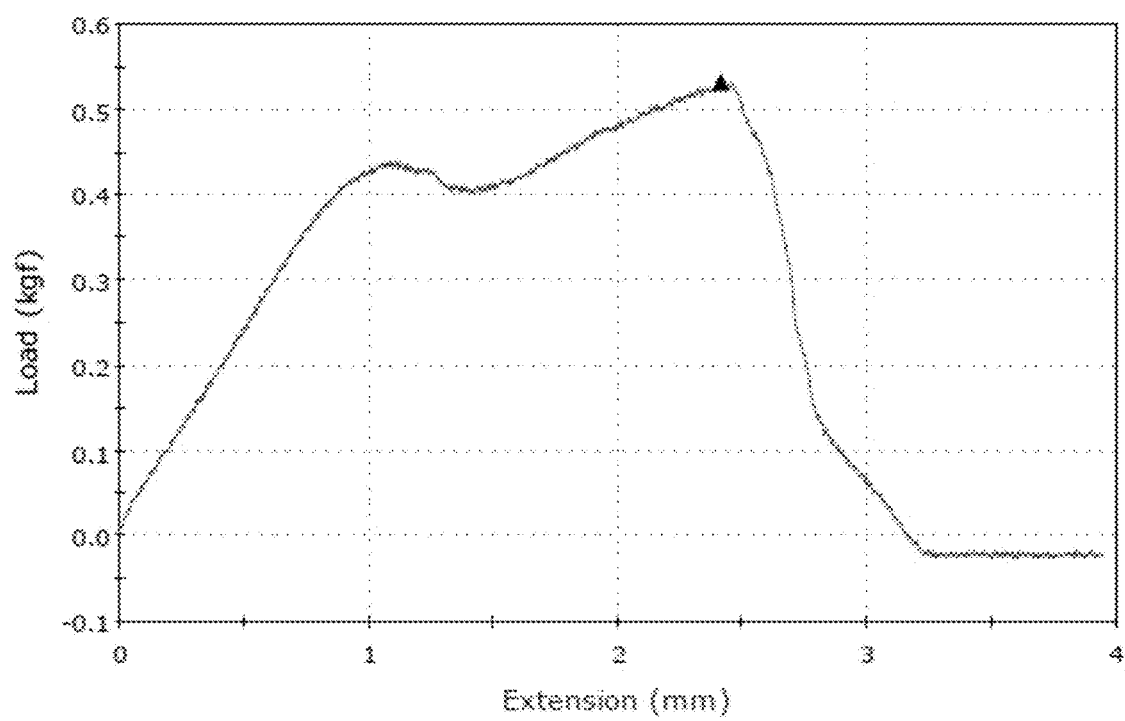

FIG. 9E: SSEPA-22: Prepared by coating EAP onto SPE film. EAP: 50% PEDOT:PSS+16.7% glycerol+16.7% polyvinylpyrrolidone (PVP)-Mw-13000K+16.7% graphene (heXo-G-V20); SPE: 21.9% corn starch+12.6% NCC+35% glycerol+20.8% $LiClO_4$+9.8% Kaolin.

Figure 9F:
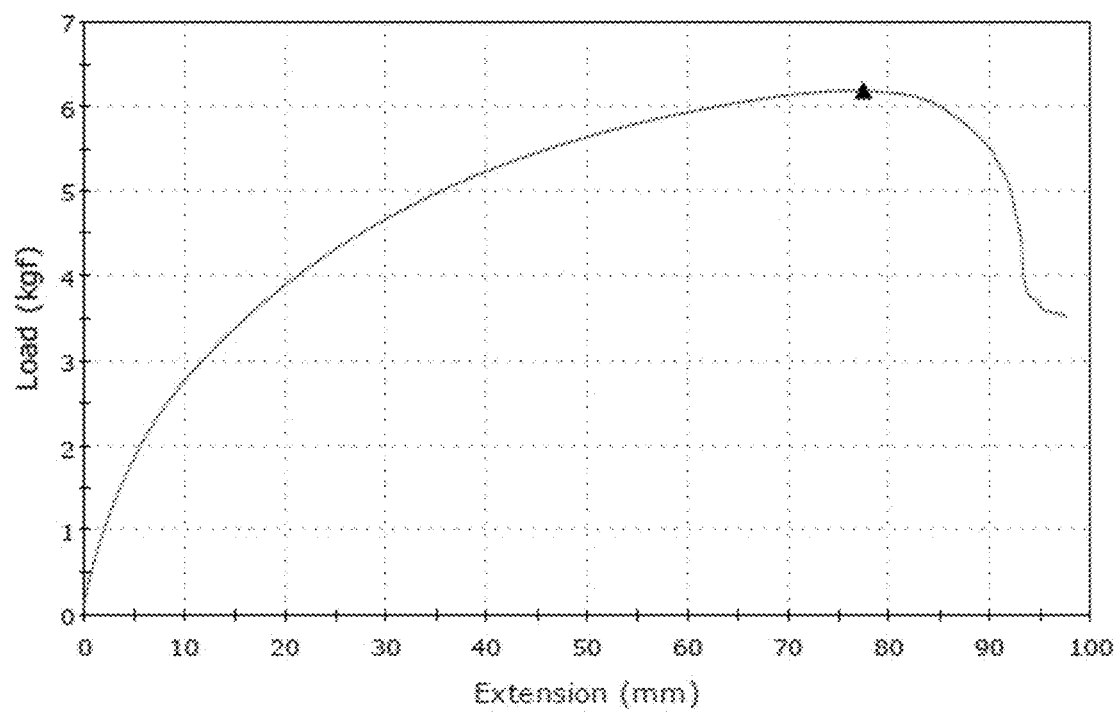

FIG. 9F: SSEPA-25: Prepared by coating SPE onto EAP film. EAP: 27.9% PEDOT:PSS+46.5% PVA-Mw-146k+25.6% glycerol; SPE: 14.7% corn starch+14.7% PVA+8.8% NCC+40.4% glycerol+14% $LiClO_4$+7.4% Kaolin.

Figure 9G:
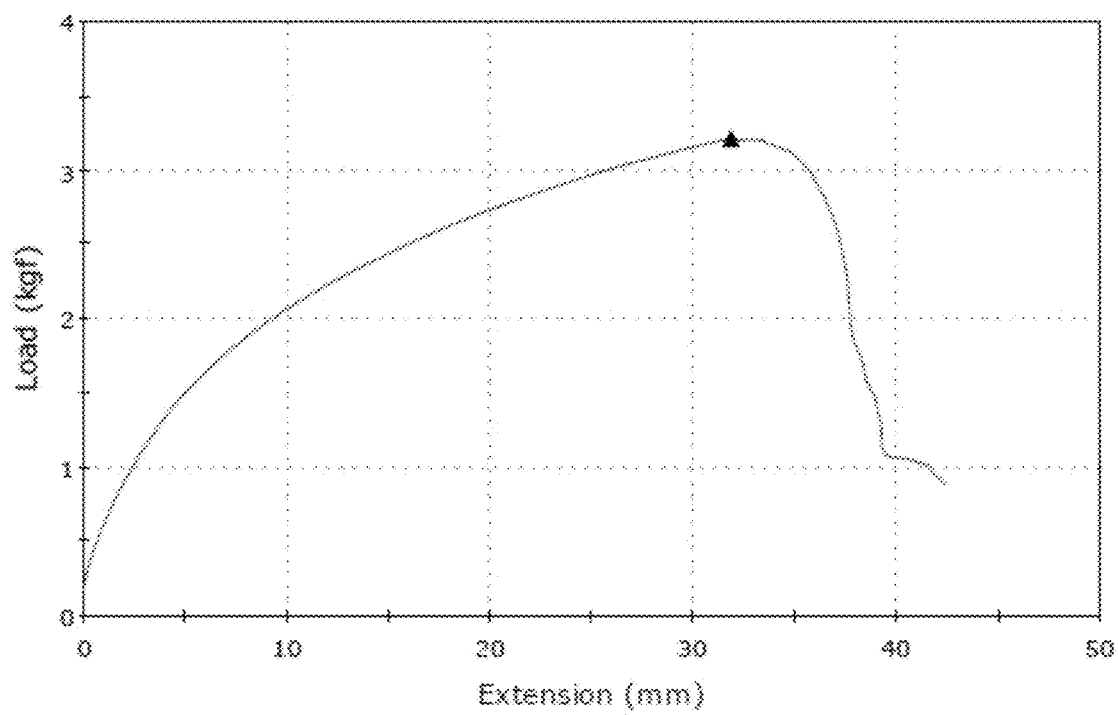

FIG. 9G: SSEPA-26: Prepared by coating SPE onto EAP film. EAP: 42.11% PEDOT:PSS+38.6% PVA-Mw-146k+19.3% glycerol; SPE: 17.7% corn starch+17.7% PVA+10.6% NCC+28.3% glycerol+16.8% $LiClO_4$+8.9% Kaolin.

Figure 9H:
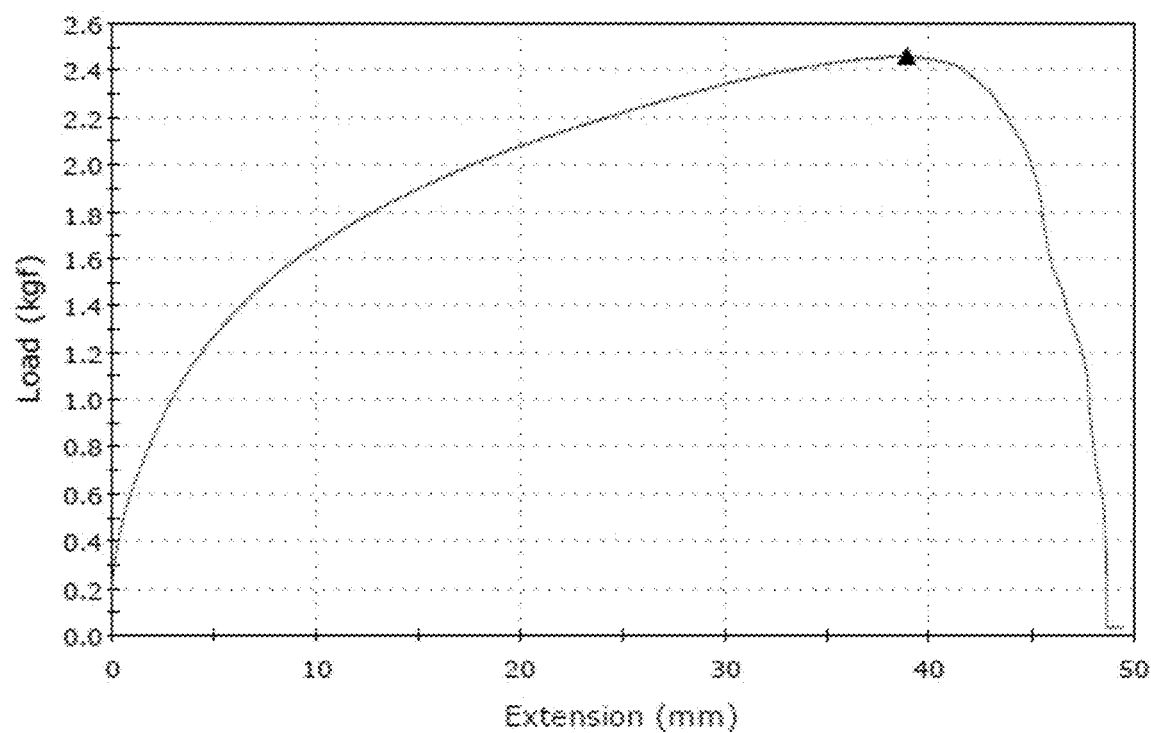

FIG. 9H: SSEPA-27: Prepared by coating SPE onto EAP film. EAP: 27.9% PEDOT:PSS+37.2% PVA-Mw-146k+25.6% glycerol+9.3% PVP-Mw-13,000 k; SPE: 17.7% corn starch+14.2% PVA+3.6% PVP Mw-13,000k+8.8% NCC+28.2% glycerol+16.8% LiClO4+8.9% Kaolin.

Figure 9I:
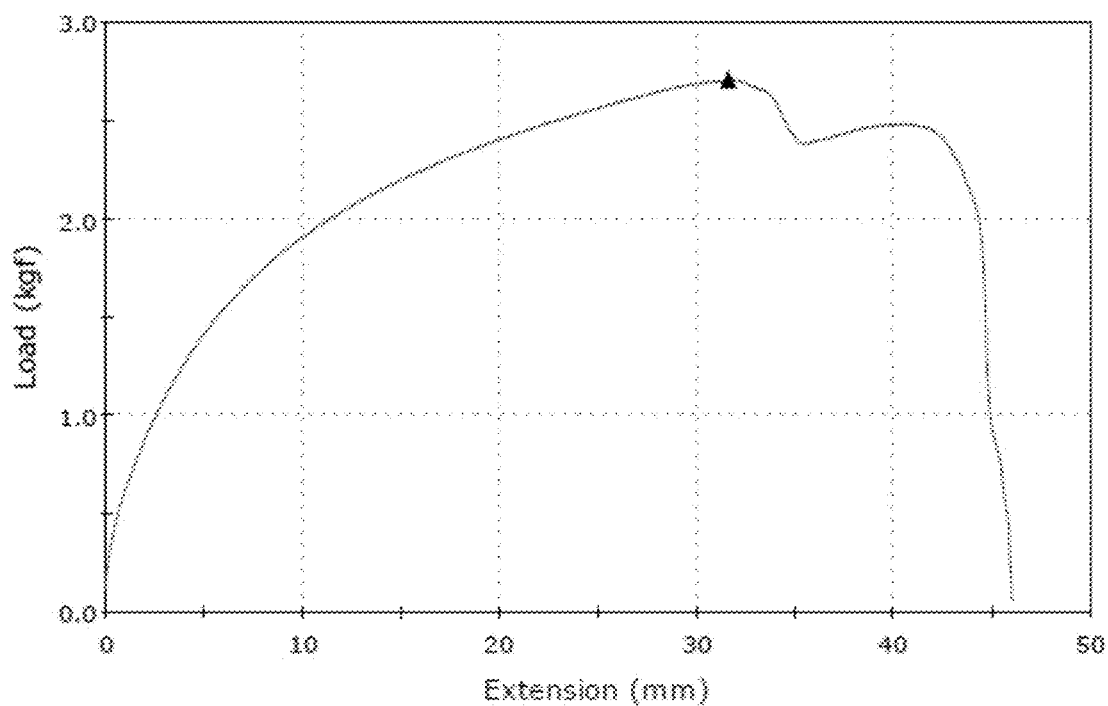

FIG. 9I: SSEPA-28: Prepared by coating SPE multiple times onto EAP film. EAP: 27.9% PEDOT:PSS+46.5% PVA-Mw-146k+25.6% glycerol; SPE: 17.7% corn starch+17.7% PVA+10.6% NCC+28.3% glycerol+16.8% $LiClO_4$+8.9% Kaolin.

Figure 9J:
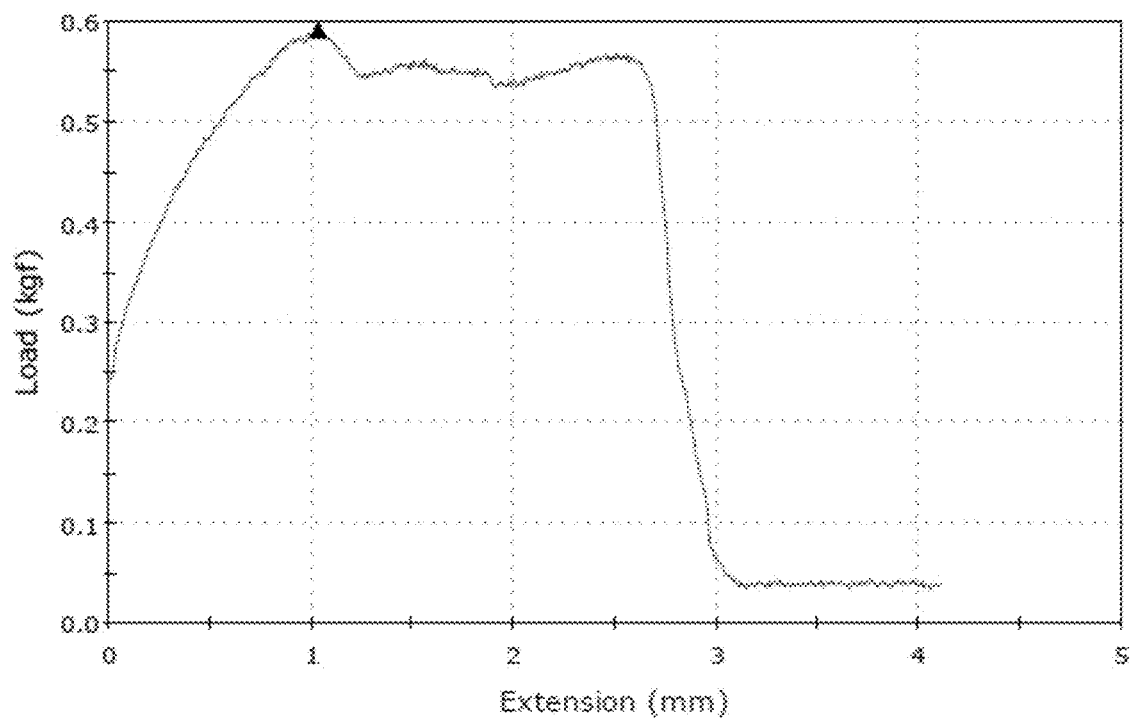

FIG. 9J: SSEPA-21: Prepared by coating EAP onto SPE film. EAP: 60% PEDOT:PSS+20% glycerol+20% polyvinylpyrrolidone (PVP)-Mw-1300k; SPE: 21.9% corn starch+12.6% NCC+35% glycerol+20.8% $LiClO_4$+9.8% Kaolin.

The graphs in FIGS. 9A-9J report the load (in kilograms-force) that was placed on the SSEPA as a function of the extension of the SSEPA (in millimeters). The maximum tensile stress is marked by a triangle. The following properties were measured and are given in the figures for each SSEPA: (a) Extension at break (in millimeters), which is the distance by which the SSEPA was stretched at the moment that it broke; (b) Extension at maximum tensile stress (in millimeters), which is the distance by which the SSEPA was stretched when it reached the greatest tensile stress that it could withstand before deforming. This typically happens just before the SSEPA breaks; (c) Load at maximum tensile stress (in kilograms-force), which is the load that was placed on the actuator when it reached the greatest tensile stress that it could withstand before deforming; and (d) Young's modulus (in kilograms-force per square centimeter), which is a measure of the stiffness of an elastic solid material. Young's modulus was calculated by the UTM's software using the extension and load at maximum tensile stress, and the initial dimensions of the SSEPA.

The results confirm the stretchability and elasticity of the SSEPAs. In general, both extension and load at maximum tensile stress provide important measures of elasticity for actuators. Actuators having a higher extension can be stretched farther without being permanently deformed. Acutators having a higher load require that more force be used to stretch them. Since Young's modulus is derived from both these values and takes into account the thickness of an actuator, it is particularly useful for comparing multiple samples. In general, actuators with a greater Young's modulus are more elastic.

Example 7

Linear Contraction of Asymmetric SSEPAs

Any of the EAP and SPE compositions described herein may be used in the preparation of asymmetric SSEPAs. Additional examples of EAP and SPE compositions for use in SSEPAs of the present technology (asymmetric and symmetric) are given in Tables 2 and 3.

TABLE 2

Exemplary EAP compositions for use in symmetric (e.g., bending) SSEPAs or actuators and/or asymmetric (e.g., linear) SSEPAs or actuators.

| Name | PVA [%] | LiClO$_4$ [%] | Glycerol [%] | PEDOT:PSS [%] | PEG [%] | Other [%] | Other Nature | Other Active Polymer [%] | Other Active polymer Nature | NOTES |
|---|---|---|---|---|---|---|---|---|---|---|
| OSM 91 | 32.4% | 8.9% | 17.8% | 26.3% | | 14.6% | Surfactants | | | Surfactants is 53.3% Span85 and 46.7% Tween 80 in 10 ml H$_2$O |
| SSM 28 | 35.9% | 17.1% | 20.4% | 26.5% | | | | | | |
| SSM 32 | 21.9% | 20.9% | 24.9% | 32.3% | | | | | | |

TABLE 2-continued

Exemplary EAP compositions for use in symmetric (e.g., bending) SSEPAs or actuators and/or asymmetric (e.g., linear) SSEPAs or actuators.

| Name | PVA [%] | LiClO$_4$ [%] | Glycerol [%] | PEDOT:PSS [%] | PEG [%] | Other [%] | Other Nature | Other Active Polymer [%] | Other Active polymer Nature | NOTES |
|---|---|---|---|---|---|---|---|---|---|---|
| SSM 33 | 12.3% | 23.5% | 27.9% | 36.3% | | | | | | |
| SSM 34 | 18.6% | 17.7% | 21.1% | 27.4% | 15.2% | | | | | PEG is PEG 400 |
| SSM 34-b | | 17.7% | 20.9% | 27.7% | 14.5% | 19.1% | | | | other is EVA emulsion +10% benzoate ester plasticizer (total solids = 73%) |
| SSM 34-c | | 17.8% | 21.0% | 20.8% | 14.6% | 25.9% | | | | other is EVA emulsion +10% benzoate ester plasticizer (total solids = 73%) |
| SSM 34-d | | 15.2% | 17.0% | 23.6% | 10.9% | 33.3% | | | | other is EVA emulsion +10% benzoate ester plasticizer (total solids = 73%) |
| SSM 34-e | 4.9% | 16.4% | 19.3% | 26.0% | 13.4% | 20.0% | | | | other is EVA emulsion +10% benzoate ester plasticizer (total solids = 73%) |
| SSM 35 | 13.5% | 17.2% | 20.5% | 26.6% | 22.1% | | | | | PEG is PEG 400 |
| SSM 36 | 18.6% | 17.7% | 21.1% | 27.4% | 15.2% | | | | | PEG is PEG 200k |
| SSM 37 | 18.6% | 17.7% | 21.1% | 27.4% | 7.6% | 7.6% | Hyaluronic Acid | | | PEG is PEG 400 |
| SSM 38 | 20.4% | 9.7% | 23.1% | 30.1% | 16.7% | | | | | PEG is PEG 400 |
| SSM 39 | 16.0% | 15.5% | 18.3% | 23.8% | 26.3% | | | | | PEG is PEG 400 |
| SSM 40 | 18.6% | 17.7% | 21.1% | 27.4% | 7.6% | 7.6% | Hyaluronic Acid | | | PEG is PEO 35k |
| SSM 41 | 16.1% | 15.4% | 18.3% | 23.8% | 19.8% | 6.6% | Hyaluronic Acid | | | PEG is PEG 400 |
| SSM 42 | 13.5% | 17.2% | 20.5% | 22.4% | 23.1% | | | 4.1% | PPY | PEG is PEG 400 |
| SSM 43 | 13.5% | 17.2% | 20.5% | 13.3% | 22.1% | | | 13.4% | PPY | PEG is PEG 400 |
| SSM 44 | 12.8% | 16.3% | 19.5% | 5.1% | 28.1% | | | 25.3% | Solid PEDOT:PSS | PEG is PEG 400 |

TABLE 3

Exemplary SPE compositions for use in symmetric (e.g., bending) SSEPAs or actuators and/or asymmetric (e.g., linear) SSEPAs or actuators.

| Name | PVA [%] | LiClO$_4$ [%] | Glycerol [%] | NCC [%] | Starch [%] | Kaolin [%] | Other [%] | Other Nature |
|---|---|---|---|---|---|---|---|---|
| SS-M-PEG1 | 11.6% | 16.6% | 32.0% | 7.6% | 13.4% | 5.8% | 13.0% | PEG 400 |
| SS-M-AL1 | 12.2% | 17.3% | 33.4% | 7.9% | 14.0% | 6.1% | 9.1% | Al$_2$O$_3$ powder |
| SS-M-04-g | 13.4% | 19.1% | 36.8% | 8.7% | 15.4% | 6.7% | 0.0% | |

Fabrication of an Asymmetric SSEPA.

(i) SPE Film. A mixture of SPE ingredients as the extrusion feed was prepared by dissolving the salt in plasticizer through mixing and heating, followed by adding the two fillers and polymers. The mixture was then extruded to provide a homogenous dispersion of the fillers and polymers. Extruded SPE was then hot-pressed to make the film. Final SPE film thickness was about 0.5 mm.

(ii) EAP Film. EAP film was produced by solution casting method. PVA was dissolved in water and then other ingredients were mixed to provide a uniform solution.

The solution was then cast into a silicon tray and dried at room temperature. The obtained film thickness was about 150 μm.

(iii) Assembly of asymmetric actuator. Asymmetric SSEPAs as shown in FIGS. 10A-B were assembled as follows. First, all the layers were cut to the specific shape and dimensions desired. A stretchable metal fabric was sewed onto the carbon fabric layer to improve the charge distribution. On the EAP side, small carbon fabric pieces with sewed metal fabric were hot pressed at 100° C. for 2.5 min between two Teflon sheets to make the contacts. Finally, a sandwich of metal-carbon fabric/SPE/EAP was hot pressed at 100° C. for about 5 min between Teflon sheets. The prepared actuator was cooled down and removed from the Teflon sheets. (It is noted that during this assembly process, the carbon fabric and the metal fabric are sewn together before being hot-pressed on the SPE).

(iv) Testing of asymmetric actuator. Asymmetric SSEPAs as shown in FIGS. 10A-B were tested. The test setup was as follows:

Energy source: The system was powered by a constant DC current generator. The current was limited to 300 mA per actuator for 1.5 cm wide actuators. Actuators with larger surface area consume proportionally more current. The maximum voltage was limited to 6V.

Pressure sensing: Two different sensing devices were used. In one case, the Tactilus® pressure sensor mattress was wrapped around a rigid cylinder. Actuators were then tightened around it. In the second method, PicoPress® was used to measure the pressure. A plastic bladder with a specific amount of air was placed on a rigid cylinder and the actuators were placed on it and tightened.

Data acquisition: The pressure data was collected using the manufacturer's and in-house developed software for Tactilus® pressure-sensing mat and PicoPress®.

Data processing: The measurements were processed using a Python program developed in-house. The pressure generated over time for each cycle was fitted to a logistic model by non-linear least-squares minimization. The pressure variation for the cycle was extracted from the model's amplitude.

The testing procedure was as follows: Testing of the actuators was done at room temperature and at a normal humidity level maintained in the lab. The following steps were followed to test the actuators on the pressure mat: First, actuators were pre-charged at current and voltage conditions similar to the test for a half-cycle period to position them at their expanded state. Then they were placed on the pressure sensing device and the pressure reading on the testbed was adjusted to near 25 mmHg as the starting point for the test. FIG. 10C shows how actuators were stacked together in specific tests where two actuators were used (stacked actuator assembly). A piece of fabric was placed between the two actuators to isolate them.

Data were recorded starting after pre-charging when EAP layers started to shrink and apply pressure on the sensors. Activation and relaxation cycles followed different patterns. For example, pressure was increased for 15, 30 or 60 seconds, then it was maintained for 5 seconds, followed by pressure decrease for 15, 30 or 60 seconds and a rest time of 5 seconds. In some other tests, the holding and relaxation for 5 seconds was not done.

It is noted that strain ratios of up to 0.4%, up to 1%, up to 2%, or up to 5% can be obtained with asymmetric SSEPAs of the present technology. In contrast to symmetrical SSEPAs described herein (which may bend, for example, 18 degrees from side to side), no bending was observed with asymmetrical SSEPAs. Such asymmetric SSEPAs may have application, for example, for bracing and/or for tightening for prosthetic, orthotic and gripping applications.

Compositions of exemplary actuators used for Tactilus® pressure-sensing mat and PicoPress® measurements are shown in Table A.

TABLE A

Compositions used for pressure-sensing mat and PicoPress® measurements.

| Name | EAP | SPE |
| --- | --- | --- |
| BM 1.01 | SSM 28 | SS-M-04-g_500 |
| BM 1.02 | SSM 28 | SS-M-04-g_500 |
| BM 1.03 | SSM 32 | SS-M-04-g_500 |
| BM 1.04 | SSM 33 | SS-M-04-g_500 |
| BM 1.05 | SSM 28 | SS-M-04-g_500 |
| BM 1.06 | | SS-M-04-g_500 |
| BM 1.07 | SSM 34 | SS-M-PEG1 |
| BM 1.08 | SSM 34 | SS-M-04-g_500 |
| BM 1.09 | SSM 28 | SS-M-04-g_500 |
| BM 1.10 | SSM 28 | SS-M-04-g_150 |
| BM 1.11 | SSM 34 | SS-M-04-g_500 |
| BM 1.12 | SSM 28 | SS-M-04-g_500 |
| BM 1.13 | SSM 28 | SS-M-04-g_500 |
| BM 1.14 | SSM 28 | SS-M-04-g_500 |
| BM 1.15 | SSM 28 | SS-M-AL1 |
| BM 1.16 | SSM 28 | SS-M-04-g_250 |
| BM 1.17 | SSM 28 | SS-M-04-g_500 |
| BM 1.18 | SSM 28 | SS-M-04-g_500 |
| BM 1.19 | SSM 28 | SS-M-04-g_500 |
| BM 1.20 | SSM 28 | SS-M-04-g_500 |
| BM 1.21 | SSM 28 | SS-M-04-g_500 |
| BM 1.22 | SSM 28 | SS-M-04-g_500 |
| BM 1.23 | SSM 36 | SS-M-04-g_500 |
| BM 1.24 | SSM 34.2 | SS-M-04-g_500 |
| BM 1.25 | SSM 34 | SS-M-04-g_500 |
| BM 1.26 | SSM 34 | SS-M-04-g_500 |
| BM 1.27 | SSM 33 | SS-M-04-g_500 |
| BM 1.28 | SSM 35 | SS-M-04-g_500 |
| BM 1.29 | SSM 36 | SS-M-04-g_500 |
| BM 1.30 | SSM 35 | SS-M-04-g_500 |
| BM 1.31 | SSM 36 | SS-M-04-g_500 |
| BM 1.32 | SSM 37 | SS-M-04-g_500 |
| BM 1.33 | SSM 37 | SS-M-04-g_500 |
| BM 1.34 | SSM 38 | SS-M-04-g_500 |
| BM 1.35 | SSM 39 | SS-M-04-g_500 |
| BM 1.36 | SSM 35.3 | SS-M-04-g_500 |
| BM 1.37 | SSM 35.3 | SS-M-04-g_500 |
| BM 1.38 | SSM 34.2 | SS-M-04-g_500 |
| BM 1.39 | SSM 34.2 | SS-M-04-g_500 |
| BM 1.40 | SSM 40 | SS-M-04-g_500 |
| BM 1.41 | SSM 40 | SS-M-04-g_500 |
| BM 1.42 | SSM 36 | SS-M-04-g_500 |
| BM 1.43 | SSM 36 | SS-M-04-g_500 |
| BM 1.44 | SSM 34 | SS-M-04-g_500 |
| BM 1.45 | SSM 34.2 | SS-M-04-g_200 |
| BM 1.46 | SSM 37 | SS-M-04-g_500 |
| BM 1.47 | SSM 37 | SS-M-04-g_500 |
| BM 1.48 | SSM 34.2 | SS-M-04-g_500 |
| BM 1.49 | SSM 34 | SS-M-04-g_500 |
| BM 1.50 | SSM 35.5 | SS-M-04-g_500 |
| BM 1.51 | SSM 35.5 | SS-M-04-g_500 |
| BM 1.52 | SSM 34.2 | SS-M-04-g_500 |
| BM 1.53 | SSM 34 | SS-M-04-g_500 |
| BM 1.54 | SSM 34 | SS-M-04-g_500 |
| BM 1.55 | SSM 35.5 | SS-M-04-g_200 |
| BM 1.56 | SSM 35.5 | SS-M-04-g_500 |
| BM 1.57 | SSM 41 | SS-M-04-g_500 |
| BM 1.58 | SSM 42 | SS-M-04-g_500 |
| BM 1.59 | SSM 43 | SS-M-04-g_500 |
| BM 1.60 | SSM 44 | SS-M-04-g_500 |
| BM 1.61 | SSM 37 | SS-M-04-g_500 |
| BM 1.62 | SSM 35.5 | SS-M-04-g_500 |
| BM 1.63 | SSM 35.5 | SS-M-04-g_500 |
| BM 1.64 | SSM 35.5 | SS-M-04-g_500 |
| BM 1.65 | SSM 35.5 | SS-M-04-g_500 |

TABLE A-continued

Compositions used for pressure-sensing mat and PicoPress ® measurements.

| Name | EAP | SPE |
|---|---|---|
| BM 1.66 | SSM 35.5 | SS-M-04-g_500 |
| BM 1.67 | SSM 35.4 | SS-M-04-g_500 |
| BM 1.68 | SSM 35.4 | SS-M-04-g_500 |
| BM 1.69 | OSM 91 | SS-M-04-g_500 |
| BM 1.70 | SSM 34-c | SS-M-04-g_500 |
| BM 1.71 | SSM 34-b | SS-M-04-g_500 |
| BM 1.72 | SSM 34-b | SS-M-04-g_500 |
| BM 1.73 | SSM 35.5 | SS-M-04-g_500 |
| BM 1.74 | SSM 35.5 | SS-M-04-g_500 |
| BM 1.75 | SSM 34-b | SS-M-04-g_500 |
| BM 1.76 | SSM 35.5 | SS-M-04-g_500 |
| BM 1.77 | SSM 35.4 | SS-M-04-g_500 |
| BM 1.78 | SSM 34.2 | SS-M-04-g_500 |
| BM 1.79 | SSM 34-d | SS-M-04-g_500 |
| BM 1.80 | SSM 34-e | SS-M-04-g_500 |
| BM 1.81 | SSM 35.4 | SS-M-04-g_500 |
| BM 1.82 | SSM 35.6 | SS-M-04-g_500 |
| BM 1.83 | SSM 35.6 | SS-M-04-g_500 |
| BM 1.84 | SSM 35.6 | SS-M-04-g_500 |
| BM 1.85 | SSM 35.6 | SS-M-04-g_500 |
| BM 1.86 | SSM 34.2 | SS-M-04-g_500 |
| long 1 | SSM 35.5 | SS-M-04-g_500 |
| long 2 | SSM 34.2 | SS-M-04-g_500 |
| long2 | SSM 35.4 | SS-M-04-g_500 |
| MAS01 | SSM 35.2 | SS-M-04-g_500 |
| MAS02 | SSM 35.2 | SS-M-04-g_500 |
| MAS03 | SSM 35.3 | SS-M-04-g_500 |
| MAS04 | SSM 35.3 | SS-M-04-g_500 |
| MAS05 | SSM 35.3 | SS-M-04-g_500 |
| MAS06 | SSM 35.3 | SS-M-04-g_500 |
| MAS07 | SSM 35.2 | SS-M-04-g_500 |
| MAS08 | SSM 35.2 | SS-M-04-g_500 |
| panel 1 | SSM 35.5 | SS-M-04-g_500 |
| panel 2 | SSM 35.5 | SS-M-04-g_500 |
| SnapStack1 | SSM 35.4 | SS-M-04-g_500 |
| wide 1 | SSM 34.2 | SS-M-04-g_500 |
| wide2 | SSM 35.5 | SS-M-04-g_500 |
| WideSnapStack1 | SSM 35.4 | SS-M-04-g_500 |
| BM 1.87 | SSM 34.2 | SS-M-04-g_500 |
| BM 1.88 | SSM 34 f | SS-M-04-g_500 |
| wide3 | SSM 35.6 | SS-M-04-g_500 |
| BM 1.89 | SSM 34-e | SS-M-04-g_500 |
| wide4 | SSM 34.2 | SS-M-04-g_500 |
| wide5 (18% stretched EAP) | SSM 35.6 | SS-M-04-g_500 |
| wide6 (15% stretched EAP) | SSM 32 | SS-M-04-g_500 |
| wide7 | SSM 35 | SS-M-04-g_500 |
| wide8 | SSM 38 | SS-M-04-g_500 |
| wide9 (8% stretched EAP) | SSM 38 | SS-M-04-g_500 |
| wide10 (9% stretched EAP) | SSM 38 | SS-M-04-g_500 |
| Wide11 (25% stretched EAP) | SSM 32 | SS-M-04-g_500 |
| Wide 13 | SSM 53 | SS-M-04-g_500 |
| Wide 14 (15% stretched EAP) | SSM 37 | SS-M-04-g_500 |
| Wide 15 (22.5% stretched EAP) | SSM 32 | SS-M-04-g_500 |
| Wide18 (23% stretched EAP) | SSM 32 | SS-M-04-g_500 |

Data collected using the PicoPress® is shown in Table B.

TABLE B

Data collected using the PicoPress.

| Experiment | Description | Cycles | Cycle length (s) | Current Avg (mA) | Voltage Avg (V) | PicoPress Avg (mmHg) | PicoPress Max (mmHg) | PicoPress StD (%) |
|---|---|---|---|---|---|---|---|---|
| 18 | wide3 | 32 | 40 | 377.43 | 4.06 | 5.32 | 8.4 | 30.38 |
| 19 | Wide3 | 3 | 40 | 229.03 | 7.41 | 1.7 | 1.9 | 20.38 |
| 23 | BM187 | 7 | 40 | 89.29 | 6.32 | 1.7 | 1.8 | 3.4 |
| 24 | BM187 | 10 | 40.1 | 78.6 | 6.32 | 1.17 | 1.2 | 4.13 |
| 34 | BM-190 | 10 | 40 | 99.32 | 6.18 | 3.34 | 4.4 | 16.35 |
| 61 | wide-4 | 9 | 70 | 359.37 | 4.06 | 6.62 | 7.4 | 5.54 |
| 62 | wide-5 | 10 | 70 | 294.04 | 6.2 | 5.63 | 6.5 | 10.85 |
| 63 | wide-5 | 10 | 70 | 305.77 | 6.13 | 5.09 | 5.3 | 3.98 |
| wide-4 | wide-4 | 7 | 70 | 422.11 | 3.09 | 2.67 | 4 | 24.52 |
| 65 | wide-5 | 13 | 70 | 715.29 | 3.78 | 3.12 | 3.7 | 6.53 |
| 68 | wide-4 with rigid backing | 2 | 70.1 | 659.76 | 5.56 | 5.05 | 5.1 | 1.4 |
| 69 | wide-4 | 2 | 70.1 | 716.28 | 3.55 | 2.55 | 2.8 | 13.86 |
| 70 | wide-4 | 1 | 69.9 | 715.34 | 3.69 | 2.2 | 2.2 | |
| 71 | wide-4 | 2 | 70.1 | 355.44 | 4.48 | 7.35 | 7.7 | 6.73 |
| 72 | wide-4 | 6 | 70 | 480.05 | 4.67 | 5.9 | 6.1 | 2.84 |
| 77 | Wide5 | 11 | 70 | 303.29 | 6.36 | 8.75 | 9.1 | 3.17 |
| 78 | wide5 | 10 | 40 | 272.48 | 6.33 | 4.93 | 5.2 | 4.17 |
| 79 | wide5 | 9 | 70 | 369.78 | 6.34 | 10.11 | 11.1 | 4.03 |
| 80 | wide4 wide5 fold on length | 7 | 70 | 799.9 | 4.38 | 6.01 | 7 | 8.17 |
| 81 | wide-7 with rigid backing | 7 | 70 | 612.52 | 5.85 | 8.5 | 10.2 | 10.26 |
| 82 | wide-7 | 10 | 70 | 643.64 | 5.76 | 8.39 | 10 | 8.55 |
| 83 | wide-6 | 11 | 70 | 413.64 | 5.48 | 9.47 | 11 | 7 |
| 84 | wide8 | 10 | 70 | 360.54 | 3.84 | 6.34 | 7.9 | 10.39 |
| 85 | wide9 | 11 | 70 | 360.82 | 3.61 | 8.59 | 10.1 | 7.26 |
| 86 | wide10 | 20 | 70 | 360.49 | 4.46 | 6.67 | 7.4 | 3.15 |
| 87 | Wide 10 repeatability | 19 | 70 | 365.85 | 3.96 | 8.67 | 9.4 | 2.55 |
| 88 | Wide 8 repeatability | 19 | 70 | 360.43 | 3.45 | 5.99 | 7.2 | 6.56 |
| 89 | Wide 9 repeatability | 21 | 70 | 360.57 | 3.28 | 8.94 | 10.2 | 4.47 |
| 90 | Wide 10 repeatability | 12 | 70 | 438.08 | 4.91 | 10.28 | 11.5 | 5.14 |
| 92 | Wide 9 repeatability | 11 | 70 | 441.68 | 3.01 | 7.95 | 8.8 | 4.11 |
| 92 | Wide 9 repeatability | 10 | 70 | 159.49 | 5.02 | 4.66 | 5.7 | 9.87 |
| 93 | wide 11 | 12 | 70 | 690.48 | 6.15 | 11.83 | 13 | 3.5 |

TABLE B-continued

Data collected using the PicoPress.

| Experiment | Description | Cycles | Cycle length (s) | Current Avg (mA) | Voltage Avg (V) | PicoPress Avg (mmHg) | PicoPress Max (mmHg) | PicoPress StD (%) |
|---|---|---|---|---|---|---|---|---|
| 94 | wide 11 | 12 | 70 | 671.75 | 6.15 | 15.22 | 15.5 | 0.89 |
| 97 | wide 7 repeatability | 9 | 70 | 482.33 | 6.19 | 5.12 | 5.3 | 2.13 |
| 98 | wide 11 repeatability with rigid backing | 5 | 70 | 806.47 | 5.57 | 5.4 | 11.2 | 68.39 |
| 99 | wide 11 repeatability | 10 | 70 | 803.75 | 5.62 | 4.69 | 5 | 5.17 |
| 103 | wide 11 on blue foam without rigid back | 8 | 70 | 740.75 | 6.18 | 7.71 | 8.3 | 3.28 |
| 106 | wide 13 | 11 | 70 | 497.86 | 6.01 | 6.45 | 9.2 | 17.52 |
| 108 | wide 13 | 10 | 70 | 541.84 | 5.39 | 6.53 | 8.7 | 13.19 |
| 109 | wide 14 | 10 | 70 | 352.37 | 6.31 | 9.4 | 12.7 | 16.6 |
| 111 | wide 14 pivot | 5 | 68 | 370.23 | 6.21 | 9.5 | 9.7 | 1.97 |
| 112 | wide 14 pivot 2 | 3 | 70.1 | 368.27 | 5.96 | 8.27 | 9.1 | 8.75 |
| 113 | wide 14 pivot3 | 3 | 70 | 410.11 | 6.17 | 10.9 | 12.2 | 10.42 |
| 114 | wide14 pivot4 | 4 | 70 | 383.48 | 6.24 | 10.68 | 11.3 | 4.07 |
| 126 | wide14 test of repeatability | 44 | 70 | 424.09 | 5.69 | 9.04 | 13.2 | 14.58 |
| 127 | wide11 with rigid backing | 3 | 70 | 483.7 | 6.18 | 6.73 | 7 | 3.43 |
| 128 | wide15 | 11 | 70.1 | 1001.55 | 5.33 | 14.98 | 16.4 | 4.17 |
| 129 | wide15 with rigid backing | 4 | 70.1 | 995.43 | 5.49 | 9.8 | 10.2 | 3.44 |
| 130 | wide15 with rigid backing | 15 | 70 | 1003.62 | 5.3 | 13.43 | 13.6 | 0.67 |
| 130 | wide15 with rigid backing | 8 | 70 | 996.57 | 5.61 | 12.59 | 14.2 | 5.91 |
| 135 | wide15 test repeatability | 10 | 70 | 1004.65 | 4.61 | 15.26 | 15.4 | 0.55 |
| 136 | wide15 (9.5 cm) bladder at lower edge | 11 | 70 | 990.53 | 5.56 | 12.75 | 13 | 1.28 |
| 137 | wide15 bladder at side edge | 10 | 70 | 988.1 | 5.63 | 11.21 | 11.5 | 3.07 |
| 138 | wide15 with rigid backing | 6 | 70 | 947.05 | 5.95 | 5.33 | 5.6 | 4.05 |
| 145 | wide 11 test repeatability | 8 | 70 | 558.58 | 6.28 | 9.14 | 9.9 | 3.65 |
| 150 | wide 15 | 4 | 70 | 1004.26 | 6.01 | 5.25 | 9 | 48.6 |
| 152 | wide 15 wide 11 stack high pretension | 2 | 67.7 | 1002.25 | 5.94 | 11.55 | 13.3 | 21.43 |
| 153 | wide 15 | 7 | 70 | 1001.81 | 4.57 | 10.16 | 10.3 | 2.04 |
| 158 | wide 15 test repeatability | 3 | 52.3 | 915.08 | 5.96 | 7.63 | 10.4 | 60.52 |
| 159 | wide 15 + 11 both inside fabric between one connection for both without rigid backing | 3 | 70 | 1004.29 | 6.2 | 7.1 | 7.3 | 2.44 |
| 160 | wide 15 test repeatability without rigid back 30 cycles | 30 | 70 | 996.76 | 5.63 | 10.64 | 11.3 | 4.66 |
| 162 | wide 15 repeat without | 1 | 69.7 | 833.85 | 6.29 | 7.7 | 7.7 | |
| 163 | wide 15 test repeatability | 2 | 70.1 | 463.6 | 6.41 | 5.7 | 5.9 | 4.96 |
| 165 | wide 15 test repeatability | 3 | 70 | 886.14 | 6.18 | 9.77 | 9.8 | 0.59 |
| 168 | wide15 repressed 3 min | 10 | 70 | 881.78 | 6.22 | 10.72 | 11 | 1.63 |
| 174 | wide 15 with rigid backing | 3 | 70.1 | 428.26 | 6.31 | 6.5 | 6.9 | 8.14 |
| 175 | wide 15 | 3 | 70 | 446.87 | 6.33 | 4.87 | 5.4 | 18.98 |
| 176 | wide 15 test of repeatability | 3 | 70.1 | 762.91 | 6.24 | 7.7 | 8.2 | 7.23 |
| 177 | wide 11 test repeatability | 4 | 70 | 491.76 | 6.32 | 10.72 | 10.9 | 3.26 |
| 178 | wide 11 test repeatability with rigid backing | 1 | 69.7 | 433.47 | 6.39 | 5.4 | 5.4 | |
| 182 | wide 18 | 5 | 70 | 995.91 | 6.2 | 14.5 | 15.5 | 4.28 |
| 183 | wide 18 with rigid backing | 2 | 69.9 | 993.88 | 6.11 | 19.2 | 19.4 | 1.47 |
| 191 | test of repeatability wide 18 with rigid backing | 55 | 70 | 996.18 | 6.14 | 20.51 | 21.5 | 1.04 |
| 194 | test of repeatability wide 6 | 7 | 70 | 310.03 | 6.37 | 6.37 | 6.5 | 1.97 |
| 196 | test of repeatability wide 18 with rigid backing | 10 | 70 | 901.25 | 6.57 | 16.31 | 17.6 | 6 |
| 199 | test of repeatability wide18 with rigid backing | 5 | 70 | 892.89 | 6.19 | 16.56 | 16.8 | 1.39 |
| 200 | test of repeatability wide18 | 2 | 70.1 | 908.5 | 6.17 | 13 | 13 | 0 |
| 203 | test of repeatability wide 14 | 25 | 70.1 | 264.59 | 6.16 | 6.1 | 6.7 | 5.87 |
| 204 | test of repeatability wide 6 | 10 | 70 | 280.1 | 6.23 | 7.58 | 7.8 | 4.73 |
| 205 | two wide 11 + 6 with rigid back | 5 | 70 | 391.05 | 6.22 | 5.3 | 5.9 | 10.07 |
| 206 | two wide 11 + 6 with rigid back | 21 | 70 | 497.83 | 6.19 | 7.68 | 8.2 | 9.18 |
| 207 | two wide 11 + 6 with rigid back | 2 | 70.1 | 429.96 | 6.24 | 7.45 | 7.5 | 0.95 |
| 208 | wide 18 on the beaker with Max's rigid back | 7 | 70 | 830.76 | 6.09 | 12.07 | 16.7 | 17.01 |

TABLE B-continued

| | | | Cycle length (s) | Current Avg (mA) | Voltage Avg (V) | PicoPress Avg (mmHg) | PicoPress Max (mmHg) | PicoPress StD (%) |
|---|---|---|---|---|---|---|---|---|
| Experiment | Description | Cycles | | | | | | |
| 209 | wide 18 | 12 | 70 | 710.26 | 6.14 | 11.57 | 13.2 | 17.13 |
| 217 | test of repeatability wide 18 | 3 | 77.9 | 880.49 | 6.11 | 12.97 | 13.3 | 2.23 |
| 218 | test of repeatability wide 18 | 4 | 70 | 915.56 | 6.09 | 14.28 | 15 | 5.98 |

Data collected using the Tactilus® pressure-sensing mat is shown in Table C.

TABLE C

Data collected using the Tactilus ® pressure-sensing mat.

| Experiment ID # | Actuator #1 ID | Actuator #2 ID | Type | Cycle Type | Voltage Limit [V] | Avg ΔP [mmHg] | Max ΔP [mmHg] | Pretension [mmHg] | Current Limit [mA] |
|---|---|---|---|---|---|---|---|---|---|
| B028 | BM 1.01 | | Single | 30 s HC | 3 | 17.61 | 19.78 | 52.5 | |
| B029 | BM 1.02 | | Single | 30 s HC | 3 | 19.36 | 22.07 | 44.3 | |
| B030 | BM 1.03 | | Single | 30 s HC | 3 | 21.33 | 30.48 | 40.8 | |
| B031 | BM 1.04 | | Single | 30 s HC | 3 | 20.14 | 21.03 | 49.9 | 100 |
| B032 | BM 1.05 | | Single | 30 s HC | 3 | 13.06 | 19.68 | 32.8 | |
| B033 | BM 1.03 | | Single | 30 s HC | 5 | 12.31 | 15.96 | 28.6 | |
| B034 | BM 1.06 | | Single | 30 s HC | 3 | 15.39 | 20.13 | 56.0 | |
| B036 | BM 1.08 | | Single | 30 s HC | 3 | 20.91 | 23.42 | 52.9 | |
| B038 | BM 1.08 | | Single | 30 s HC | 3 | 11.82 | 17.44 | 53.3 | |
| B039 | BM 1.08 | | Single | 30 s HC | 3 | 18.85 | 21.89 | 48.4 | |
| B041 | BM 1.09 | | Single | 30 s HC | 3 | 14.69 | 18.6 | 36.5 | |
| B043 | BM 1.12 | | Single | 30 s HC | 3 | 15.88 | 18.32 | 37.8 | |
| B044 | BM 1.21 | | Single | 30 s HC | 3 | 15.58 | 19.93 | 36.2 | |
| B045 | BM 1.22 | | Single | 30 s HC | 3 | 17.79 | 21.45 | 45.3 | |
| B046 | BM 1.08 | | Single | 30 s HC | 3 | 10.89 | 18.33 | 46.3 | |
| B047 | BM 1.11 | | Single | 30 s HC | 3 | 8.30 | 12.67 | 40.2 | |
| B048 | BM 1.08 | | Single | 30 s HC | 3 | 19.20 | 22.27 | 47.0 | |
| B049 | BM 1.11 | | Single | 30 s HC | 3 | 16.19 | 20.8 | 40.4 | |
| B050 | BM 1.13 | | Single | 30 s HC | 3 | 14.02 | 19.37 | 42.2 | |
| B053 | BM 1.16 | | Single | 30 s HC | 3 | 12.02 | 20.15 | 50.1 | |
| B054 | BM 1.15 | | Single | 30 s HC | 3 | 13.63 | 19.5 | 48.5 | |
| B056 | BM 1.08 | | Single | 15 s HC | 3 | 14.49 | 19.79 | 41.2 | |
| B057 | BM 1.08 | | Single | 30 s HC | 3 | 20.51 | 25.91 | 19.9 | |
| B058 | BM 1.08 | | Single | 30 s HC | 3 | 21.95 | 30.19 | 30.6 | |
| B059 | BM 1.08 | | Single | | | 19.00 | | | |
| B060 | BM 1.23 | | Single | 30 s HC | 3 | 8.68 | 13.96 | 33.3 | |
| B061 | BM 1.24 | | Single | 30 s HC | 3 | 9.14 | 19.14 | 37.0 | |
| B062 | BM 1.23 | | Single | 30 s HC | 3 | 17.52 | 19.48 | 21.0 | 100 |
| B063 | BM 1.24 | | Single | 30 s HC | 3 | 9.02 | 12.48 | 45.5 | |
| B065 | BM 1.24 | | Single | 30 s HC | 3 | 10.51 | 18.36 | 42.3 | |
| B066 | BM 1.25 | BM 1.26 | Parallel Stack | 15 s HC | 4 | 18.68 | 20.7 | 46.1 | |
| B067 | BM 1.25 | BM 1.26 | Parallel Stack | 15 s HC | 4 | 21.16 | 24.63 | 43.9 | |
| B068 | BM 1.27 | | Single | 15 s HC | 3 | 20.47 | 21.97 | 52.7 | 300 |
| B069 | BM 1.25 | BM 1.26 | Parallel Stack | 15 s HC | 5 | 21.78 | 27.37 | 50.4 | |
| B070 | BM 1.08 | BM 1.11 | Linear Stack | 15 s HC | 3 | 21.73 | 24.63 | 45.7 | |
| B071 | BM 1.27 | | Single | | 3 | 17.39 | 21.28 | 54.7 | 400 |
| B072 | BM 1.25 | BM 1.26 | Parallel Stack | 15 s HC | 3 | 23.93 | 29.35 | 44.4 | 600 |
| B073 | BM 1.25 | BM 1.26 | Parallel Stack | 30 s HC | 5 | 24.55 | 31.11 | 46.5 | 600 |
| B074 | BM 1.25 | BM 1.26 | Parallel Stack | 15 s HC + 5 s rest | 5 | 16.42 | 20.61 | 35.0 | |
| B076 | BM 1.28 | | Single | 30 s HC | 3 | 19.10 | 20.71 | 27.5 | 100 |
| B077 | BM 1.28 | | Single | 15 s HC + 5 s rest | 5 | 21.20 | 24.03 | 32.3 | 300 |
| B080 | BM 1.23 | | Single | 15 s HC | 5 | 12.77 | 15.43 | 42.4 | 300 |
| B081 | BM 1.26 | | Single | 15 s HC | 5 | 18.54 | 20.76 | 52.2 | 300 |
| B082 | BM 1.28 | | Single | 15 s HC | 5 | 18.20 | 21.94 | 41.5 | 300 |
| B083 | BM 1.29 | | Single | 15 s HC | 5 | 19.81 | 22.56 | 49.0 | 300 |

TABLE C-continued

Data collected using the Tactilus ® pressure-sensing mat.

| Experiment ID # | Actuator #1 ID | Actuator #2 ID | Type | Cycle Type | Voltage Limit [V] | Avg ΔP [mmHg] | Max ΔP [mmHg] | Pretension [mmHg] | Current Limit [mA] |
|---|---|---|---|---|---|---|---|---|---|
| B084 | BM 1.28 | BM 1.30 | Parallel Stack | 15 s HC | 5 | 22.18 | 26.23 | 25.1 | 600 |
| B085 | BM 1.28 | BM 1.30 | Parallel Stack | 15 s HC | 5 | 19.46 | 21.89 | 25.0 | 300 |
| B086 | BM 1.29 | | Single | 15 s HC | 5 | 19.00 | 21.71 | 52.9 | 300 |
| B087 | BM 1.29 | | Single | 15 s HC | 5 | 16.52 | 18.87 | 36.2 | 300 |
| B088 parti | BM 1.29 | BM 1.31 | Parallel Stack | 15 s HC | 5 | 20.25 | 21.91 | 20.0 | 300 |
| B088 part2 | BM 1.29 | BM 1.31 | Parallel Stack | 15 s HC | 5 | 25.32 | 27.89 | 20.0 | 400 |
| B089 | BM 1.32 | | Single | 15 s HC | 5 | 15.25 | 17.7 | 31.5 | 300 |
| B090 | BM 1.32 | | Single | 15 s HC | 5 | 20.28 | 22.22 | 49.0 | 300 |
| B091 | BM 1.28 | BM 1.30 | Parallel Stack | 15 s HC | 5 | 16.01 | 18.66 | 50.7 | 300 |
| B092 | BM 1.32 | | Single | 30 s HC | 3 | 14.98 | 15.98 | 45.3 | 100 |
| B093 | BM 1.33 | | Single | 15 s HC | 5 | 20.39 | 22.8 | 44.8 | 300 |
| B095 | BM 1.29 | BM 1.31 | Parallel Stack | 15 s HC + 5 s rest | 5 | 20.57 | 24.74 | 23.2 | 300 |
| B096 | BM 1.29 | BM 1.31 | Parallel Stack | 15 s HC + 5 s rest | 5 | 22.44 | 26.95 | 25.7 | 400 |
| B097 | BM 1.29 | BM 1.31 | Parallel Stack | 15 s HC + 5 s rest | 5 | 22.01 | 24.78 | 28.8 | 400 |
| B098 | MAS01 | | Single | 15 s HC + 5 s rest | 5 | 22.12 | 28.34 | 30.0 | 300 |
| B099 | MAS02 | | Single | 15 s HC + 5 s rest | 5 | 22.38 | 27.27 | 34.2 | 300 |
| B100 | MAS01 | | Single | 15 s HC + 5 s rest | 5 | 13.44 | 17.75 | 27.3 | 300 |
| B101 | MAS01 | | Single | 15 s HC + 5 s rest | 5 | 12.18 | 17.7 | 30.7 | 300 |
| B102 | MAS02 | | Single | 15 s HC + 5 s rest | 5 | 7.79 | 10.16 | 25.9 | 300 |
| B103 | MAS01 | | Single | 15 s HC + 5 s rest | 5 | 14.91 | 17.55 | 23.3 | 300 |
| B104 | BM 1.24 | | Single | 15 s HC + 5 s rest | 5 | 20.67 | 25.12 | 26.6 | 300 |
| B105 | MAS03 | | Single | 15 s HC + 5 s rest | 5 | 15.42 | 17.48 | 29.8 | 300 |
| B106 | MAS03 | | Single | 15 s HC + 5 s rest | 5 | 20.76 | 23.74 | 33.5 | 300 |
| B107 | BM 1.24 | | Single | 15 s HC + 5 s rest | 5 | 15.03 | 17.88 | 28.4 | 300 |
| B108 | BM 1.26 | | Single | 15 s HC + 5 s rest | 5 | 20.15 | 22.81 | 29.6 | 300 |
| B109 | BM 1.33 | | Single | 15 s HC + 5 s rest | 5 | 21.30 | 24.33 | 34.4 | 300 |
| B110 | BM 1.32 | | Single | 15 s HC + 5 s rest | 5 | 12.54 | 16.29 | 35.8 | 300 |
| B111 | BM 1.33 | | Single | 15 s HC + 5 s rest | 5 | 18.56 | 19.65 | 27.0 | 300 |
| B112 | MAS03 | | Single | 15 s HC + 5 s rest | 5 | 21.18 | 26.08 | 34.4 | 300 |
| B113 | MAS04 | | Single | 15 s HC + 5 s rest | 5 | 19.20 | 22.61 | 28.6 | 300 |
| B114 | MAS05 | | Single | 15 s HC + 5 s rest | 5 | 20.80 | 24.04 | 24.5 | 300 |
| B115 | MAS06 | | Single | 15 s HC + 5 s rest | 5 | 18.44 | 21.68 | 27.8 | 300 |
| B116 | BM 1.35 | | Single | 15 s HC + 5 s rest | 5 | 13.26 | 15 | 29.9 | 300 |
| B119 | MAS03 | | Single | 15 s HC + 5 s rest | 5 | 13.75 | 15.29 | 28.2 | 300 |
| B120 | MAS03 | | Single | 15 s HC + 5 s rest | 5 | 16.10 | 17.94 | 37.4 | 300 |
| B121 | BM 1.34 | | Single | 15 s HC + 5 s rest | 5 | 18.78 | 21.75 | 32.6 | 300 |
| B122 | MAS04 | | Single | 15 s HC + 5 s rest | 5 | 12.35 | 15.08 | 24.1 | 300 |
| B123 | MAS03 | | Single | 15 s HC + 5 s rest | 5 | 15.40 | 18.54 | 28.3 | 300 |
| B124 | MAS07 | | Single | 15 s HC + 5 s rest | 5 | 19.28 | 23.35 | 35.2 | 300 |
| B125 | MAS08 | | Single | 15 s HC + 5 s rest | 5 | 19.98 | 21.41 | 27.3 | 300 |

TABLE C-continued

Data collected using the Tactilus ® pressure-sensing mat.

| Experiment ID # | Actuator #1 ID | Actuator #2 ID | Type | Cycle Type | Voltage Limit [V] | Avg ΔP [mmHg] | Max ΔP [mmHg] | Pretension [mmHg] | Current Limit [mA] |
|---|---|---|---|---|---|---|---|---|---|
| B126 | BM 1.37 | | Single | 15 s HC + 5 s rest | 5 | 10.86 | 12.51 | 28.9 | 300 |
| B127 | BM 1.37 | | Single | 15 s HC + 5 s rest | 5 | 24.79 | 28.84 | 35.9 | 300 |
| B128 | BM 1.37 | | Single | 15 s HC + 5 s rest | 5 | 26.15 | 29.6 | 35.0 | 300 |
| B129 | BM 1.37 | | Single | 15 s HC + 5 s rest | 5 | 20.62 | 23.85 | 32.1 | 300 |
| B130 | BM 1.37 | | Single | 15 s HC + 5 s rest | 5 | 20.54 | 25.35 | 31.6 | 300 |
| B131 | BM 1.36 | BM 1.37 | Parallel Stack | 15 s HC + 5 s rest | 5 | 25.92 | 30.82 | 34.1 | 600 |
| B132 | BM 1.36 | BM 1.37 | Parallel Stack | 15 s HC + 5 s rest | 5 | 24.82 | 30.66 | 30.5 | 600 |
| B133 | BM 1.36 | BM 1.37 | Parallel Stack | 15 s HC + 5 s rest | 5 | 21.94 | 24.57 | 26.0 | 600 |
| B134 | BM 1.38 | BM 1.39 | Parallel Stack | 15 s HC + 5 s rest | 5 | 28.00 | 32.34 | 33.2 | 600 |
| B135 | BM 1.36 | BM 1.37 | Parallel Stack | 15 s HC + 5 s rest | 5 | 16.92 | 20.33 | 30.8 | 600 |
| B136 | BM 1.40 | | Single | 15 s HC + 5 s rest | 5 | 20.15 | 21.45 | 33.2 | 300 |
| B137 | BM 1.40 | BM 1.41 | Parallel Stack | 15 s HC + 5 s rest | 5 | 23.68 | 27.8 | 40.5 | 600 |
| B138 | BM 1.38 | BM 1.39 | Parallel Stack | 15 s HC + 5 s rest | 5 | 29.41 | 33.4 | 16.3 | 600 |
| B142 | wide1 | | Single | 15 s HC + 5 s rest | 5 | 8.90 | 15.39 | 29.8 | 1200 |
| B143 | BM 1.44 | | Single | 15 s HC + 5 s rest | 5 | 18.14 | 22.01 | 28.1 | 300 |
| B144 | BM 1.42 | | Single | 15 s HC + 5 s rest | 5 | 14.32 | 18.48 | 24.2 | 300 |
| B145 | BM 1.43 | | Single | 15 s HC + 5 s rest | 5 | 11.31 | 13.89 | 27.0 | 300 |
| B146 | BM 1.42 | | Single | 15 s HC + 5 s rest | 5 | 14.67 | 16.34 | 32.0 | 300 |
| B148 | wide1 | | Single | 15 s HC + 5 s rest | 5 | 12.61 | 18.86 | 29.7 | 1200 |
| B149 | BM 1.46 | | Single | 15 s HC + 5 s rest | 5 | 13.28 | 16.4 | 27.5 | 300 |
| B150 | BM 1.47 | | Single | 15 s HC + 5 s rest | 5 | 15.06 | 18.12 | 30.8 | 300 |
| B152 | BM 1.49 | | Single | 15 s HC + 5 s rest | 5 | 13.32 | 16 | 31.5 | 300 |
| B153 | BM 1.50 | | Single | 15 s HC + 5 s rest | 5 | 12.32 | 16.26 | 28.6 | 300 |
| B154 | BM 1.51 | | Single | 15 s HC + 5 s rest | 5 | 10.36 | 14.65 | 20.0 | 300 |
| B155 | BM 1.49 | | Single | 15 s HC + 5 s rest | 5 | 17.52 | 19.5 | 35.3 | 300 |
| B156 | wide1 | | Single | 15 s HC + 5 s rest | 5 | 11.71 | 19.48 | 33.9 | 1200 |
| B157 | BM 1.55 | | Single | 15 s HC + 5 s rest | 5 | 10.17 | 12.4 | 31.9 | 300 |
| B158 | BM 1.42 | | Single | 15 s HC + 5 s rest | 5 | 11.17 | 15.47 | 31.5 | 300 |
| B159 | long 1 | | Single | 15 s HC + 5 s rest | 5 | 11.18 | 17.91 | 31.6 | 400 |
| B160 | BM 1.52 | | Single | 15 s HC + 5 s rest | 5 | 9.25 | 12.14 | 27.6 | 300 |
| B161 | BM 1.56 | | Single | 15 s HC + 5 s rest | 5 | 17.65 | 20.74 | 30.3 | 300 |
| B162 | BM 1.53 | | Single | 15 s HC + 5 s rest | 5 | 13.84 | 15.39 | 30.8 | 300 |
| B164 | BM 1.43 | | Single | 15 s HC + 5 s rest | 5 | 7.08 | 10.66 | 27.0 | 300 |
| B165 | BM 1.46 | | Single | 15 s HC + 5 s rest | 5 | 11.90 | 15.77 | 23.9 | 300 |
| B166 | BM 1.57 | | Single | 15 s HC + 5 s rest | 5 | 16.08 | 18.66 | 28.0 | 300 |
| B167 | BM 1.58 | | Single | 15 s HC + 5 s rest | 5 | 17.13 | 19.61 | 34.8 | 300 |
| B170 | BM 1.46 | | Single | 15 s HC + 5 s rest | 5 | 8.85 | 14.16 | 28.5 | 300 |

TABLE C-continued

Data collected using the Tactilus ® pressure-sensing mat.

| Experiment ID # | Actuator #1 ID | Actuator #2 ID | Type | Cycle Type | Voltage Limit [V] | Avg ΔP [mmHg] | Max ΔP [mmHg] | Pretension [mmHg] | Current Limit [mA] |
|---|---|---|---|---|---|---|---|---|---|
| B172 | BM 1.46 | | Single | 15 s HC + 5 s rest | 5 | 11.61 | 19.28 | 28.4 | 300 |
| B175 | panel 1 | | Single | 15 s HC + 5 s rest | 5 | 16.95 | 25.98 | 34.2 | 300 |
| B176 | panel 2 | | Single | 15 s HC + 5 s rest | 5 | 17.34 | 23.65 | 25.2 | 300 |
| B177 | panel 1 | panel 2 | Side by Side | 15 s HC + 5 s rest | 5 | 17.09 | 20.85 | 40.8 | 600 |
| B178 | BM 1.54 | | Single | 15 s HC + 5 s rest | 5 | 13.90 | 18.69 | 36.7 | 300 |
| B179 | BM 1.57 | | Single | 15 s HC + 5 s rest | 5 | 7.18 | 10.4 | 30.4 | 300 |
| B180 | BM 1.58 | | Single | 15 s HC + 5 s rest | 5 | 9.81 | 14.44 | 31.3 | 300 |
| B183 | BM 1.59 | | Single | 15 s HC + 5 s rest | 5 | 10.05 | 11.44 | 33.3 | 300 |
| B184 | BM 1.60 | | Single | 15 s HC + 5 s rest | 5 | 10.75 | 14.26 | 34.9 | 300 |
| B185 | wide2 | | Single | 15 s HC + 5 s rest | 5 | 9.22 | 17.01 | 21.6 | 1200 |
| B186 | BM 1.61 | | Single | 15 s HC + 5 s rest | 5 | 9.36 | 11.96 | 27.2 | 300 |
| B187 | BM 1.59 | | Single | 15 s HC + 5 s rest | 5 | 9.76 | 13.48 | 35.8 | 300 |
| B188 | BM 1.60 | | Single | 15 s HC + 5 s rest | 5 | 8.03 | 11.74 | 36.8 | 300 |
| B189 | wide2 | | Single | 15 s HC + 5 s rest | 5 | 10.71 | 17.3 | 35.9 | 1200 |
| B190 | BM 1.62 | | Single | 15 s HC + 5 s rest | 5 | 19.34 | 21.96 | 39.5 | 300 |
| B191 | wide2 | | Single | 15 s HC + 5 s rest | 5 | 7.60 | 14.56 | 26.2 | 1200 |
| B192 | BM 1.63 | | Single | 15 s HC + 5 s rest | 5 | 9.33 | 13.06 | 23.8 | 300 |
| B193 | BM 1.62 | | Single | 15 s HC + 5 s rest | 5 | 13.18 | 17.58 | 29.4 | 300 |
| B193bis(last50) | BM 1.62 | | Single | 15 s HC + 5 s rest | 5 | 19.10 | 21.79 | 29.4 | 300 |
| B194 | wide2 | | Single | 15 s HC + 5 s rest | 5 | 11.83 | 18.5 | 32.4 | 1200 |
| B195 | BM 1.64 | | Single | 15 s HC + 5 s rest | 5 | 17.70 | 19.82 | 37.0 | 300 |
| B196 | BM 1.65 | | Single | 15 s HC + 5 s rest | 5 | 17.04 | 18.39 | 39.8 | 300 |
| B197 | wide2 | | Single | 15 s HC + 5 s rest | 5 | 8.69 | 17.92 | 29.0 | 1200 |
| B198 | wide2 | | Single | 15 s HC + 5 s rest | 5 | 12.17 | 18.92 | 32.2 | 1200 |
| B199 | BM 1.66 | | Single | 15 s HC + 5 s rest | 5 | 18.10 | 21.77 | 35.5 | 300 |
| B200 | BM 1.67 | | Single | 15 s HC + 5 s rest | 5 | 18.09 | 20.04 | 37.8 | 300 |
| B201 | BM 1.68 | | Single | 15 s HC + 5 s rest | 5 | 21.40 | 27.01 | 34.0 | 300 |
| B202 | BM 1.66 | BM 1.67 | Side by Side | 15 s HC + 5 s rest | 5 | 8.53 | 17.14 | 28.4 | 900 |
| B203 | BM 1.69 | | Single | 15 s HC + 5 s rest | 5 | 17.89 | 20.55 | 34.7 | 300 |
| B204 | BM 1.66 | BM 1.67 | Side by Side | 15 s HC + 5 s rest | 5 | 15.31 | 19.34 | 23.7 | 900 |
| B205 | BM 1.56 | | Single | 15 s HC + 5 s rest | 5 | 11.97 | 18.98 | 29.1 | 300 |
| B206 | BM 1.58 | | Single | 15 s HC + 5 s rest | 5 | 10.01 | 15.11 | 31.5 | 300 |
| B210 | BM 1.57 | | Single | 15 s HC + 5 s rest | 5 | 7.33 | 9.45 | 36.3 | 300 |
| B212 | BM 1.71 | | Single | 15 s HC + 5 s rest | 5 | 19.53 | 24.98 | 34.8 | 300 |
| B213 | BM 1.72 | | Single | 15 s HC + 5 s rest | 5 | 20.94 | 25.84 | 32.1 | 300 |
| B215 | BM 1.76 | | Single | 15 s HC + 5 s rest | 5 | 15.13 | 18.27 | 32.9 | 300 |
| B216 | BM 1.31 | | Single | 15 s HC + 5 s rest | 5 | 16.00 | 17.89 | 37.4 | 300 |

TABLE C-continued

Data collected using the Tactilus ® pressure-sensing mat.

| Experiment ID # | Actuator #1 ID | Actuator #2 ID | Type | Cycle Type | Voltage Limit [V] | Avg ΔP [mmHg] | Max ΔP [mmHg] | Pretension [mmHg] | Current Limit [mA] |
|---|---|---|---|---|---|---|---|---|---|
| B217 | BM 1.29 | | Single | 15 s HC + 5 s rest | 5 | 10.60 | 17.23 | 35.9 | 300 |
| B220 | BM 1.76 | | Single | 15 s HC + 5 s rest | 5 | 18.13 | 21.91 | 35.6 | 200 |
| B221 | BM 1.37 | | Single | 15 s HC + 5 s rest | 5 | 18.65 | 23.9 | 30.0 | 300 |
| B222 | BM 1.35 | | Single | 15 s HC + 5 s rest | 5 | 16.26 | 19.29 | 36.7 | 300 |
| B223 | SnapStack1 | | Single | 15 s HC + 5 s rest | 5 | 18.66 | 22.19 | 40.3 | 600 |
| B224 | Iong2 | | Single | 15 s HC + 5 s rest | 5 | 12.74 | 18.26 | 34.9 | 300 |
| B225 | BM 1.77 | | Single | 15 s HC + 5 s rest | 5 | 16.72 | 20.13 | 33.0 | 300 |
| B226 | BM 1.80 | | Single | 15 s HC + 5 s rest | 5 | 14.53 | 17.48 | 34.1 | 300 |
| B227 | BM 1.81 | | Single | 15 s HC + 5 s rest | 5 | 16.24 | 19.12 | 28.3 | 300 |
| B228 | BM 1.79 | | Single | 15 s HC + 5 s rest | 5 | 17.25 | 22.49 | 20.0 | 300 |
| B229 | WideSnapStack1 | | Parallel Stack | 15 s HC + 5 s rest | 5 | 16.58 | 28.68 | 35.0 | 900 |
| B230 | BM 1.79 | | Single | 15 s HC + 5 s rest | 5 | 17.23 | 18.05 | 36.7 | 300 |
| B231 | BM 1.82 | | Parallel Stack | 15 s HC + 5 s rest | 5 | 17.10 | 19.74 | 38.3 | 600 |
| B232 | BM 1.83 | | Single | 15 s HC + 5 s rest | 5 | 14.77 | 18.28 | 40.2 | 300 |
| B233 | BM 1.83 | | Single | 15 s HC + 5 s rest | 5 | 20.95 | 28.21 | 35.2 | 300 |
| B234 | BM 1.83 | | Single | 15 s HC + 5 s rest | 5 | 19.59 | 22.67 | 32.7 | 600 |
| B235 | BM 1.84 | | Parallel Stack | 15 s HC + 5 s rest | 5 | 22.93 | 28.62 | 32.7 | 600 |
| B236 | BM 1.84 | | Parallel Stack | 15 s HC + 5 s rest | 5 | 19.64 | 25.28 | 36.5 | 600 |
| B237 | BM 1.84 | | Parallel Stack | 15 s HC + 5 s rest | 5 | 19.38 | 26.15 | 36.0 | 600 |
| B238 | BM 1.85 | | Single | 15 s HC + 5 s rest | 5 | 14.97 | 17.47 | 38.1 | 600 |

Example 8

EAP Compositions Comprising PEG Show Increased Robustness

The following test conditions were used: Current: 100 mA; Voltage: 3V; Actuation cycles: 30 second increase/30 second decrease; at Room temperature and normal humidity level.

Figure 13A:
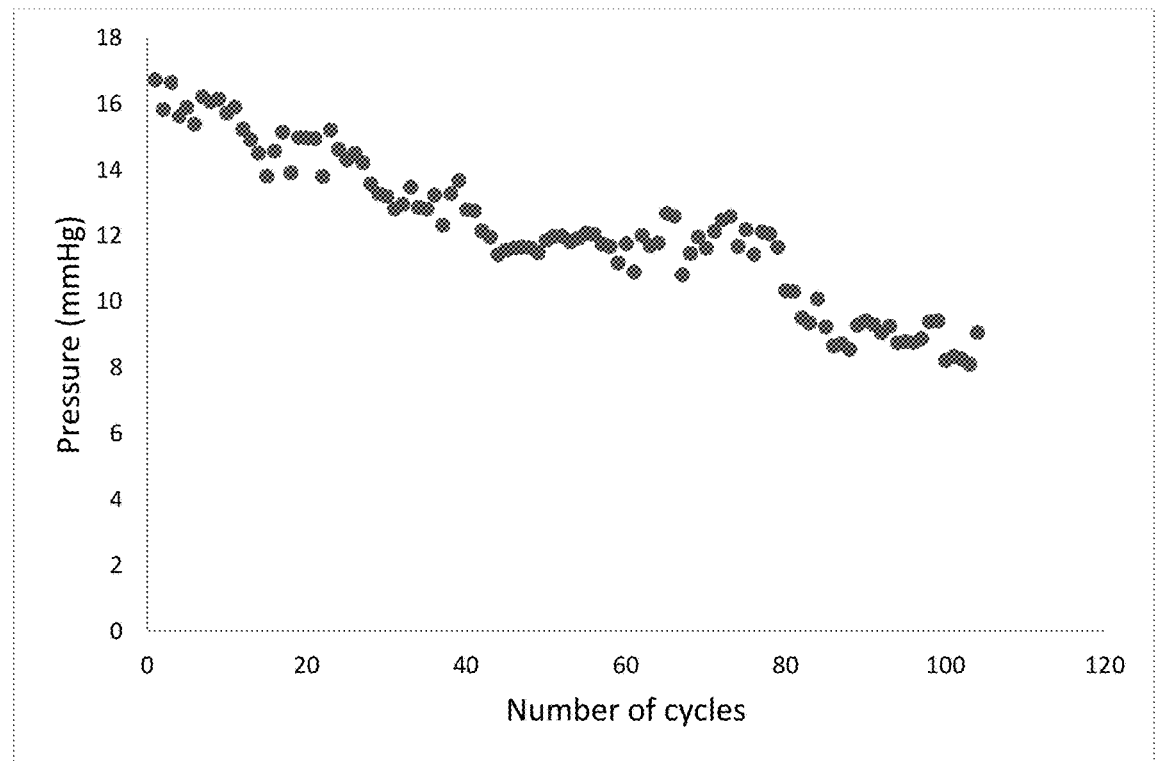
FIG. 13A is a graph showing pressure change for an aysmmetric actuator without PEG in the EAP composition layer.

In one experiment, the test was conducted using SSM32 without PEG for the EAP and SSM-04-g for the SPE. Results are shown in FIG. 13A. The average pressure change (Average ΔP) was 12.31 mmHg for 100 cycles.

Figure 13B:
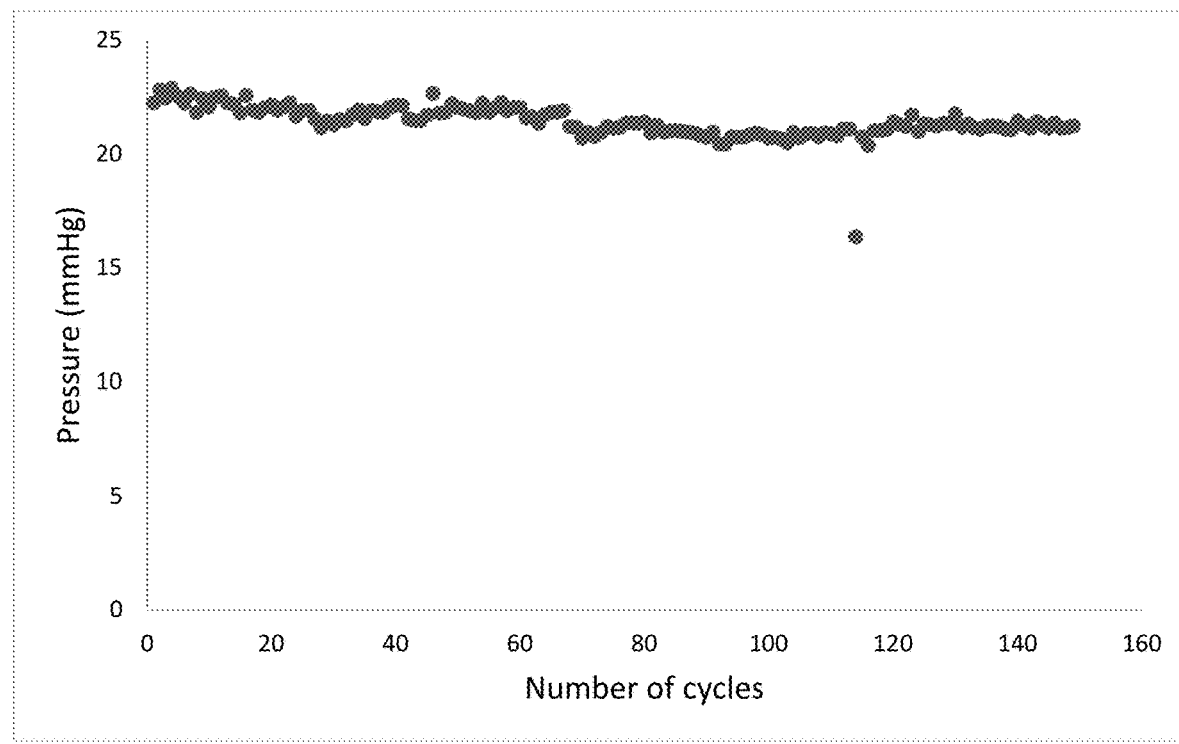
FIG. 13B is a graph showing pressure change for an aysmmetric actuator with PEG in the EAP composition layer.

In another experiment, the test was conducted using SSM34 with PEG for the EAP and SSM-04-g for the SPE. Results are shown in FIG. 13B. The average pressure change (Average ΔP) was 20.91 mmHg for 150 cycles. The results show that PEG in the EAP composition layer increased the pressure significantly.

Example 9

SSEPAs Comprising PEVA and Graphene

SSEPAs (both symmetric and asymmetric) comprising ethylene-vinyl acetate (EVA) were tested. The results showed that EVA enhanced stretchability (i.e., the ability of the SSEPA to elongate).

SSEPAs (both symmetric and asymmetric) comprising graphene (e.g., carbon nanotubes (CNT)) were tested. About 1-15 wt % graphene was added to the EAP composition layer.

In one example, an EAP composition comprising about 3.3 wt % graphene, 15.6 wt % ethylene-vinyl acetate (EVA), 43.3 wt % PEDOT:PSS, 20 wt % PEG and 17.8 wt % glycerol was tested.

The results showed that graphene/CNT increased the stiffness of the EAP layer (and hence the actuator). SSEPAs comprising graphene/CNT were more resistant to rupture (had a higher break point) and could generate higher pressure. Introduction of graphene to the EAP formulation also increased the linear strain ratio up to 1% of a single actuator.

The results show therefore that fillers such as graphene/ CNT can increase stiffness, increase anisotropy of contraction, and/or increase electrical conductivity of the SSEPAs of the present technology. In some cases, the strain ratio can be tripled by the inclusion of such filler.

The results show also that PEVA and graphene/CNT together increased the strain ratio and pressure generation of the SSEPAs.

It is expected that a wide range of nanostructures with similar mechanical properties can provide the same or similar effects. Non-limiting examples include graphene, graphite, carbon black, graphene oxide, carbon nanotubes, and the like.

Example 10

Stacked SSEPAs

In some embodiments, two or more SSEPAs are stacked. Stacking can increase the amount of pressure generated by the actuator assembly.

Figure 14A:
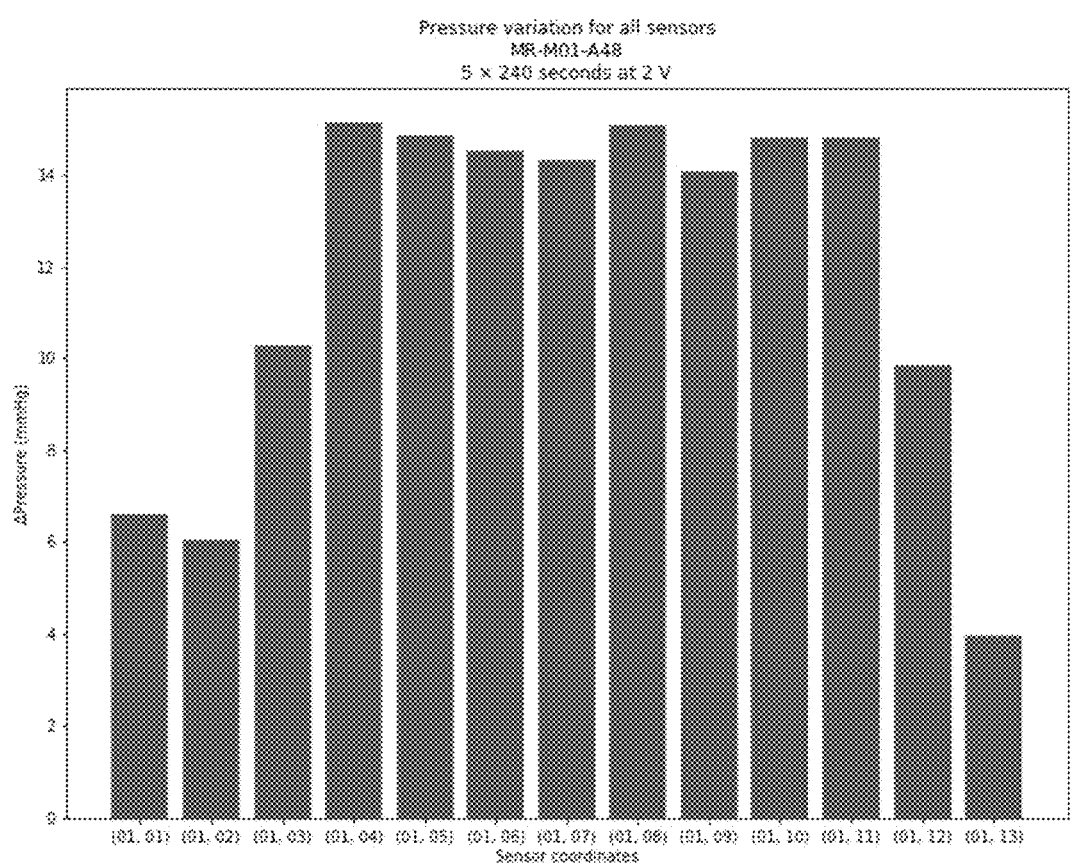
FIGS. 14A-14B show stacking actuators increases the pressure generated.
Figure 14B:
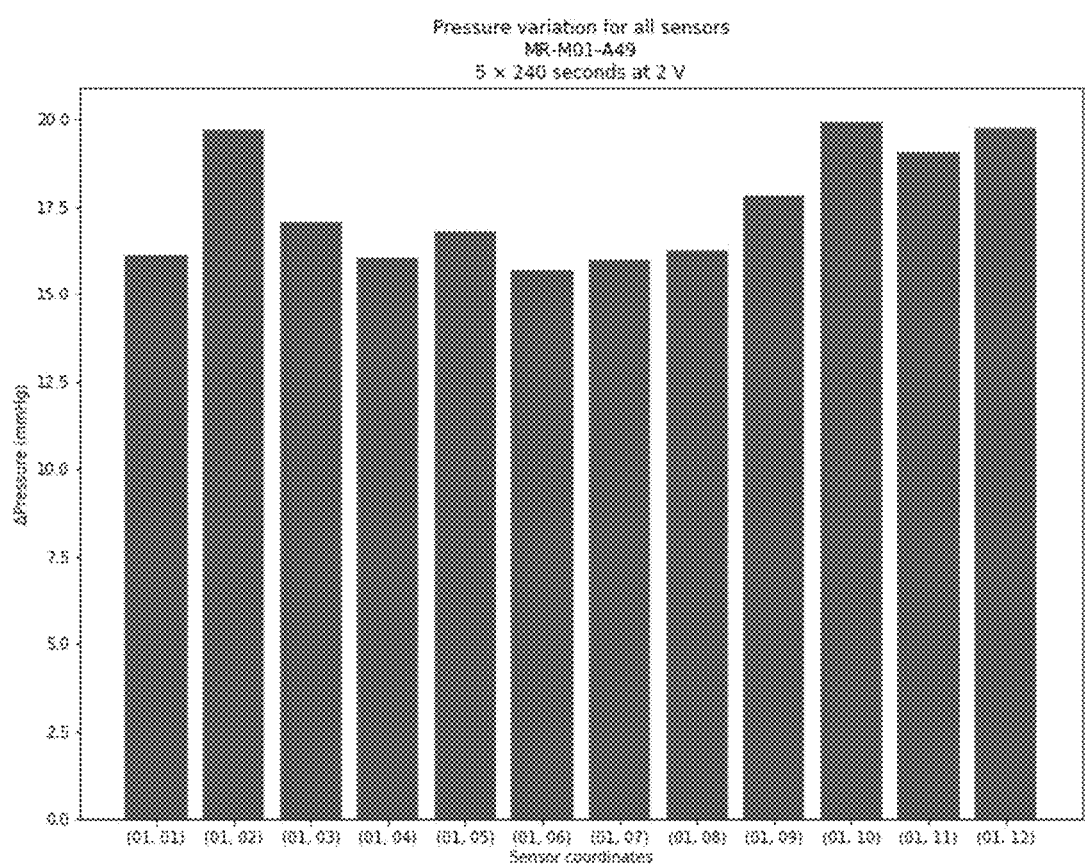

Tests were conducted to determine whether stacking actuators could increase the pressure generated. It was found that stacking increased the pressure by approximately 50%. The stacking method was as discussed above and shown in FIG. 10C. First, a single actuator MR-M01-A48 was tested (20 cm long actuator). The peak pressure was 15.2 mmHg and the average pressure was 11.9 mmHg. Results are shown in FIG. 14A, which shows the pressure variation under the actuator measured with different pressure sensors. Next, stacked actuators ME-M01-A49 were tested (20 cm long actuators). The peak pressure was 19.9 mmHg and the average pressure was 17.5 mmHg. Results are shown in FIG. 14B, which shows the pressure variation under the actuator measured with different pressure sensors.

Example 11

Unixial Pre-Stretching

Unixial pre-stretching of the EAP composition layer during manufacturing of the film was found to increase pressure generation, for example by about 30%, about 40%, or more, of the SSEPA actuator. Without wishing to be limited by theory, it is believed that pre-stretching of the EAP film during manufacturing can increase the anisotropy of the SSEPA which allows for preferential straining in one axis, and increases the number of channels available of ion flow. Higher ion flow leads to more actuation and more pressure generated.

In some embodiments, increased performance (e.g., pressure) of an SSEPA is obtained by unixial pre-stretching of the EAP film during preparation thereof. For example, stretching the EAP film during the last step of its preparation, optionally while heating, can provide an increase in subsequent pressure generation of up to 40% or more by the SSEPA.

Figure 15A:
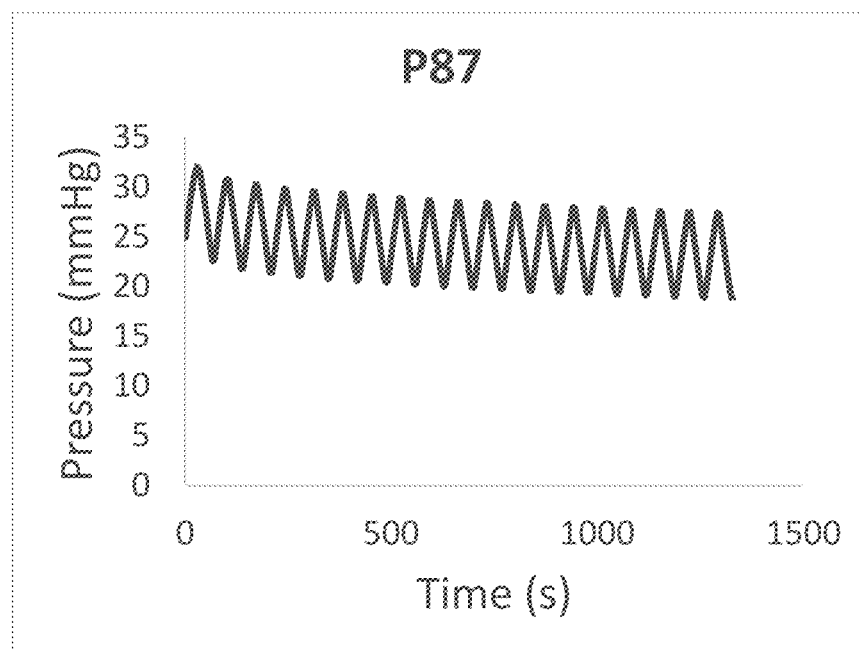
FIGS. 15A-15C show pre-stretching of the EAP composition film layer during manufacture can increase pressure generation.
Figure 15B:
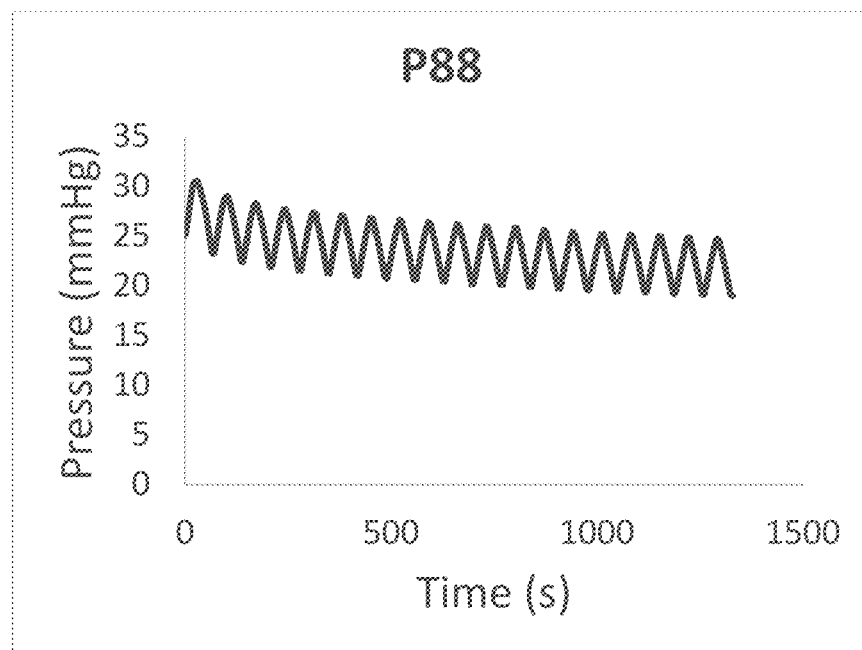
Figure 15C:
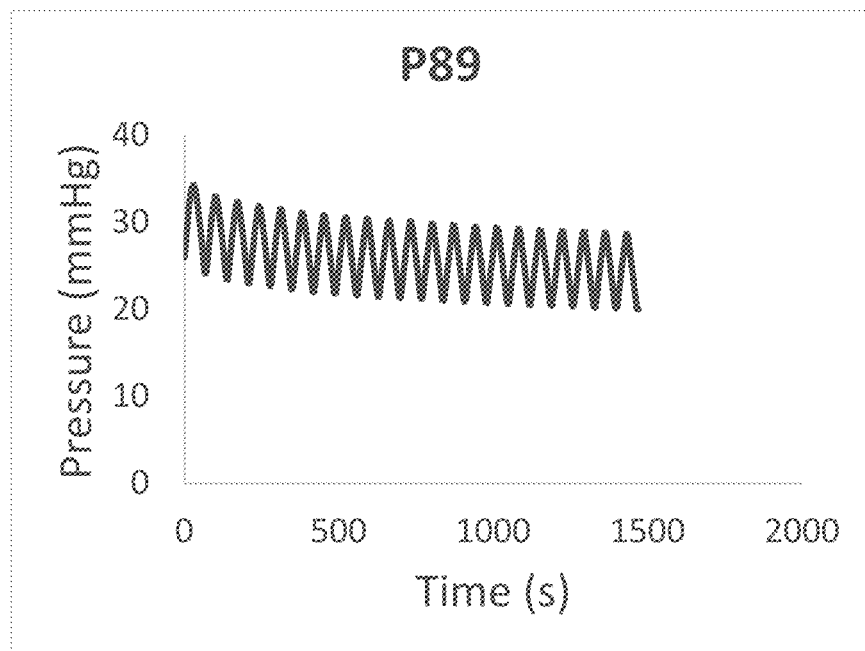

In the experiment shown here, stretching the EAP was done by clamping the dried EAP film at both ends and stretching uniformly while heating the film up to 60° C. until the desired strain ratio was achieved. The effect of the stretching on pressure generation was determined as follows: Three non-symmetrical actuators with length of 24 cm and width of 5 cm were prepared with the SS-M-38 EAP and SS-M-04-g SPE described above. The EAP was either not stretched or stretched in parallel or perpendicular direction to the length of the actuator. Pressure was measured on a rigid cylinder with PicoPress® at a limit voltage of 6V and limit current of 425 mA. About 50% increase in generated pressure was observed. Results are shown in Table 4 and FIGS. 15A-C.

TABLE 4

Unixial pre-stretching of the EAP during manufacturing of the EAP film layer increases pressure generated by the SSEPA.

| Test | EAP stretching (%) | Pressure (mmHg) |
|---|---|---|
| P88 | 0 | 6 |
| P89 | 8 (length direction) | 8.9 |
| P87 | 9 (width direction) | 8.7 |

Example 12

Tensile Tests to Determine Effect of Rigid Backing on Actuation

The experiment consisted of measuring the force generated while imposing a ramp of displacement of 10 mm on the SSEPA. The experiment was conducted 3 times at rest state ("rest"), 3 times after charging (extension state, or "extended") and 3 times after discharging (contraction states, or "contracted"). This experiment was repeated twice (BM1.1 and BM1.2).

Figure 11A:
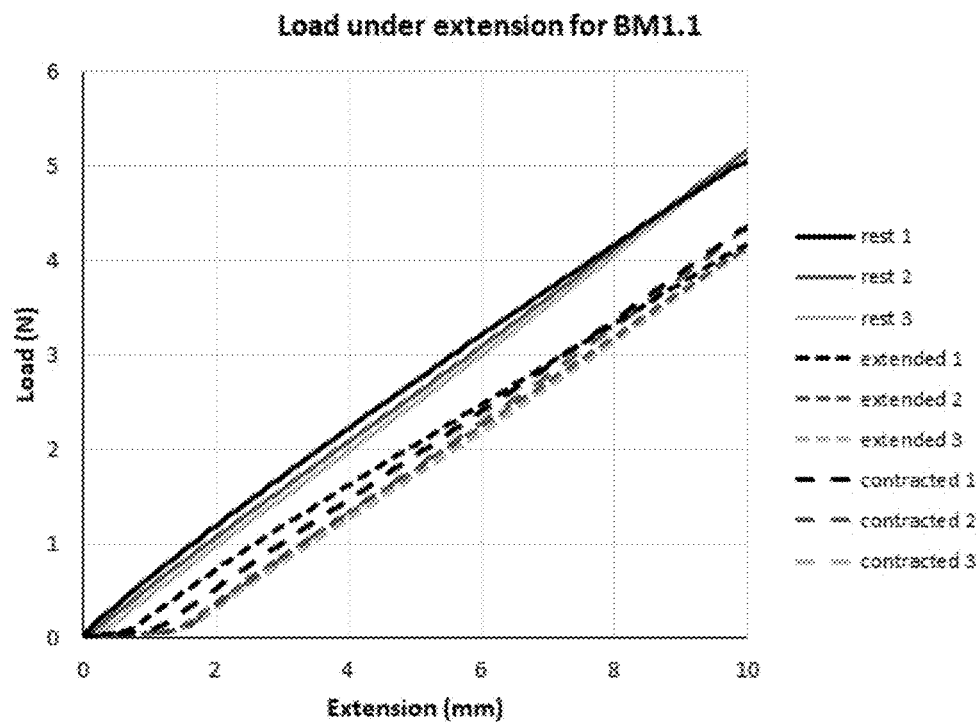
FIG. 11A is a graph showing force vs. displacement for a SSEPA at rest, after charging (extended), and after discharging (contracted).
Figure 11B:
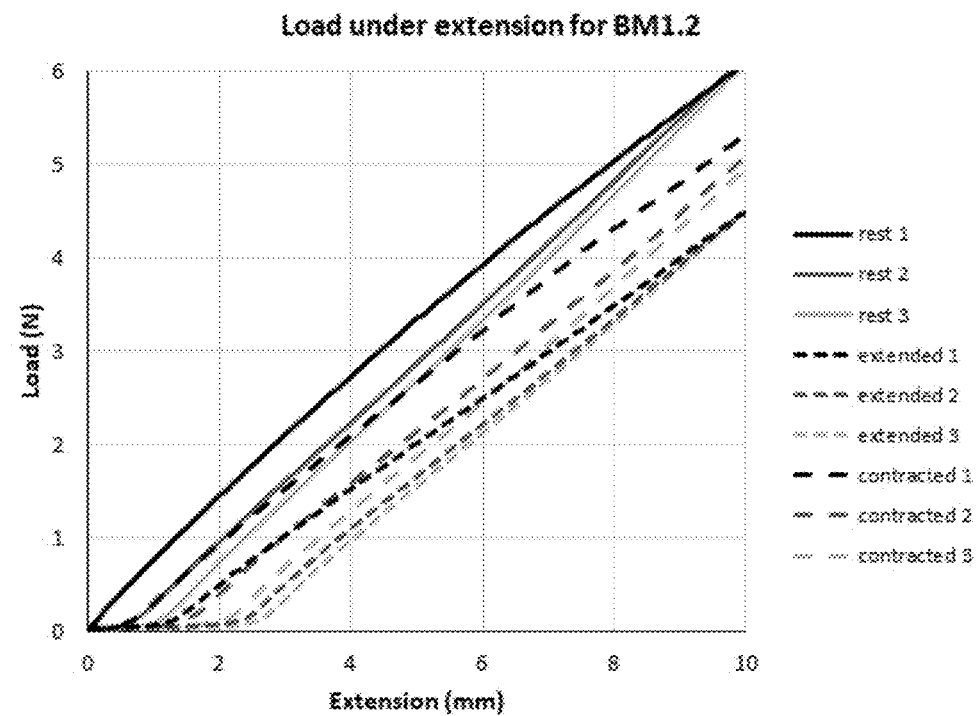
FIG. 11B is a graph showing force vs. displacement for a SSEPA at rest, after charging (extended), and after discharging (contracted).

It was found that at maximum elongation (10 mm) the force always followed "contraction>extension", as expected. At rest (before actuation), the forces were always greater. This is most likely due to creeping/flowing of the actuator. The measurements of stiffness (Young's modulus) were very close. Results are shown in FIGS. 11A-B and in Table 5.

TABLE 5

Effect of activation on rigidity of the actuator.

| Young modulus (MPa) | BM1.1 | BM1.2 |
|---|---|---|
| Rest 1 | 7.18209 | 9.46395 |
| Rest 2 | 6.66659 | 8.77849 |
| Rest 3 | 6.75688 | 9.19288 |
| Extended 1 | 5.51418 | 6.67653 |
| Extended 2 | 5.87376 | 7.66667 |
| Extended 3 | 6.07121 | 8.06238 |
| Contracted 1 | 6.16309 | 8.18425 |
| Contracted 2 | 6.61901 | 8.16541 |
| Contracted 3 | 6.36078 | 8.40828 |

Figure 11C:
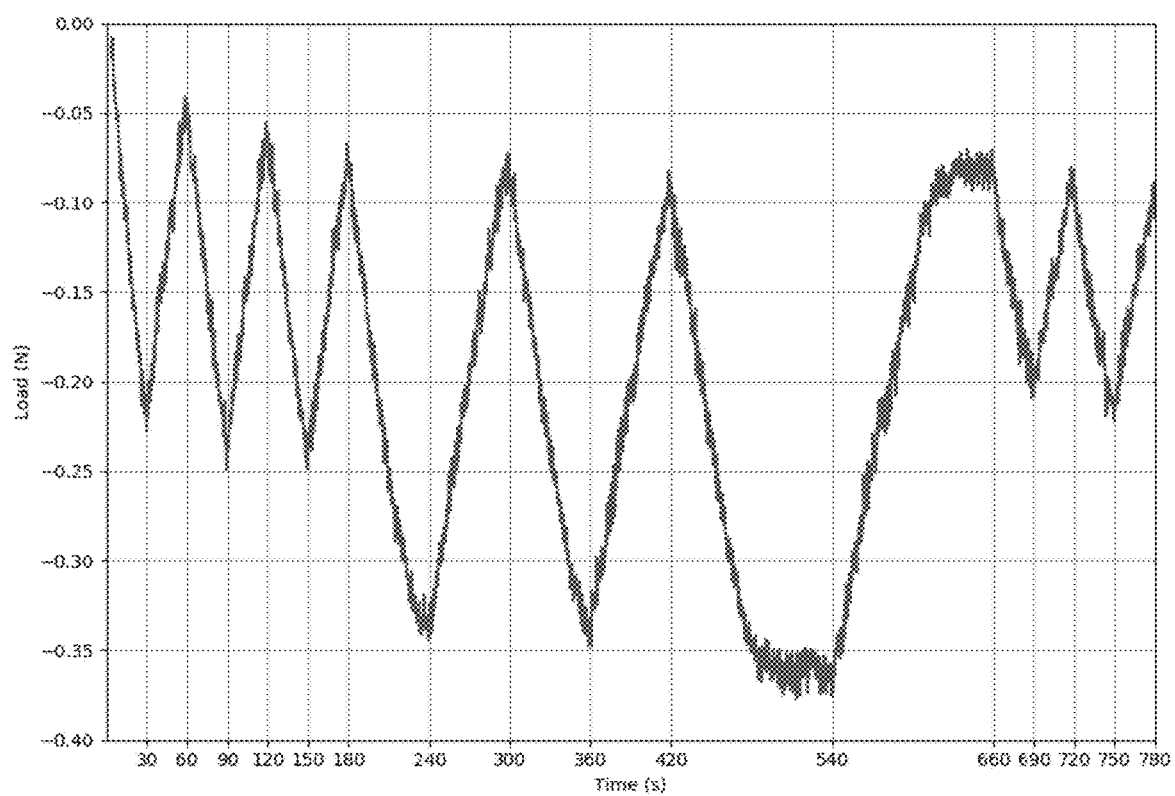
FIG. 11C is a graph of load vs. time showing validation of a Scale Test used for tensile testing.

FIG. 11C shows validation of the scale test used for tensile testing. The experiment on the scale was replicated with the instron. 1 min, 2 min, and 4 min periods can be seen, indicating about the same force measured with the tests conducted above and validating the above results. In this experiment, a 14 cm by 1.5 cm actuator was made with EAP chemistry SS-M-28 and SPE chemistry SS-M-04-g. It was fixed at the two ends in the Instron tensile test machine and it was not allowed to move during the test. Electrical input was at the two ends at a voltage limit of 5V and current limit of 150 mA and the force variation was measured with time.

Example 13

Rigid Backing

Pressure management tests were performed with SSEPAs attached to a rigid backing. This was found to increase local pressure.

The rigid backing used is not particularly limited. Any polymers suitable to provide a high-stiffness or rigid overlayer to the actuator can be used in such embodiments. Non-limiting examples of such polymers include, without limitation, polycarbonate, acrylic plastics, polyolefins, and polyesters.

Figure 16A:
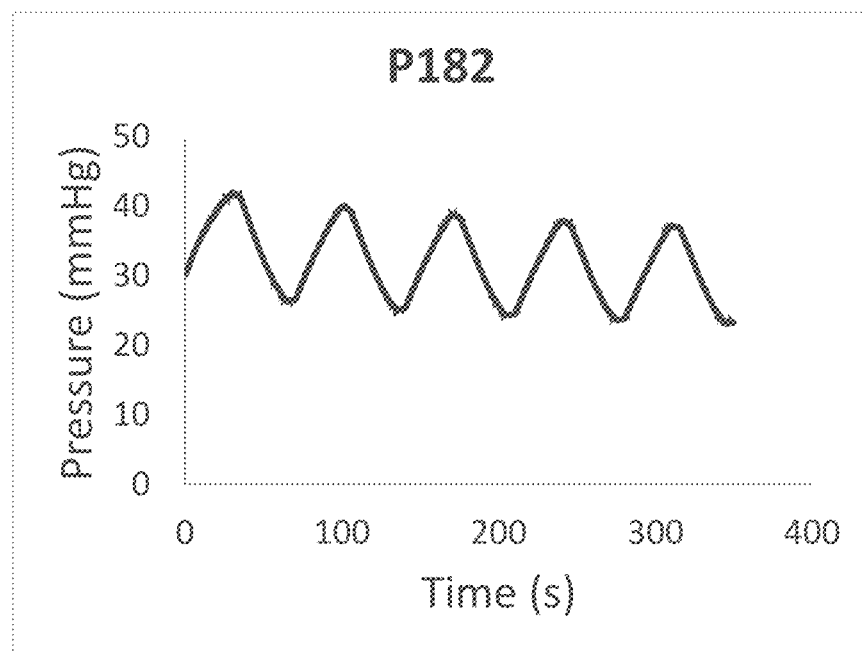
FIGS. 16A-16B show SSEPA pressure increases significantly with a rigid backing.
Figure 16B:
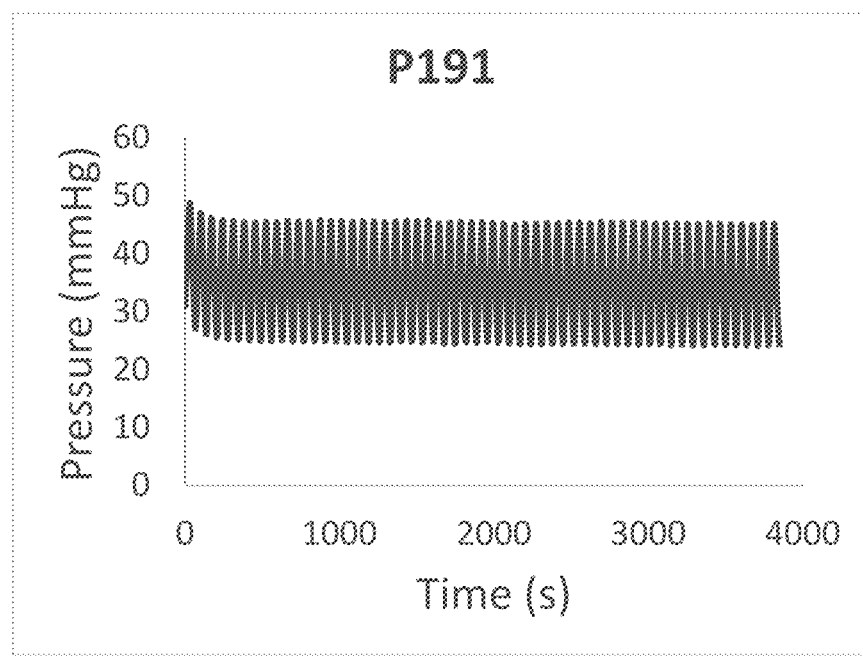

In this experiment, an asymmetric actuator of 26 cm in length and 14 cm in width was used with EAP chemistry SS-M-32 and SPE chemistry SS-M-04-g. The EAP film was stretched 23% and the stretching was in parallel to the length of the actuator. Pressure generation was measured on a rigid cylinder. Results are shown in Table 6 and FIGS. 16A-B.

TABLE 6

Local pressure increases with rigid backing.

| Test | Rigid backing | Pressure (mmHg) |
|---|---|---|
| P182 | No | 13.3 |
| P191 | Yes | 20.5 |

The results show that applying a high-stiffness overlayer to the actuator increased the force and pressure of the actuator. These results suggest that a high-stiffness overlayer or rigid backing could be used to enhance force and pressure transfer from an actuator to a body, particularly for a soft body or body part, such as a leg.

Example 14

Electroactive Polymer Capacitive Sensors

SSEPAs in accordance with certain embodiments of the present technology were tested for use as capacitive sensors. The SSEPAs tested were composed of two EAP electrodes separated by a dielectric film. This assembly was then sealed in a polymer shell to protect it, as visible in FIG. 12A. Detection was based on the measurement of the change of electric capacitance. This change occurred when the between the two EAP electrodes, or their area, was affected by a mechanical stimulus. This stimulus could be either the application of pressure of the bending of the sensor.

The dielectric film sandwiched between the two EAP electrodes/composition layers is not particularly limited. Any suitable stretchable, flexible dielectric polymer can be used. Non-limiting examples include SEEPS, SEBS, Poly (dimethyl siloxane), cellulose-based polymers, polyurethane, and combinations thereof.

The EAP and SPE compositions used in the sensors are also not particularly limited. Any suitable EAP and SPE composition as described herein may be used in the sensors. It is noted that, when the SSEPA is used as a sensor, salt is not required in the SPE composition layer. In some embodiments therefore, when the SSEPA is used as a sensor, the SPE composition layer does not include salt.

As the sensors are entirely made of polymers, they provided complete flexibility. Moreover, they could be easily assembled as an array to form a multipoint sensing surface. These properties allow use of the sensors in applications where complex geometry and multipoint sensing on a large area are required, such as an artificial skin. The tests show that the SSEPAs of the present technology can function as capacitive sensors suitable for a variety of applications such as, without limitation, detecting qualitative changes of pressure (e.g., contact sensor) or quantitative pressure or mass (assuming appropriate calibration is performed).

Manufacture of sensors. The EAP was cut in the desired shapes (electrodes and wiring). For example, 2 pieces of EAP composed of a 10 mm×10 mm square electrode with a wire 1 mm×100 mm connected to the lower left corner of the electrode were prepared. Next, the PVDF was cut in order to fully cover the electrode part of the EAP. For example, one 10 mm×10 mm square piece of PVDF was cut. Next, the SPE was cut to be 1 mm larger than the electrodes on every side. For example, two 12 mm×12 mm square pieces of SPE were cut. Next, the first EAP piece was centered on the first SPE piece. The assembly was hot-pressed at 100° C. Then the piece of PVDF was centered on the electrode of the assembly, and hot-pressed at 100° C. The second EAP piece was then centered on the first EAP piece. It's important to make sure that the wires are not in contact. This assembly was hot-pressed at 100° C. Finally, the second SPE piece was centered on the first SPE piece and the assembly was hot-pressed at 100° C. It should be noted that any SPE composition as described herein can be used in the sensors. In some embodiments, the SPE for the sensor does not include a salt, as the salt is not required for activity in the sensor. In the experiments shown here, the SPE used was styrene-co-ethylene-co-ethylenepropylene-co-styrene (SEEPS) or styrene-co-ethylene-co-butylene-co-styrene (SEBS).

Characteristics. Characteristics of the SSEPA shown and tested here were as follows: Sensor area: 1 $cm^2$; Sensor thickness: <1 mm; Capacitance range: 100 $pF/cm^2$ to 1500 $pF/cm^2$; Pressure range: from less than 0.02 $N/cm^2$ to above 200 $N/cm^2$ for pressure mode; Frequency response: >1 Hz baseline to baseline; Detection modes: Pressure, Bending; Maximum temperature: 110° Celsius; Stretchability: 5% to 9% of its length; Bend radius: <1.5 m.

Figure 12B:
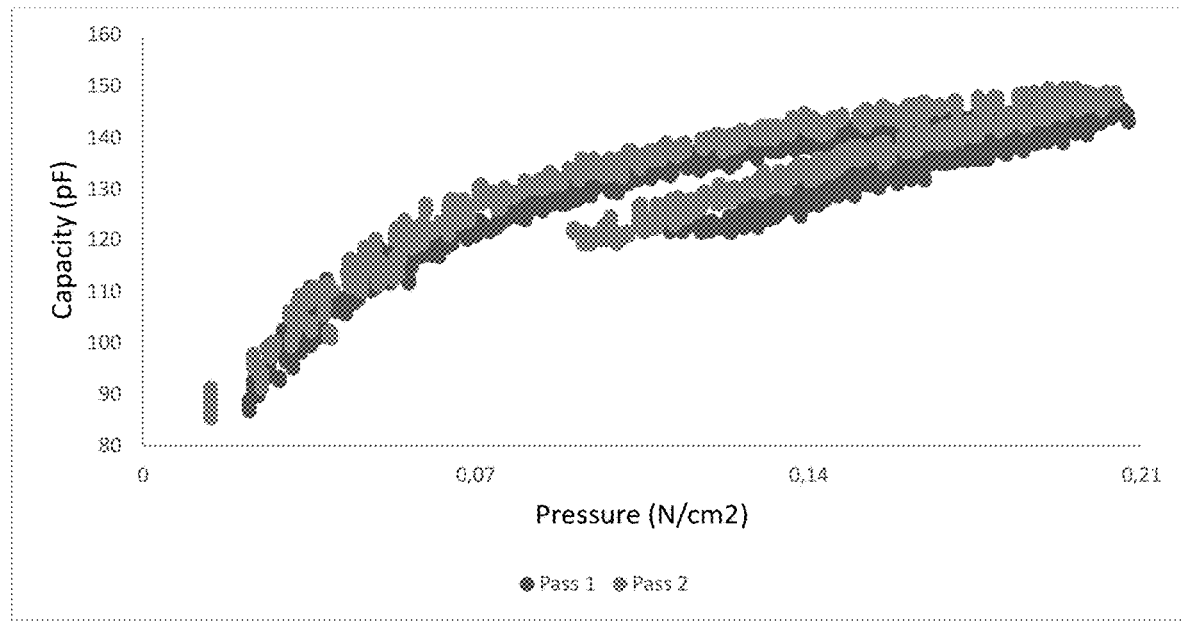
FIG. 12B shows a graph of capacity vs. pressure for a low-pressure response test of an electroactive polymer capacitive sensor (blue: Pass 1; red: Pass 2).

Low-pressure response test. The low-pressure response test was performed by positioning a sensor under a mechanical press and increasing then decreasing the pressure linearly while measuring the sensor response. Capacitance of the sensor was measured against a triangular pressure pattern from 0 $N/cm^2$ to 0.2 $N/cm^2$ with a pressure rate of 0.1 $N/cm^2$ over 2 passes. Results are shown in FIG. 12B. The arrows indicate the direction of the cycles. Due to some instability of the measurement system at low pressure, some low-pressure data points were not available.

These measurements showed a relatively linear behavior when the pressure is rising followed by a non-linear behavior when the pressure is decreasing, inducing a hysteresis. This hysteresis showed that the sensor elasticity was such that it required more time to get back to its initial state than to get compressed. By comparing the two passes, we can observe that the values given by the sensor were within a 5% range. This measurement shows minimum measured pressure under 0.02 $N/cm^2$.

Figure 12C:
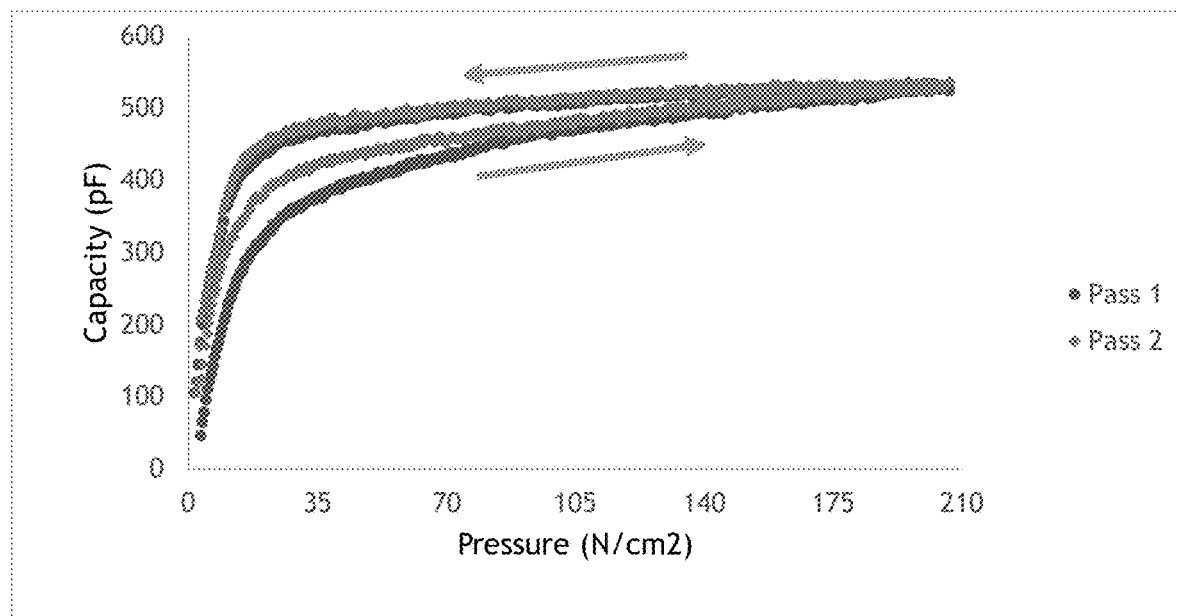
FIG. 12C shows a graph of capacity vs. pressure for a high-pressure response test of an electroactive polymer capacitive sensor (blue: Pass 1; red: Pass 2).

High-pressure response test. The high-pressure response test was performed by positioning a sensor under a mechanical press and increasing then decreasing the pressure linearly while measuring the sensor response. Capacitance of the sensor was measured against a triangular pressure pattern from 0 $N/cm^2$ to 200 $N/cm^2$ with a pressure rate of 100 $N/cm^2$ over 2 passes. Results are shown in FIG. 12C. The arrows indicate the direction of the cycles. Due to some instability of the measurement system at low pressure, some low-pressure data points were not available.

The measurements showed a general non-linear behavior. Nevertheless, local linear behaviors could be observed. The hysteresis coming from the sensor elasticity was still present. By comparing the two passes, we could observe that the values given by the sensor are within a 10% range. This measurement shows a saturation toward the high pressures allowing estimation of the maximal measurable pressure not far above 100 N/cm².

Figure 12D:
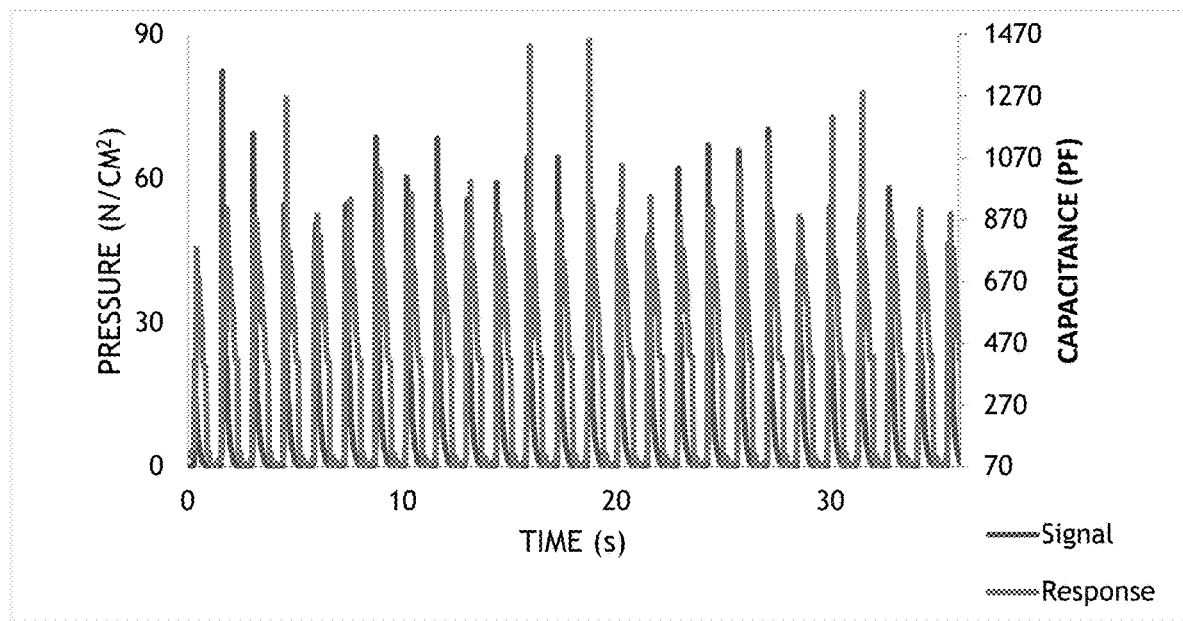
FIG. 12D is a graph showing pressure, capacitance and time, indicating capacitance of an electroactive polymer capacitive sensor and pressure applied measured against time on a 1 Hz repetition rate impact test (blue: Signal; red: Response).

Frequency response test. The frequency response test was performed by positioning a sensor under a mechanical press and applying impacts to the sensor at a constant rate while measuring the sensor response. Capacitance of the sensor and pressure applied were measured against time on a 1 Hz repetition rate impact test. Results are shown in FIG. 12D. This measurement showed that the sensor is able to measure a 1 Hz repetitive impact and still be able to go back to its baseline before the next impact. This result shows that the frequency response of the sensor is above 1 Hz.

Customizability. The sensitivity and the measurable range of the sensor depend on the dielectric layer permittivity, its thickness and its compressibility. By adjusting these properties, it is possible to select the sensor's characteristics according to a specific application. Moreover, different dielectric layers can be used in the same array in order to obtain a sensing surface with variable sensitivity, spatial resolution, or measurable range, depending on the specific application.

Electrical connection. The internal electric connectivity of the sensor is made using EAP wires. This allow preservation of the mechanical properties of the sensor. EAP wires were also used to make the interface with the standard electric circuitry. The interface can be made for example using a mechanical connection such as terminal blocks or ribbon DIP headers.

Axis of improvement. The linearity of the sensor response, its hysteresis and its drift can be improved by changing the EAP elasticity and the manufacturing process. For instance, using a polymer printing technology can highly reduce the manufacturing defects while enabling smaller and denser sensors to be produce on a large surface, and in a very reliable way.

The results showed that symmetric SSEPAs can be used to sense pressure and tactile forces applied thereto (such as bending), suitable for wearable sensors that are flexible and stretchable.

Example 15

Bending Actuator Characterization

Curvature radius. The actuator was placed a few millimeters above of a millimeter paper sheet in order to make it bend sideways. The actuator was then connected to a power supply (e.g. 5 V, 300 mA) using an electric clamp with two electrodes. The actuator was straightened and the positions of both ends of the actuator were noted. The actuator was then powered. After waiting until the bending reached maximum, the position of the free end of the actuator was noted. The curvature radius of the actuator was computed from the three noted positions using simple geometry.

Blocking force. The actuator was placed in order to make it bend sideways and connected to a power supply (e.g., 5 V, 300 mA) using an electric clamp with two electrodes. The actuator was then powered. After waiting until the bending reached maximum, the actuator was placed in contact with the force sensor (e.g., MilliNewton B-0400-L-C-A). The initial measured force was noted. The current polarity was inverted. After waiting until the force measured was maximum, the maximum measured force was noted. The blocking force is the difference between the maximum and the initial measured forces.

Results from bending actuator characterization are shown in Table 6.

TABLE 6

Bending actuator characterization.

| ID Actuator Name | EAP (SS-M-32) Thickness [mm] | SPE (SS-M-04-g) Thickness [mm] | Dimensions | | | Bending Free | | | Properties | |
|---|---|---|---|---|---|---|---|---|---|---|
| | | | Width [mm] | Length [mm] | Thickness [mm] | length [mm] | Angle [deg] | Curvature radius [mm] | Strain Ratio [%] | Blocking force [mN] |
| JP-JB-01-A-01 | 0.11 | 0.5 | 10 | 50 | 0.696 ± 0.004 | 43 ± 2 | 37.71 ± 3.36 | 65.34 ± 8.86 | 1.07 ± 0.15 | 3.0 ± 0.1 |
| JP-JB-01-A-02 | 0.11 | 0.5 | 10 | 50 | 0.660 ± 0.004 | 43 ± 2 | 43.60 ± 3.46 | 56.50 ± 7.11 | 1.17 ± 0.16 | 1.6 ± 0.1 |
| JP-JB-01-A-03 | 0.11 | 0.5 | 10 | 50 | 0.725 ± 0.004 | 43 ± 2 | 48.20 ± 2.38 | 51.11 ± 4.90 | 1.43 ± 0.15 | 4.1 ± 0.1 |
| JP-JB-01-B-01 | 0.11 | 0.3 | 10 | 50 | 0.483 ± 0.004 | 43 ± 2 | 83.97 ± 4.01 | 29.34 ± 2.77 | 1.66 ± 0.17 | 0.3 ± 0.1 |
| JP-JB-01-B-02 | 0.11 | 0.3 | 10 | 50 | 0.492 ± 0.004 | 43 ± 2 | 94.77 ± 4.77 | 26.00 ± 2.52 | 1.91 ± 0.20 | 0.5 ± 0.1 |
| JP-JB-01-B-03 | 0.11 | 0.3 | 10 | 50 | 0.479 ± 0.004 | 43 ± 2 | 92.44 ± 4.87 | 26.65 ± 2.64 | 1.81 ± 0.20 | 0.5 ± 0.1 |
| JP-JB-01-C-01 | 0.11 | 1 | 10 | 50 | 0.928 ± 0.004 | 43 ± 2 | 42.08 ± 3.54 | 58.56 ± 7.66 | 1.60 ± 0.22 | 5.0 ± 0.1 |
| JP-JB-01-C-02 | 0.11 | 1 | 10 | 50 | 0.888 ± 0.004 | 43 ± 2 | 44.61 ± 3.55 | 55.22 ± 6.96 | 1.62 ± 0.21 | 5.0 ± 0.1 |
| JP-JB-01-C-03 | 0.11 | 1 | 10 | 50 | 0.984 ± 0.004 | | | | | |
| JP-JB-01-D-01 | 0.11 | 0.5 | 5 | 50 | 0.713 ± 0.004 | 43 ± 2 | 38.58 ± 3.45 | 63.86 ± 8.67 | 1.12 ± 0.16 | 1.9 ± 0.1 |
| JP-JB-01-D-02 | 0.11 | 0.5 | 5 | 50 | 0.696 ± 0.004 | 43 ± 2 | 58.11 ± 3.78 | 42.40 ± 4.73 | 1.66 ± 0.20 | 1.9 ± 0.1 |
| JP-JB-01-D-03 | 0.11 | 0.5 | 5 | 50 | 0.686 ± 0.004 | 43 ± 2 | 54.36 ± 3.71 | 45.32 ± 5.20 | 1.53 ± 0.19 | 1.5 ± 0.1 |
| JP-JB-01-E-01 | 0.11 | 0.5 | 20 | 50 | 0.763 ± 0.004 | 43 ± 2 | 24.19 ± 3.17 | 101.85 ± 18.07 | 0.75 ± 0.14 | 4.5 ± 0.1 |
| JP-JB-01-E-02 | 0.11 | 0.5 | 20 | 50 | 0.783 ± 0.004 | 43 ± 2 | 42.08 ± 3.54 | 58.56 ± 7.66 | 1.35 ± 0.18 | 5.3 ± 0.1 |

TABLE 6-continued

Bending actuator characterization.

| ID Actuator Name | EAP (SS-M-32) Thickness [mm] | SPE (SS-M-04-g) Thickness [mm] | Dimensions Width [mm] | Dimensions Length [mm] | Dimensions Thickness [mm] | Bending Free length [mm] | Bending Angle [deg] | Bending Curvature radius [mm] | Properties Strain Ratio [%] | Properties Blocking force [mN] |
|---|---|---|---|---|---|---|---|---|---|---|
| JP-JB-01-E-03 | 0.11 | 0.5 | 20 | 50 | 0.768 ± 0.004 | 43 ± 2 | 35.18 ± 3.34 | 70.02 ± 9.91 | 1.10 ± 0.16 | 3.4 ± 0.1 |
| JP-JB-01-F-01 | 0.11 | 0.5 | 10 | 25 | 0.730 ± 0.004 | 23 ± 2 | 25.61 ± 6.08 | 51.46 ± 16.69 | 1.43 ± 0.47 | 7.5 ± 0.1 |
| JP-JB-01-F-02 | 0.11 | 0.5 | 10 | 25 | 0.713 ± 0.004 | 21 ± 2 | 28.07 ± 6.74 | 42.86 ± 14.37 | 1.68 ± 0.58 | 6.6 ± 0.1 |
| JP-JB-01-F-03 | 0.11 | 0.5 | 10 | 25 | 0.647 ± 0.004 | 23 ± 2 | 14.86 ± 5.54 | 88.66 ± 40.75 | 0.73 ± 0.34 | 5.2 ± 0.1 |
| JP-JB-01-G-01 | 0.11 | 0.5 | 10 | 100 | 0.729 ± 0.004 | 93 ± 2 | 52.55 ± 1.74 | 101.40 ± 5.54 | 0.72 ± 0.04 | 1.3 ± 0.1 |
| JP-JB-01-G-02 | 0.11 | 0.5 | 10 | 100 | 0.737 ± 0.004 | 93 ± 2 | 56.60 ± 1.75 | 94.14 ± 4.94 | 0.79 ± 0.05 | |
| JP-JB-01-G-03 | 0.11 | 0.5 | 10 | 100 | 0.758 ± 0.004 | 93 ± 2 | 53.71 ± 1.74 | 99.21 ± 5.35 | 0.77 ± 0.05 | 1.7 ± 0.1 |
| JP-JB-02-A-01 | 0.11 | 0.5 | 10 | 50 | 1.211 ± 0.004 | 43 ± 2 | 24.19 ± 3.17 | 101.85 ± 18.07 | 1.20 ± 0.22 | 5.6 ± 0.1 |
| JP-JB-02-A-02 | 0.11 | 0.5 | 10 | 50 | 1.218 ± 0.004 | 43 ± 2 | 24.19 ± 3.17 | 101.85 ± 18.07 | 1.20 ± 0.22 | 5.7 ± 0.1 |
| JP-JB-02-A-03 | 0.11 | 0.5 | 10 | 50 | 1.128 ± 0.004 | 43 ± 2 | 26.78 ± 3.20 | 91.98 ± 15.26 | 1.23 ± 0.21 | 3.4 ± 0.1 |
| JP-JB-01-I-01 | 0.11 | 0.3 | 4 | 10 | 0.285 ± 0.004 | 9 ± 2 | 12.68 ± 13.97 | 40.67 ± 53.85 | 0.70 ± 0.94 | 1.1 ± 0.1 |
| JP-JB-01-I-02 | 0.11 | 0.3 | 4 | 10 | 0.280 ± 0.004 | 9 ± 2 | 12.68 ± 13.97 | 40.67 ± 53.85 | 0.69 ± 0.93 | 0.7 ± 0.1 |
| JP-JB-01-I-03 | 0.11 | 0.3 | 4 | 10 | 0.263 ± 0.004 | 9 ± 2 | 25.06 ± 14.83 | 20.58 ± 16.75 | 1.29 ± 1.07 | 1.0 ± 0.1 |
| JP-JB-01-J-01 | 0.11 | 0.3 | 6 | 15 | 0.436 ± 0.004 | 14 ± 2 | 8.17 ± 8.73 | 98.17 ± 118.85 | 0.45 ± 0.54 | 3.4 ± 0.1 |
| JP-JB-01-J-02 | 0.11 | 0.3 | 6 | 15 | 0.468 ± 0.004 | 14 ± 2 | 12.23 ± 8.96 | 65.58 ± 57.41 | 0.72 ± 0.64 | 3.0 ± 0.1 |
| JP-JB-01-J-03 | 0.11 | 0.3 | 6 | 15 | 0.439 ± 0.004 | 14 ± 2 | 16.26 ± 9.17 | 49.33 ± 34.86 | 0.89 ± 0.64 | 2.5 ± 0.1 |
| JP-JB-01-K-01 | 0.11 | 0.3 | 8 | 20 | 0.501 ± 0.004 | 19 ± 2 | 18.92 ± 7.23 | 57.52 ± 28.02 | 0.87 ± 0.43 | 3.5 ± 0.1 |
| JP-JB-01-K-02 | 0.11 | 0.3 | 8 | 20 | 0.507 ± 0.004 | 19 ± 2 | 18.92 ± 7.23 | 57.52 ± 28.02 | 0.89 ± 0.44 | 2.7 ± 0.1 |
| JP-JB-01-K-03 | 0.11 | 0.3 | 8 | 20 | 0.474 ± 0.004 | 19 ± 2 | 18.92 ± 7.23 | 57.52 ± 28.02 | 0.83 ± 0.41 | 3.0 ± 0.1 |

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A solid-state electroactive polymer actuator, SSEPA, comprising:
   one or two layers of an electroactive polymer, EAP, composition, the EAP composition comprising about 15-60 wt % PVA, about 5-40 wt % PEDOT:PSS, and about 10-40 wt % glycerol;
   one layer of a solid-state polymer electrolyte, SPE, composition, the SPE composition comprising about 20-60 wt % of a plasticizer, about 10-60 wt % of a film-forming polymer, and about 5-25 wt % of an ionizable salt;
   wherein the SPE composition layer is sandwiched between the two EAP composition layers and adhered thereto;
   wherein, when one layer of the EAP composition is present, one side of the SPE composition layer is attached to the EAP composition layer.

2. The SSEPA of claim 1, wherein the film-forming polymer is selected from poly(vinyl alcohol), PVA; polyethylene glycol, PEG; styrene-butadiene rubber, SBR; poly(ethylene-vinyl acetate), PEVAc; polyvinyl acetate, PVAc; polyvinylpyrrolidone, PVP; polyvinylidene fluoride, PVDF; (PVDF), poly(vinylidene fluoride-co-hexafluoropropylene), PVDF-HFP; polyethylene oxide, PEO; EG or PEG esters of (meth)acrylic acid derivatives, amylopectin, amylose, starch, and combinations thereof.

3. The SSEPA of claim 1, wherein the plasticizer is selected from glycerol, polyethylene glycol, PEG; ethylene glycol, N-ethyl toluene sulfonamide, a fluorosurfactant, and 4-Dodecylbenzenesulfonic acid, DBSA.

4. The SSEPA of claim 1, wherein the ionizable salt is selected from lithium perchlorate, $LiClO_4$; lithium bis(trifluoromethanesulfonyl)imide, LiTFSI; lithium polyacrylate, LiPAA; lithium chloride, LiCl; sodium chloride, NaCl; sodium sulfate, $NaSO_4$, and sodium carbonate, sodium nitrate, sodium carbonate, potassium chloride, potassium bromide), potassium perchlorate, potassium nitrate, potassium nitrite, potassium ferricyanide, $K_3Fe(CN)_6$; and potassium ferrocyanide, $K_4Fe(CN)_6$.

5. The SSEPA of claim 1, wherein the EAP composition comprises about 45.5 wt % PVA, about 29.5 wt % PEDOT:PSS, and about 25 wt % glycerol.

6. The SSEPA of claim 1, wherein the SPE composition comprises about 40.4 wt % glycerol, about 14.7 wt % starch, about 14.7 wt % PVA, about 14 wt % $LiClO_4$, about 8.8 wt % nanocrystalline cellulose NCC and about 7.4 wt % Kaolin clay.

7. The SSEPA of claim 1, wherein the electroactive polymer is pre-strained before use or before actuation or wherein the EAP composition layer is pre-stretched during manufacture thereof to increase pressure generation of the SSEPA.

8. The SSEPA of claim 1, wherein the EAP composition layers and/or the SPE composition layer are in the form of a thin film, each layer independently having a thickness of from about 50 μm to about 2000 μm, from about 50 μm to about 500 μm, from about 100 μm to about 2000 μm, or of about 250 μm, or wherein the thickness of the SSEPA is from about 1000 μm to about 1200 μm, or about 1100+/−100 μm.

9. The SSEPA of claim 1, wherein one or more of the EAP composition layers and the SPE composition layer are made by casting, solution casting, dipping, spin coating, spraying, compression molding or extrusion.

10. The SSEPA of claim 1, wherein one or more of the EAP composition layers and the SPE composition layer further comprises an additive, wherein the additive is a UV stabilizer, a crosslinking agent, a rubbery component, an elastic component, a suspension stabilizer, or a combination thereof.

11. The SSEPA of claim 1, wherein the SSEPA has one or more of the following performance characteristics: blocking force of from about 200 mN to about 1 N; total actuation pressure of about 50 mmHg; extension ratio of from about 20% to about 200%; and a Young's modulus of at least about 5 MPa.

12. The SSEPA according to claim 1, wherein the SSEPA is an asymmetric SSEPA that comprises only one layer of the EAP composition, the SPE composition layer being sandwiched between the EAP composition and a carbon electrode.

13. The SSEPA according to claim 2, wherein said EG or PEG esters of (meth)acrylic acid derivatives are selected from PEG acrylate, PEGA; PEG diacrylate, PEGDA; PEG methacrylate, PEGMA; PEG dimethacrylate, PEGDMA; glycerol acrylate, glycerol diacrylate, glycerol methacrylate, glycerol dimethacrylate, glycidyl acrylate, glycidyl methacrylate, and propylene carbonate methacrylate.

14. The SSEPA of claim 1, wherein one or more of the EAP composition and the SPE composition further comprise 0-50 wt % of a reinforcing filler, or 1-15 wt % of a reinforcing filler, or 3-5 wt % of a reinforcing filler.

15. The SSEPA of claim 14, wherein the reinforcing filler is graphene, graphite, carbon black, graphene oxide, carbon nanotubes, or a combination thereof.

16. The SSEPA of claim 14, wherein the reinforcing filler is nanocrystalline cellulose or clay.

17. The SSEPA of claim 16, wherein the reinforcing filler is montmorillonite, silicon dioxide, $SiO_2$; or kaolin clay.

18. An electromechanical device comprising one or more SSEPA as described in claim 1, wherein the electromechanical device is a generator, a sensor, or another type of energy transducer.

19. An article comprising one or more SSEPA as described in claim 1, wherein the article comprises an implantable artificial muscle, an artificial sphincter, a pump, a valve, an optical electrode, an organic electronic device, a robotic device, a speaker, a disk drive, a prosthetic device, a spacesuit, or a wearable item configured to be worn on a body or on at least one body part of a subject.

* * * * *